US011058300B2

(12) United States Patent
Rogers et al.

(10) Patent No.: US 11,058,300 B2
(45) Date of Patent: Jul. 13, 2021

(54) WIRELESS SURFACE MOUNTABLE SENSORS AND ACTUATORS

(71) Applicants: NORTHWESTERN UNIVERSITY, Evanston, IL (US); THE BOARD OF TRUSTEES OF THE UNIVERSITY OF ILLINOIS, Urbana, IL (US)

(72) Inventors: John A. Rogers, Wilmette, IL (US); Seungyong Han, Evanston, IL (US); Sang Min Won, Evanston, IL (US); Jeonghyun Kim, Urbana, IL (US)

(73) Assignees: NORTHWESTERN UNIVERSITY, Evanston, IL (US); THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 163 days.

(21) Appl. No.: 16/481,147

(22) PCT Filed: Jan. 26, 2018

(86) PCT No.: PCT/US2018/015389
§ 371 (c)(1),
(2) Date: Jul. 26, 2019

(87) PCT Pub. No.: WO2018/140693
PCT Pub. Date: Aug. 2, 2018

(65) Prior Publication Data
US 2021/0127975 A1 May 6, 2021

Related U.S. Application Data

(60) Provisional application No. 62/451,248, filed on Jan. 27, 2017.

(51) Int. Cl.
*A61B 5/00* (2006.01)
*A61B 5/0205* (2006.01)
(Continued)

(52) U.S. Cl.
CPC ............ *A61B 5/0024* (2013.01); *A61B 5/002* (2013.01); *A61B 5/02055* (2013.01);
(Continued)

(58) Field of Classification Search
CPC ... A61B 5/0024; A61B 5/002; A61B 5/02055; A61B 5/6804; A61B 5/7275;
(Continued)

(56) References Cited

U.S. PATENT DOCUMENTS 5,116,457 A 5/1992 Jerman
6,832,251 B1 12/2004 Gelvin et al.
(Continued)

FOREIGN PATENT DOCUMENTS

WO 2016025438 A1 2/2016
WO 2016025468 A1 2/2016
(Continued)

OTHER PUBLICATIONS

Lacost, Battery-Less NFC/RFID Temperature Sensing Patch, Application Report [online] Texas Instruments, Feb. 2016.
(Continued)

*Primary Examiner* — Jonathan T Kuo
(74) *Attorney, Agent, or Firm* — Locke Lord LLP; Tim Tingkang Xia, Esq.

(57) ABSTRACT

Provided herein are medical devices comprising a plurality of biologically interactive devices configured for interacting with a large area biological surface. The biologically interactive devices each may comprise a sensor for measuring a physiological parameter. A wireless controller is configured to wirelessly operate the plurality of biologically interactive devices. A wireless transmitter is configured for wirelessly communicating an output from said plurality of biologically interactive devices to a remote receiver. The medical devices are particularly suited for measuring one or both of pressure
(Continued)

and temperature, with compatibility for incorporating additional sensors of interest.

11 Claims, 38 Drawing Sheets

(51) Int. Cl.
    *A61B 5/026*     (2006.01)
    *A61B 5/01*     (2006.01)
    *A61B 5/0533*     (2021.01)
    *A61B 5/145*     (2006.01)
    *A61B 5/08*     (2006.01)

(52) U.S. Cl.
    CPC .......... *A61B 5/6804* (2013.01); *A61B 5/7275* (2013.01); *A61B 5/746* (2013.01); *A61B 5/0059* (2013.01); *A61B 5/015* (2013.01); *A61B 5/026* (2013.01); *A61B 5/0533* (2013.01); *A61B 5/0816* (2013.01); *A61B 5/14542* (2013.01); *A61B 5/4266* (2013.01); *A61B 5/447* (2013.01); *A61B 5/4818* (2013.01); *A61B 2503/40* (2013.01); *A61B 2560/0214* (2013.01); *A61B 2562/0247* (2013.01)

(58) Field of Classification Search
    CPC ....... A61B 5/746; A61B 5/0059; A61B 5/015; A61B 5/026; A61B 5/0533; A61B 5/0816; A61B 5/14542; A61B 5/4266; A61B 5/447; A61B 5/4818; A61B 2503/40; A61B 2560/0214; A61B 2562/0247
    See application file for complete search history.

(56) References Cited

U.S. PATENT DOCUMENTS

| | | |
|---|---|---|
| 8,849,379 B2 | 9/2014 | Abreu |
| 10,441,185 B2* | 10/2019 | Rogers ................ A61N 1/0472 |
| 2009/0171180 A1 | 7/2009 | Pering et al. |
| 2013/0041235 A1* | 2/2013 | Rogers ................ A61B 5/1107 |
| | | 600/306 |
| 2013/0317367 A1* | 11/2013 | Shuler ................ A61B 5/0075 |
| | | 600/473 |
| 2015/0035680 A1* | 2/2015 | Li ........................... G01K 1/14 |
| | | 340/584 |
| 2015/0373831 A1 | 12/2015 | Rogers et al. |
| 2019/0350484 A1* | 11/2019 | Coleman ................ A61B 5/015 |

FOREIGN PATENT DOCUMENTS

| | | |
|---|---|---|
| WO | 2016196673 A1 | 12/2016 |
| WO | 2016196675 A1 | 12/2016 |
| WO | 2017004576 A1 | 1/2017 |

OTHER PUBLICATIONS

Kenry et al., Emerging flexible and wearable physical sensing platforms for healthcare and biomedical applications, Microsystems & Nanoengineering (2016) 2, 16043, Sep. 26, 2016.

United States Patent and Trademark Office (ISR/US) "International Search Report for PCT/US2018/015389", US, dated Mar. 26, 2018.

* cited by examiner

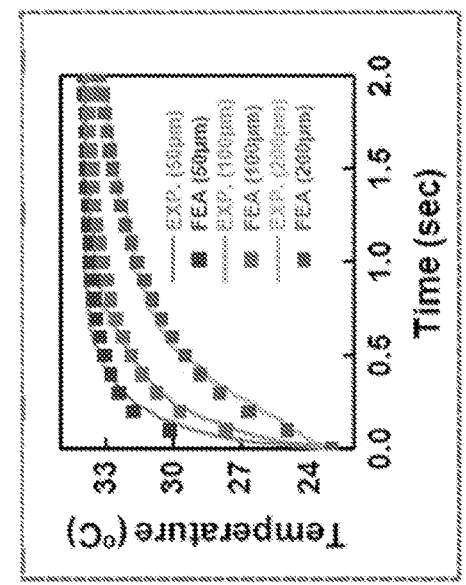
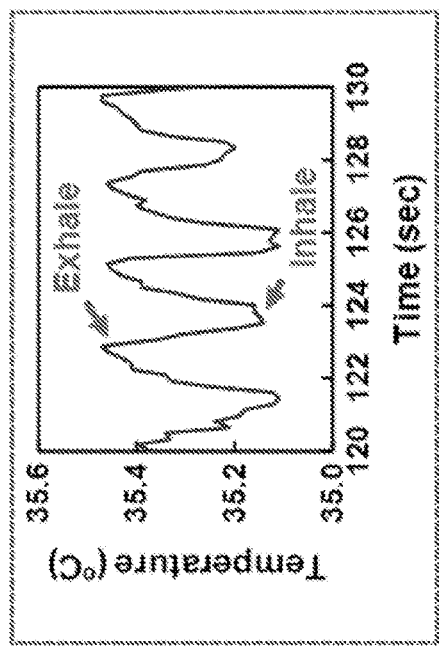
FIG. 2B
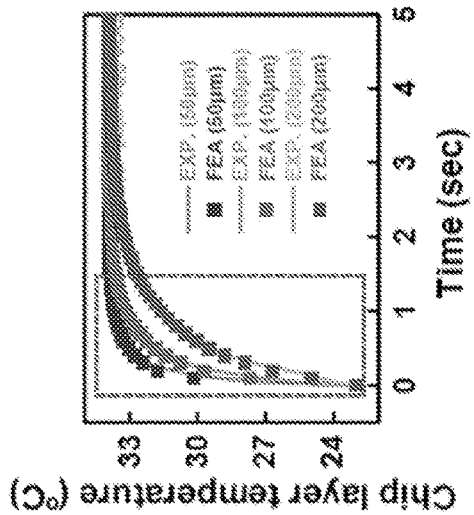
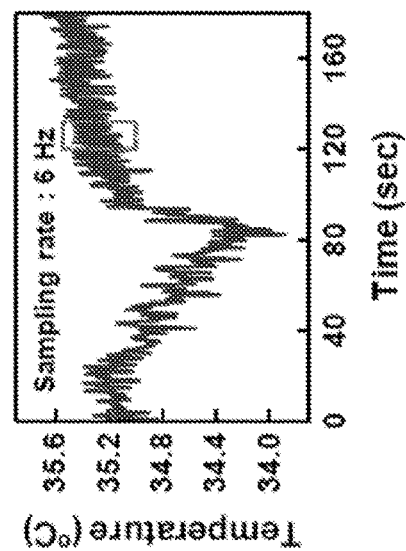
FIG. 2D
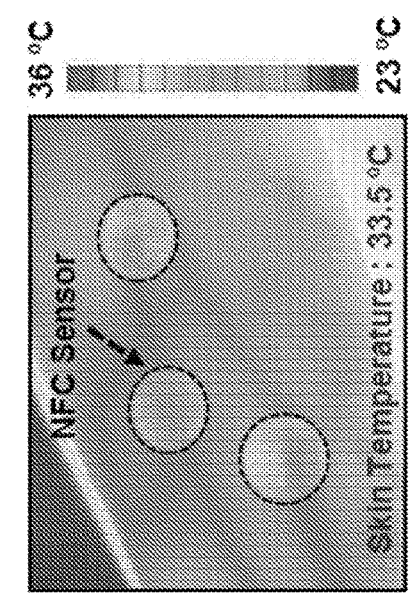
FIG. 2A
FIG. 2C

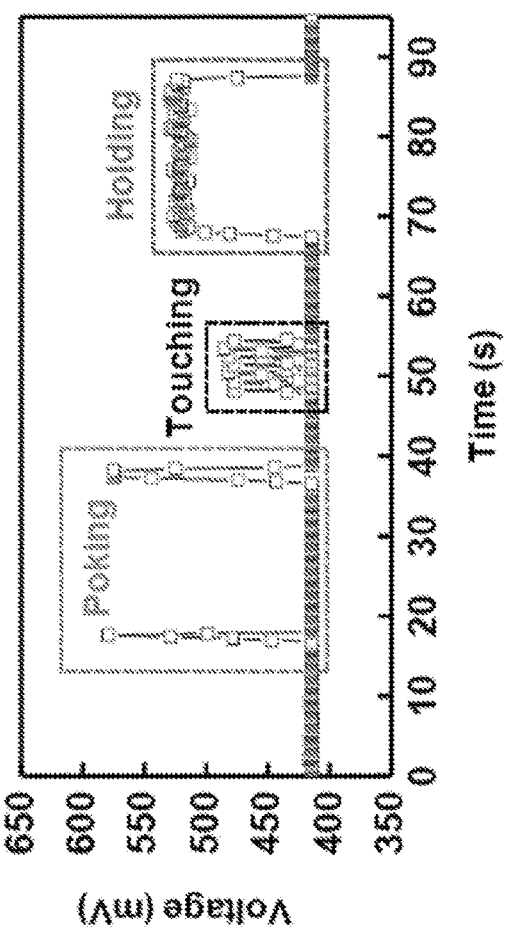
FIG. 2G
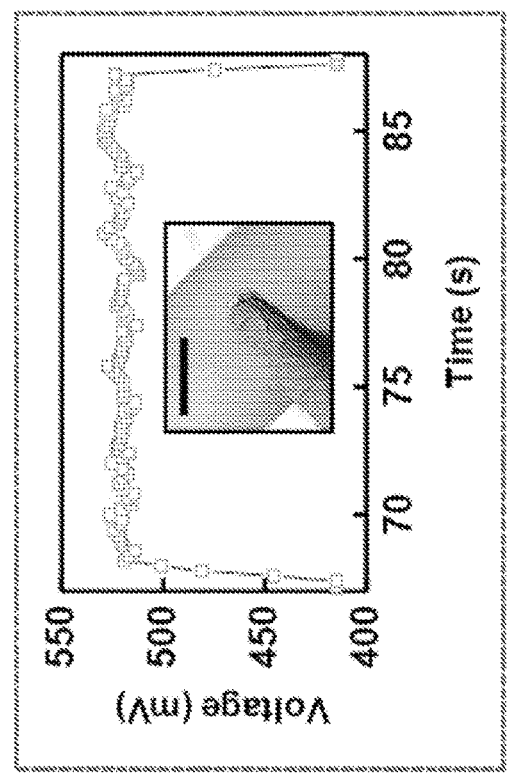
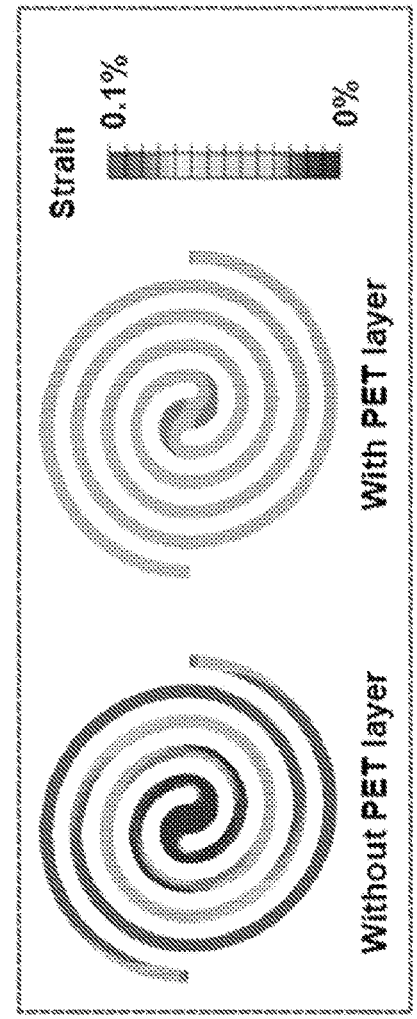
FIG. 2H
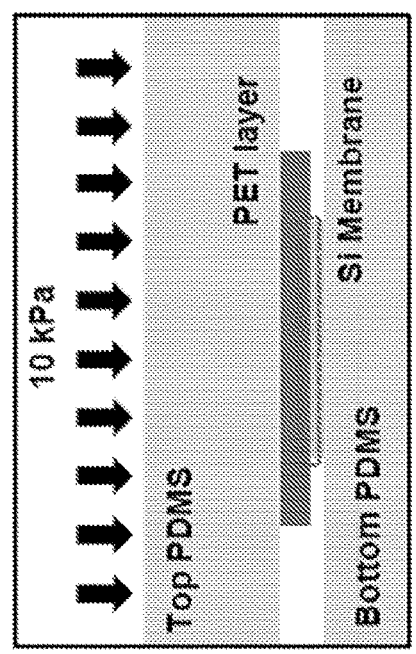

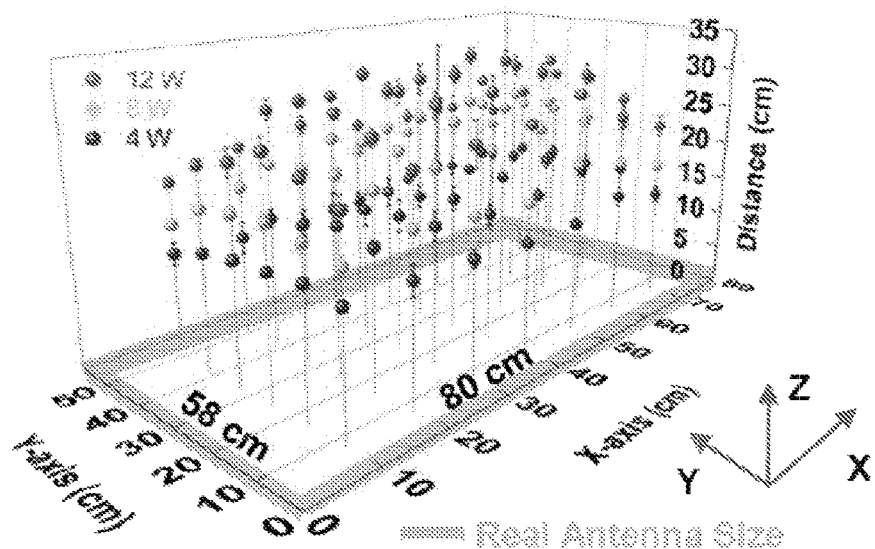
FIG. 3D
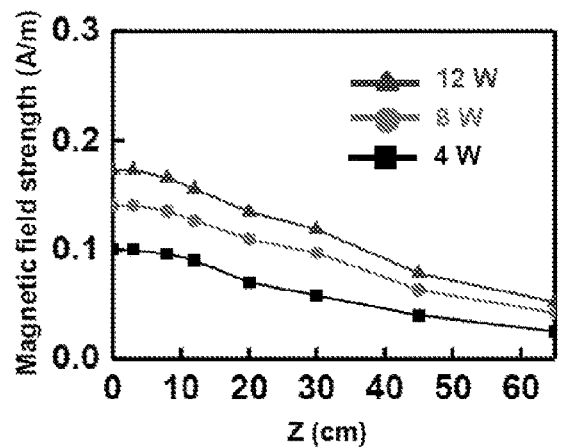
FIG. 3E
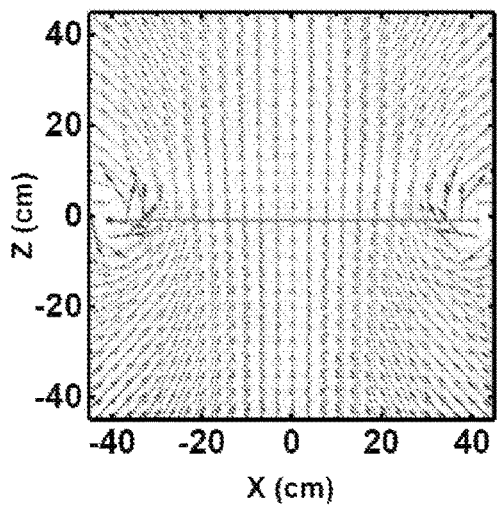 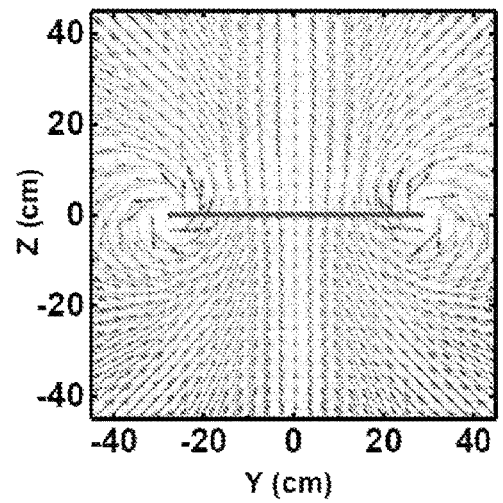
FIG. 3F  FIG. 3G

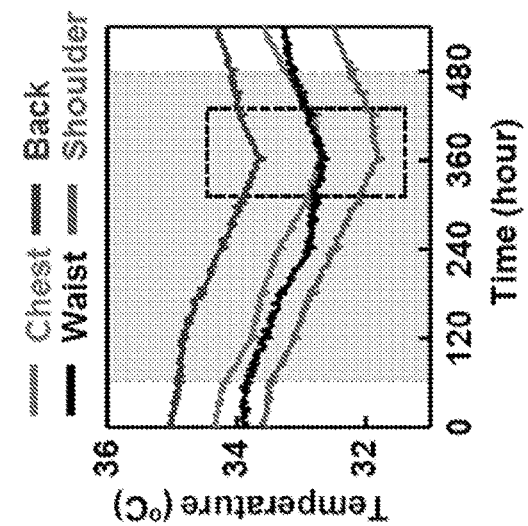
FIG. 4D
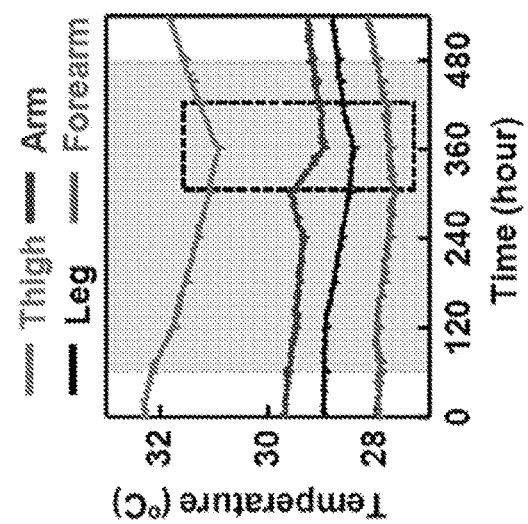
FIG. 4E
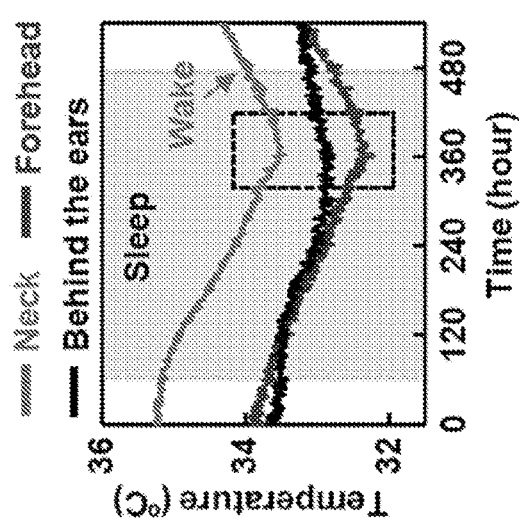
FIG. 4F
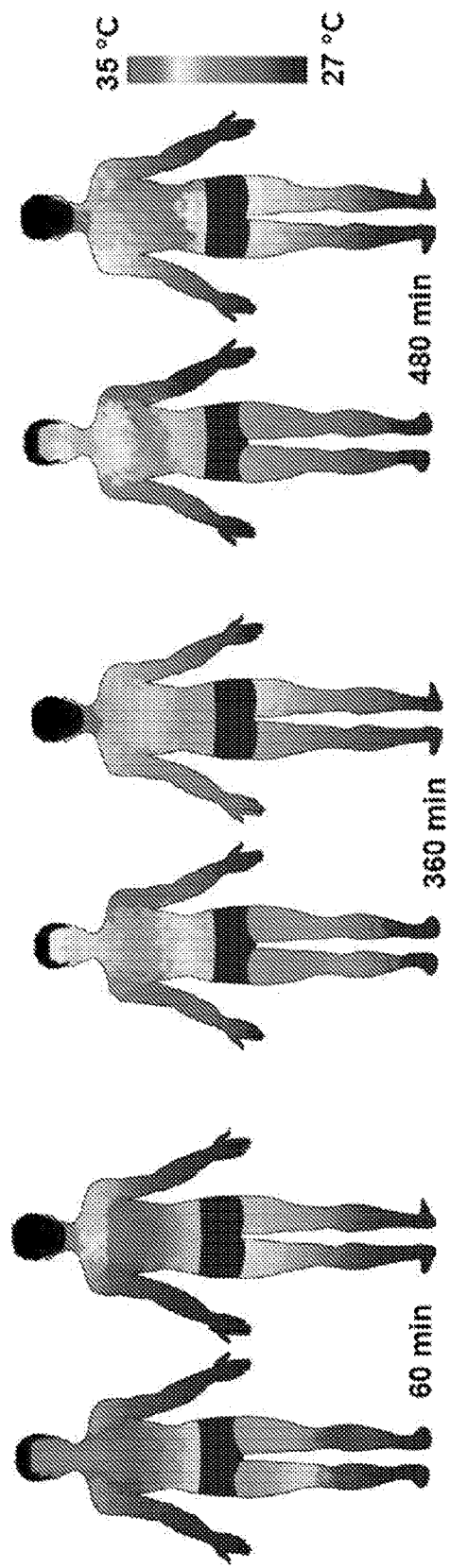
FIG. 4G
FIG. 4H
FIG. 4I

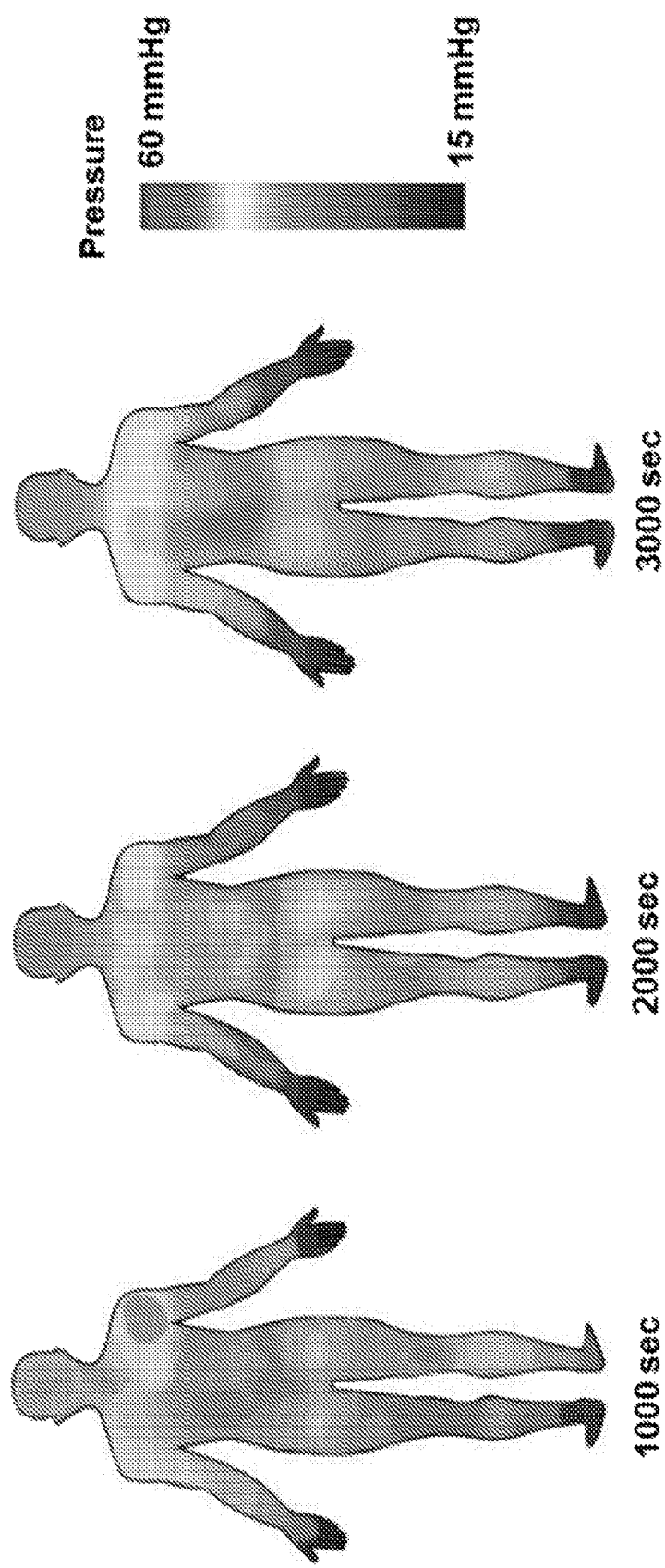

Circle design

Line design

Normal stresses on skin — Shear stresses on skin

−20kPa　20kPa

WIRELESS SURFACE MOUNTABLE SENSORS AND ACTUATORS

CROSS-REFERENCE TO RELATED APPLICATIONS

This application is a U.S. national stage application of PCT Patent Application No. PCT/US2018/015389, filed Jan. 26, 2018, which itself claims priority to and the benefit of U.S. Provisional Patent Application No. 62/451,248, filed Jan. 27, 2017, each of which is hereby incorporated by reference in its entirety.

BACKGROUND OF INVENTION

Recent effort establishes the foundations for thin, soft, skin-like systems capable of precise, continuous measurements of physiological health, with broad potential relevance to clinical healthcare. Although several interesting possibilities that rely on one or a small number of such skin-mounted devices appear in recent literature, there is a need in the art for practical and reliable devices that incorporate large-scale, distributed arrays for full-body, spatio-temporal mapping of physiological parameters relevant for a wide range of applications in a manner that is wireless and non-obtrusive.

Conventional devices currently in use for measuring a physiological parameter suffer from limitations one or more limitations around, having to be hard wired to separate components, are uncomfortable, cannot provide real-time continuous monitoring, and are not amenable to full-body monitoring.

Those limitations are addressed herein by utilizing materials, device designs, wireless power delivery and communication strategies and overall system architectures for skin-like, battery-free sensors and/or actuators that can be deployed and operated at scale, across the entire body and large subregions thereof. Combined experimental and theoretical investigations of the devices and their modes for wireless operation establish the key features of these systems. Successful trials on human subjects in clinical sleep laboratories and in adjustable hospital beds demonstrate functionality of immediate practical importance for an exemplified application, specifically in monitoring circadian cycles and in mitigating risks for pressure-induced skin ulcers.

SUMMARY OF THE INVENTION

The devices and related methods provided herein address the need for distributed large collections of miniaturized skin-mounted devices over large areas in a manner having complete wireless control and powering. The actual active part of the device can be formed from relatively simple low cost patches or islands that contain sensors and/or actuators, including for any one or more of mechanical, thermal and/or electrical stimulation and/or sensing. Such a fundamental platform provides access to a multi-modal, large-scale collection of devices that may be distributed across a body surface. For monitoring and/or control, a graphical user interface may be operably connected to the devices, including to provide spatio-temporal configurations in real-time, including over the internet. Applications for the sensor-focused aspects include for monitoring of at-risk individuals, physiological assessments, including for individuals or high-throughput monitoring of a group or herd of individuals, including livestock, and general monitoring and well-being in a range of settings.

Any of the devices provided herein may have an on-board power supply such as a battery or may be wirelessly powered, such as by NFC. Any of the devices may have a distribution of the same type of sensor patches, or may have different types of sensors distributed at different locations. The number of devices may range from one to a very high number, such as up to $1 \times 10^5$. The devices may have a range of form factors, including form-factors suitable for interacting with skin surface. Any of the devices may be mounted to the skin surface, or may be mounted on a skin-conformable material, such as a fabric or garment. Any of the devices and methods may be used to monitor physical parameters associated with an animal. For example, livestock, pets, or any other animal where it is desired to measure one or more physical parameters, including high-throughput monitoring. Of course, any of the devices and methods may be used with a human.

Provided herein are devices configured for monitoring of one or more physiological parameters. For example, the device may be a medical device comprising: a plurality of biologically interactive devices configured for interacting with a large area biological surface. Each of the biologically interactive devices may comprise a sensor for measuring a physiological parameter, such as one or both of pressure and temperature. The devices described herein are, of course, compatible with measuring a wide range of parameters, depending on the application of interest, such as conductivity, hydration, compliance, an optical property (intensity, color), thickness, presence/amount of a chemical, radiation, blood flow, and the like. Those parameters may be in place of, or in addition to, pressure and/or temperature. A wireless controller is configured to wirelessly operate the plurality of biologically interactive devices and a wireless transmitter is configured for wirelessly communicating an output from said plurality of biologically interactive devices to a remote receiver. In this manner, there need not be a directly wired connection from the device to an externally-located component in order to control, run and communicate with the medical device.

Any of the devices and methods may be used to measure a physiological parameter that is pressure, temperature, galvanic skin response, impedance, thermal transport, sweat release, blood flow, blood oxygenation and any combination thereof. For example, any of the devices and methods may have a pressure sensor and/or a temperature sensor to measure pressure and/or temperature. Optionally, one or more additional physiological parameters may be measure in addition to pressure and temperature. Any of the devices and methods may be for measuring a physiological parameter of skin.

The medical device may further comprise a near field communication (NFC) chip to provide wireless power delivery to the sensors and wireless data communication between the biologically interactive devices and the wireless controller.

The wireless controller may provide two-way communication with the plurality of biologically interactive devices to acquire physiological parameter data from the plurality of sensors and to operate the plurality of biologically interactive devices. The wireless controller comprises a long-range reader, such that the communication may occur over relatively convenient distances. For example, the long-range reader may facilitate communication over a distance greater than 50 cm, greater than 1 m, greater than 10 m, or between about 50 cm and 20 m, including distances corresponding to between a patient's bedside and a computer monitoring station either beside the bedside, at a nurses station, or to a remote centralized monitoring station.

The wireless controller may be configured to acquire a continuous data stream from the medical device and generate a spatio-temporal map of one or more physiological parameters detected by the sensors. The spatio-temporal map may have a map area that corresponds to a full-body surface. The full-body surface may correspond to at least 80% of a living animal skin surface, or select portions thereof, such as at least 80% of the torso, an extremity, or sub-portions thereof, depending on the application of interest. For example, for bed-rest ulcer applications, it may be that the portion of the body that faces the bed is important from a pressure-assessment monitoring point-of-view, with the portion of the body not facing the bed of less importance. Accordingly, an 80% coverage of that portion of the body of interest may be mapped to provide a corresponding full-body coverage.

The medical device may further comprise a processor to provide an average physiological parameter over the full-body surface, a time-integrated physiological parameter, a rate of change of the physiological parameter, or any combination thereof.

The medical device may have a wireless transmission and receipt range that is greater than or equal to 10 cm, including greater than or equal to 10 cm and less than or equal to many kilometers (for cellular/internet-type transmissions) or less than or equal to 100 m (for local transmission applications, such as localized monitoring by a localized caregiver).

The medical device is compatible with interfacing with skin from a range of platforms. For example, the plurality of biologically interactive devices may be directly or indirectly skin-mounted to provide a spatial distribution map of the physiological parameter. Any of the devices and methods described herein may have the plurality of biologically interactive devices configured to directly connect to a skin surface of a living animal.

Any of the devices and methods described herein may have the plurality of biologically interactive devices embedded or connected to a garment, wherein the garment is configured to be worn by a living animal to provide the plurality of biologically interactive devices adjacent to a skin surface.

Any of the medical devices may comprise at least 20 biologically interactive devices.

Any of the devices provided herein may be further described in terms of the biologically interactive device. For example, each biologically interactive device may comprise: an integrated circuit chip for NFC communication; a wireless energy harvester; a temperature sensor; an analog to digital converter; and a pressure sensor.

Any of the pressure sensors may comprise a silicon pressure sensor formed from an ultrathin spiral shape layer of monocrystalline silicon.

Any of the pressure sensors may comprise a layer of silicon positioned between a top polymer layer and a bottom polymer layer.

Any of the medical devices may further comprise a magnetic inductive loop antenna configured to wirelessly interface with an external reader antenna. The external reader antenna may be embedded in an external reader antenna substrate. The external reader substrate may be a sheet, a mattress cover, or a mattress surface.

Each biologically interactive device may have: a footprint that is less than or equal to 25 $cm^2$; and a thickness that is less than or equal to 1 cm.

Any of the medical devices may have: a temperature precision of at least 0.1° C.; a thermal mass density that is less than that of skin and less than 75 $\mu J/mm^2/K$; and/or a thermal equilibrium response time that is less than or equal to 3 seconds.

Any of the medical devices may be described in terms of a thickness, flexibility, elasticity and mass, including values selected to achieve conformal contract with an underlying skin surface and to ensure the device is relatively comfortable and unobtrusive to a person being monitored. For example, the thickness of the entire device may be less than 1 cm, less than 5 mm, or less than 1 mm. The thickness of the sensor itself may be described as thin, with a thickness less than 1 mm, less than 100 $\mu m$. The associated sensor components may be arranged as multiple independent stacked layers, including with active components such as sensing, wireless transmission, wireless power, wireless control, embedded in flexible layers, such as elastomeric or polymeric materials that are sufficiently soft and flexible to provide conformal contact with the underlying biological material, such as skin.

The device may be described as having a bulk flexibility or modulus that is matched to skin so that forces commonly exerted on the skin and resultant skin deformation, are similarly accommodated by a deformation of the device that is positioned on the skin. Exemplary flexibility ranges may be described in terms of a net bending stiffness less than or equal to 1 nN m. Exemplary stretchability ranges may be described in terms of a bulk device modulus, such as a Young's modulus, that is less than or equal to 1 MPa, less than 500 kPa, less than 100 kPa, between 1 kPa and 250 kPa, or any sub-ranges thereof.

Any of the medical devices and methods may be described as having a duration of conformal contact that is for a user time period that is between 1 minute and 1 day.

Any of the medical devices may have a biologically interactive device that is multifunctional and measures at least temperature and pressure.

Any of the medical devices may have a biologically interactive device that measures at least one additional parameter selected from the group consisting of: oxygen level, electric potential, heart rate, respiration rate, hypovolemia, and optical signal.

The medical devices provided herein are compatible with a range of applications. For example, any of the medical devices may be used for a medical application selected from the group consisting of: health evaluation; sleep evaluation; ulcer risk mitigation; sudden infant death syndrome warning; hyperthermia and hypothermia.

The medical devices may be used for full-body spatio-temporal mapping of the physiological parameter over a skin surface area.

The medical devices may be used on a skin surface area corresponding to a human, a cow, a horse, a pig, a bird, a dog, a cat, a rodent, or a sea animal.

The medical device may be further characterized in terms of a functional parameter such as a sensitivity or resolution, including with respect to the surface area of skin over which the device spans. For example, a number of individual biologically interactive devices are selected and spatially positioned so as to provide an average physiological parameter spatial resolution at least as good as 5 cm over the entire surface area that is being monitored. Depending on the application of interest, the monitored surface area may range from between whole body surface to a small fraction thereof. For example, evaluation of blood flow to an extremity may focus on the extremity area only. Electrical monitoring may focus on the chest area overlying the heart. For those applications over a confined skin area, the spatial resolution may be correspondingly higher, including at least as good as 1 cm. The monitored surface area may correspond to at least 25%, at least 50%, or at least 75% of the entire surface area, for large area applications.

The medical device is scalable to any desired range, including for applications requiring relatively small areas such as for a small animal or for localized measurement, up to large areas for large animals or whole body assessment. The medical device may be described as having a device footprint, corresponding for example to the size defined by the area contained within a perimeter of the outermost sensors. The device footprint may be described as being greater than or equal to 10 cm$^2$ and less than or equal to 20 m$^2$, and any subranges thereof. Depending on spatial resolution, the individual biologically interactive devices may have a spatial density of between 1 per mm$^2$ and 1 per 100 cm$^2$. The spatial density may be uniform over the entire footprint, or may spatially vary, with regions of relatively high density and regions of relatively low density.

Any of the medical devices may further comprising an alert or an alarm configured to signal a warning condition for a measured or a calculated physiological parameter that is outside a user-selected safe value. For example, for skin ulcer prevention applications, a force or pressure on an area of the body that is above a user-selected safe value for a certain time period may result in an alert or alarm so that a caregiver may take appropriate action, such as moving the patient so as to avoid bed-sores and resultant skin ulceration.

Any of the medical devices provided herein may be battery-free:

Also provided herein is a method of monitoring a physiological parameter using any of the medical devices provided herein.

The method may comprising the steps of: interfacing a plurality of spatially distributed biologically interactive devices with a body surface; detecting a physiological parameter with a sensor in each of the plurality of spatially distributed biologically interactive devices; wirelessly transmitting the detected physiological parameter to a receiver; generating a spatial distribution map of the detected physiological parameter across the interfaced body surface; thereby monitoring the physiological parameter.

The method may further comprising the step of periodically repeating the interfacing step to obtain temporal information for the spatial map, thereby generating a spatio-temporal distribution map of the detected physiological parameter.

The sensor may be a pressure sensor for evaluating risk of a skin-ulcer in a patient positioned on a bed.

The sensor may be a temperature sensor for a sleep study.

The method may be for a body surface that corresponds to at least 30%, at least 50%, or at least 80% of a whole-animal body surface area.

The wireless power system may provide a power delivery of at least $1 \times 10^{-4}$ mW/cm$^2$. The wireless power system may have a power efficiency defined as power delivered to power harvested that is greater than or equal to 0.1%, including greater than or equal to 50%. The wireless power system may comprise a large area antenna for the wireless power harvesting. The large area antenna may have a circumference that is greater than or equal to 100 cm.

The medical device may further comprise a small area antennae for NFC control. The small area antennae may have a circumferential footprint that is less than or equal to 10 cm. The small area antennae may comprise a coil.

Any of the medical devices may further comprise a near field communication chip to provide wireless power delivery to the sensors and wireless data communication between the biologically interactive devices and the wireless controller.

Any of the medical devices may have a wireless transmission and receipt range that is greater than or equal to 10 cm.

In addition to the demonstrated capabilities in sensing (and other modes of sensing), actuators can be integrated with the sensors, including in a single device platform or in separate collections, to provide feedback to patients who are at risk for pressure-induced ulcers, bed sores, and the like, as a specific example. The power requirements of the actuators may result in the use of local storage capabilities, i.e. supercapacitors or batteries, that can be charged continuously via wireless power delivery.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 1A. Illustration of a collection of thin, conformable skin-mounted sensors across the body, with continuous, wireless transmission of temperature and pressure data in a time multiplexed fashion. FIG. 1B. Top-view image (scale bar: 8 mm) of a representative sensor. FIG. 1C. Exploded view schematic illustration of device structure. FIG. 1D. Illustration of 65 wireless sensors mounted across the entire body, with corresponding images of devices at representative locations. FIG. 1E. Images of sensors at different locations on the front and back sides of the body. FIG. 1F. Image of a collection of 65 sensors (scale bar: 16 mm).

FIGS. 2A-2H. Characterization of the physical properties and measurement responses of sensors for certain applications. FIG. 2A. IR image of several sensors on the forearm. The results indicate that the presence of the sensors does not significantly alter the temperature of the skin. FIG. 2B. Measured and computed temporal responses of devices constructed with different thicknesses of an insulating elastomeric support, with enlarged view (right) of a region highlighted by the red dashed box (left). FIG. 2C. Picture of a device mounted on the upper lip beneath the nose. FIG. 2D. Temperature fluctuation wirelessly recorded (sampling rate: 6 Hz) with this device, with enlarged view (right) of a region highlighted by the red dashed box (left). Cycles of inhalation and exhalation are clearly evident. FIG. 2E. Images of a sensor mounted on left forearm (left) and pressed with a fingertip (right). The inset shows a magnified view to highlight the robust, conformal contact with the skin. FIG. 2F. Equivalent circuit diagram of the pressure sensing part of the device. FIG. 2G. Temperature fluctuation wirelessly recorded (sampling rate: 6 Hz) with a device on the left forearm during application of various forces with the fingertip (poking, touch and holding). The frame on the right corresponds to the holding box on the left, with inset image (scale bar: 4 cm). FIG. 2H. Schematic diagram of the mechanics, and FEA results for the maximum principal strain across the spiral shaped thin silicon pressure sensor. Computations for an applied force of 10 kPa suggest a gauge factor of ~50.

FIGS. 3A-3G. Electromagnetic considerations in operating range and area coverage for certain applications. FIG. 3A. Sequence of images that show short-range readout using a conventional smartphone. FIG. 3B. Image of dual-antenna system configured for full-body readout on a mattress, with inset of a subject lying on top of a ~5 cm thick pad that covers the antennas. (27 ages, male, 90 kg) FIG. 3C. Diagram of use of such a system for time-multiplexed readout of a large collection of wireless sensors. FIG. 3D. Graph or spatial map of experimental measurements of operating range for an antenna (yellow square in the x-y plane) with dimensions of 800×580×400 mm, at RF powers of 4, 8, and 12 W. FIG. 3E. Computed magnetic field strength as a function of vertical distance (z) away from the x-y plane at various RF powers. Magnetic field distribution in XZ-plane (FIG. 3F) and YZ-plane (FIG. 3G).

FIGS. 4A-4I. Wireless, full-body thermography in a clinical sleep laboratory. FIG. 4A. Diagram of the locations of 65 sensors in an embodiment. FIG. 4B. Picture of the bed in the sleep lab, with a pair of readout antennas (red dashed lines) located underneath a soft pad on the mattress. FIG. 4C. Picture of a subject lying on the mattress. (27 ages, male) FIGS. 4D-4F. Graphs of temperature averaged over local body regions during the 7 hours of the study. The blue shaded sections indicate sleep. The black dotted boxes indicate important changes in temperature that occur 2~3 hours before waking. FIG. 4G. Maps of temperature distributions across the body, just before falling asleep, (FIG. 4H) 2 hours before he waking, and (FIG. 4I) shortly after waking.

FIGS. 5A-5K. Wireless, full-body pressure mapping in a hospital bed. FIGS. 5A-5B. Diagram of the locations of 29 sensors on the back side of the body and pictures of each body region with sensors. FIGS. 5C-5D. Picture of an angle-adjustable bed in a hospital, with dual antenna setup for continuous pressure monitoring (27 ages, male, and 90 kg) and in Carle hospital. FIGS. 5E-5F. Picture of a subject lying on the bed in the supine position 0°, and corresponding results of pressure measurements averaged over body region. FIGS. 5G-5H. Similar results for the supine position 60°. FIGS. 5I-5K. Maps or pressure distributions across the body in supine position 0°. (1000, 2000, and 3000 sec).

FIGS. 21A-21D. Corresponding spatial distribution map from results of FIGS. 19A-19H and 20A-20H at 120 min and 240 min, with interpolations in spatial regions between adjacent sensors.

DETAILED DESCRIPTION OF THE INVENTION

Figures 1A, 1B:
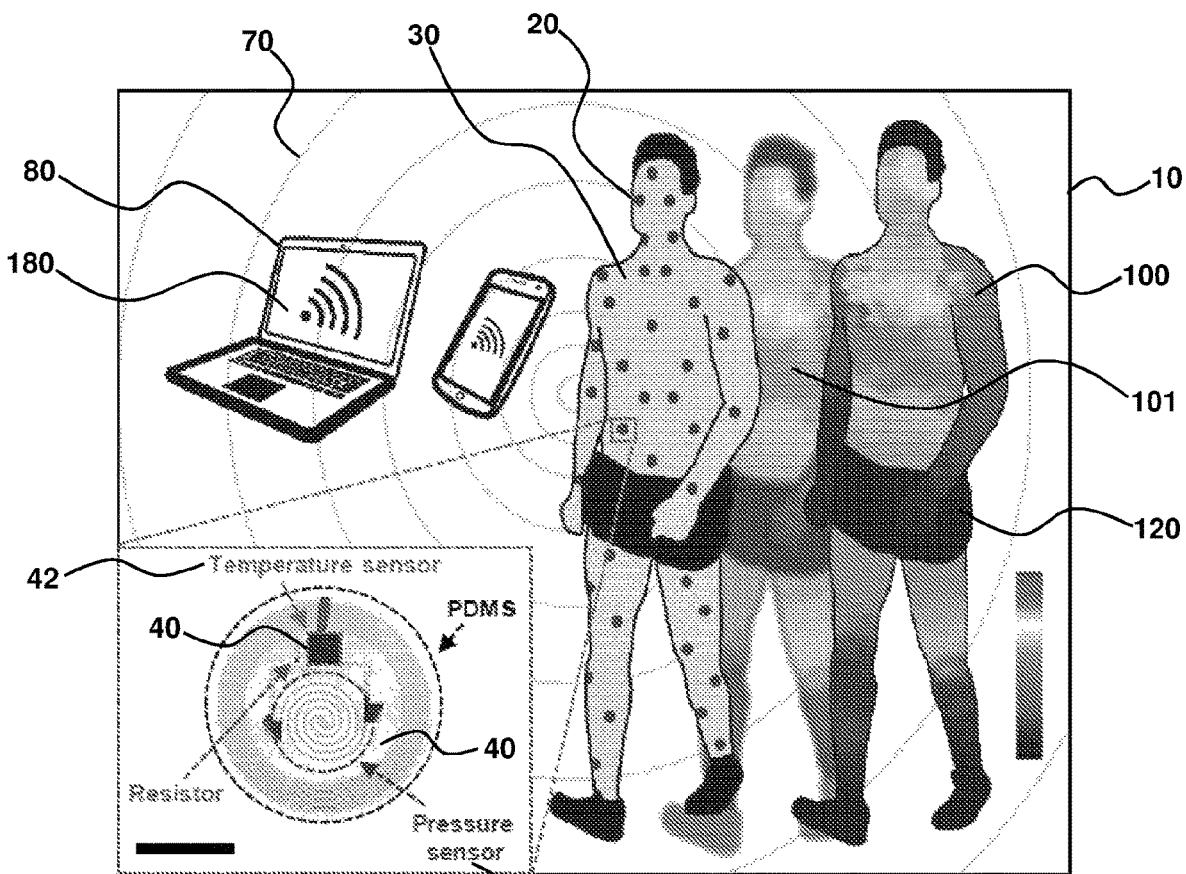
FIGS. 1A-1F. Illustrations, exploded view schematic diagrams and images of wireless, battery-free epidermal sensors of temperature and pressure, used in large-scale arrays for full-body monitoring.

In general, the terms and phrases used herein have their art-recognized meaning, which can be found by reference to standard texts, journal references and contexts known to those skilled in the art. The following definitions are provided to clarify their specific use in the context of the invention.

"Physiological parameter" refers to a measurable parameter that can have a biological impact, or that relates to a physiological process. For example, prolonged and/or high pressure exerted against skin can result in a range of unwanted biological outcomes, including in extreme cases, ulcers. This is particularly problematic for patients confined to the bed. Similarly, temperature monitoring can be useful in a range of applications, including sleep assessment and general monitoring. Physiological processes may have an effect on these parameters, including respiration on temperature measurements. External physical parameters may have an effect on these parameters, such as a tackle-generated force in a physical contact sport, injury in the field such as from a military or non-military setting, or onset of an infectious disease.

"Biologically interactive device" refers to a sensor or actuator of any of the devices described herein configured an position to interface with a biological surface, such as skin, so that one or more biological parameters can be measured by a sensor and/or one or more effects can be felt by the animal by activation of an actuator. The biologically interactive device is compatible for interfacing with a wide size range of biological surfaces, ranging from well-confined, localized regions, up to whole-body type interfacing, and any subset thereof. The interaction may be capable of being over a large area biological surface, with biologically interactive devices positioned to cover the large area. In this configuration, however, the interaction may be optionally focused to particular regions of the biological surface. For example, the chest-region may be of interest in monitoring electrical parameters indicative of heart condition. In other aspects, a more whole-body monitoring may be of interest, such as temperature measurements where core body temperature on the torso is measured to ensure proper overall body temperature and extremity temperature measured to avoid adverse state, such as frost-bite risk. In some applications, it is desired to monitor a physiological parameter over a large area biological surface.

"Large area biological surface" refers to the capability of any of the medical devices described herein that can be deployed to reliably monitor one or more physiological parameters over large areas of the body. The interconnection between a plurality of specially configured biologically interactive devices, along with the capacity to wirelessly communicate with the sensors, provides a unique platform for interfacing with large areas that is not practical for many conventional devices. "Large area" may be described in terms of the footprint of the device on the skin relative to the whole body, and may be greater than or equal to 10% and up to 90% or up to 100%, and any subranges thereof, depending on the application of interest. The total number of biologically interactive devices is determined by the total surface area being monitored and desired spatial resolution. Those variables are, in turn, dependent on the application of interest. If total body monitoring is desired, then the total surface area footprint of the device will approach the total surface area of the individual. Similarly, if only a portion of the skin surface area is of interest, the device can be configured to have a similar footprint area size and spatial distribution of the interactive devices.

"Sensor" refers to a device component useful as a sensor and/or useful for detecting the presence, absence, amount, magnitude or intensity of a physical property, object, radiation and/or chemical. Sensors in some embodiments function to transduce a biological signal into an electrical signal, optical signal, wireless signal, acoustic signal, etc. Useful sensing elements include, but are not limited to electrode elements, chemical or biological sensor elements, pH sensors, optical sensors, photodiodes, temperature sensors, capacitive sensors strain sensors, acceleration sensors, movement sensors, displacement sensors, pressure sensors, acoustic sensors or combinations of these. Particularly useful sensors are those that measure pressure (or force, such as by the equation Pressure=Force divided by the area over which the force is measured, so that a measure of one of pressure or force allows the other to be calculated, with the area generally corresponding to the sensor area) or temperature. The devices described herein may be multi-modal, with multiple different sensor types to provide simultaneous measure of multiple different physiological parameters, such as temperature and pressure.

"Actuator" refers to a device component useful for interacting with, stimulating, controlling, or otherwise affecting an external structure, material or fluid, for example a biological tissue. Useful actuating elements of the actuator include, but are not limited to, electrode elements, electromagnetic radiation emitting elements, light emitting diodes, lasers, magnets in an oscillating magnetic field, chemical or biological release agents, and heating elements. Actuators include electrodes for providing a voltage or current to a tissue, heaters for providing heat to a tissue, mechanical actuators for generating force or pressure to a tissue. Actuators may include sources of electromagnetic radiation for providing electromagnetic radiation to a tissue. Actuators include thermal sources for heating tissue. Actuators include displacement sources for displacing or otherwise moving a tissue.

"Wireless controller" refers to electronic components, including chips, that provide for wireless control of the sensors or actuators. Similarly, "wirelessly transmitter" refers to electronic components, including chips, for transmitting data to an external reader. An example of such wireless components is a near field communication (NFC) chip, including NFC chips from Texas Instruments. NFC is a radio technology enabling bi-directional short range wireless communication between devices. In this manner, a controller external to the actuator device (e.g., off-circuit) can be used to provide actuator control and to receive information from the actuator device, including device status or information from one or more on-circuit sensors.

"Power harvesting" refers to a process by which energy is derived from an external source and, thereby, may avoid the need for relatively large, bulky and expensive primary or secondary battery systems. Of course, the devices provided herein may be compatible with batteries, depending on the application of interest. For example, relatively heavy or bulky systems may be incorporated into clothing, shoes, hats, gloves, scarves, face masks, and the like, in a manner that would be unobtrusive, or minimally noticeable, to a user.

In this fashion, any of the devices provided herein are capable of "wirelessly operation", without a need for hard-wiring to a receiver for control, powering, transmitting or communication.

"Spatio-temporal" refers to the measurement of a parameter with respect to location and time. In particular, the parameter can vary with position on a skin surface and, at a particularly location, with time. Assembly of the time-varying maps results in a "spatio-temporal map".

"Full-body surface" refers to coverage that generally assesses physiological parameters over the majority of the body. Practically, it does not mean that every individual location of the body surface is monitored, but rather that the biologically interactive devices are spaced and distributed over the body to provide useful whole-body information. For example, the devices may be provided on the various extremities and torso to provide a good assessment of the full body. For applications where the head and neck are important, devices may also be placed on the head, face and neck. As desired, the positions between sensors that are not directly measured, may have a calculated parameter value based on interpolation between near and adjacent sensors.

"Adjacent" to the biological surface or to the skin refers to positioning the device so that the sensor may reliably measure a physiological parameter associated with the underlying biological material. The sensor may measure a parameter of interest on the skin or beneath the skin, such as blood flow, oxygen level, temperature, pressure, optical parameter, tissue stiffness, moisture level, or the like. Accordingly, a device may be considered adjacent if it is directly mounted to the surface, or has an intervening layer, including an adhesive and/or barrier layer, so long as the functionality of the actuator or sensor is maintained. Adjacent may also be described as within 1 mm, 500 µm, 100 µm, 10 µm or 1 µm of the skin surface.

"Operably connected" refers to a configuration of elements, wherein an action or reaction of one element affects another element, but in a manner that preserves each element's functionality. For example, a wireless controller such as an NFC chip operably connected to a sensor refers to the ability to power the sensor and communicate with an external data reader without impacting the functionality of the sensor.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. As used herein, many stretchable structures are also flexible. Some stretchable structures (e.g., device components) are engineered to be able to undergo compression, elongation and/or twisting so as to be able to deform without fracturing. Stretchable structures include thin film structures comprising stretchable materials, such as elastomers; bent structures capable of elongation, compression and/or twisting motion; and structures having an island—bridge geometry. Stretchable device components include structures having stretchable interconnects, such as stretchable electrical interconnects. As used herein, for embodiments where the devices are mounted directly to the skin, the devices may be characterized as stretchable, including stretchable and flexible so as to achieve good conformal contact with underlying skin, if desired. "Conformable" refers to a device, material or substrate which has a bending stiffness sufficiently low and elasticity sufficiently high to allow the device, material or substrate to adopt a desired contour profile, including a contour profile that may change over time, for example a contour profile allowing for conformal contact with a surface having a pattern of relief or recessed features, or. In certain embodiments, a desired contour profile is that of a tissue in a biological environment, for example skin or the epidermal layer.

Thin, soft, skin-like electronic devices with wireless, near field communication (NFC) capabilities offer simple and optionally battery-free platforms with versatile functional possibilities of relevance to continuous monitoring of physiological health as well as controlled sensory actuation. Application possibilities range from those in hospital care and clinical medicine, to physical rehabilitation, fitness/wellness tracking, awareness and cognitive state assessment, and human-machine interfaces.

Although deployment of an individual device of this type onto a targeted region of the body offers interesting opportunities and several clinically validated measurement modalities, time-multiplexed addressing of large-scale wireless networks composed of a multitude of separate devices distributed at many different locations across the body could qualitatively expand the possibilities. The devices and methods provided herein achieve this mode of operation, in which NFC power delivery and data communication to a central acquisition/control system occurs with long-range readers, and rapid scanning through a large-scale collection of devices mounted on the body, to provide continuous streams of data that can be assembled into spatio-temporal maps of physiological processes. The result enables full-body coverage in settings of practical importance, including from hospital beds to wheelchairs to office desks. The applications are wide, including for monitoring of infants in cribs (e.g., SIDS), to understanding of force distributions in athletics (e.g., evaluating sports gear, padding, helmets, equipment).

Specific embodiments introduced here involve advanced, skin-like devices designed to precisely measure local physiological parameters, such as pressure and temperature. The efficacy and accuracy of the devices provided herein is quantitatively validated through computational modeling and comparison to experimental controls. Simultaneous wireless operation of such devices laminated onto the skin at distinct sites across the limbs, torso, neck and head illustrate the possibilities, where single or multiple large-scale loop antennas interfaced to RF power delivery and data acquisition electronics allow multiplexed operation with a range of tens of centimeters to meters. Demonstrations of this technology include tests on several human subjects, with a focus on tracking of sleep patterns in a clinical laboratory, and monitoring of pressure distributions relevant to formation of ulcers in patients confined to hospital beds. Further specific embodiments involve skin-like devices designed to be incorporated into human-machine interfaces, such as virtual reality systems, and/or controlled sensory actuation, including remote actuation of one or more senses.

Example 1: Large-Scale Distributed Arrays of Wireless, Epidermal Sensors for Full-Body Spatio-Temporal Mapping of Temperature and Pressure FIG. 1A presents a conceptual schematic illustration of a medical device. Here, 65 wireless, epidermal NFC devices mounted on the skin at locations across the human body, to enable monitoring of one or more physiological parameters of interest in real time, using a time-multiplexed, wireless scheme and a single reader antenna. Based on the known locations of the devices, time-dependent data captured in this manner can be rendered as spatio-temporal color plots mapped onto the body shape, also referred herein as spatio-temporal maps. FIG. 1B is a schematic image of a representative device. The component highlighted with the red dotted line (labeled "temperature sensor") corresponds to a small-scale, unpackaged integrated circuit chip that provides the NFC communication capability, along with sub-systems for wireless energy harvesting, temperature sensing and analog-to-digital (A/D) conversion (e.g., ams AG; NFC die SL13A, 100 μm thick, 2.38×2.38 mm). The part encompassed by the blue dotted line (labeled pressure sensor) is a pressure sensor that relies on the piezoresistive response of an ultrathin layer of monocrystalline silicon patterned into a spiral shape (diameter; 6.6 mm, width; 250 μm), as described in detail subsequently. The element indicated with the green dotted line (labeled resistor) is a simple resistor (0.6×0.3×0.3 mm) selected to ensure that the response of the pressure sensors falls into a range compatible with the A/D converter.

Figure 1C:
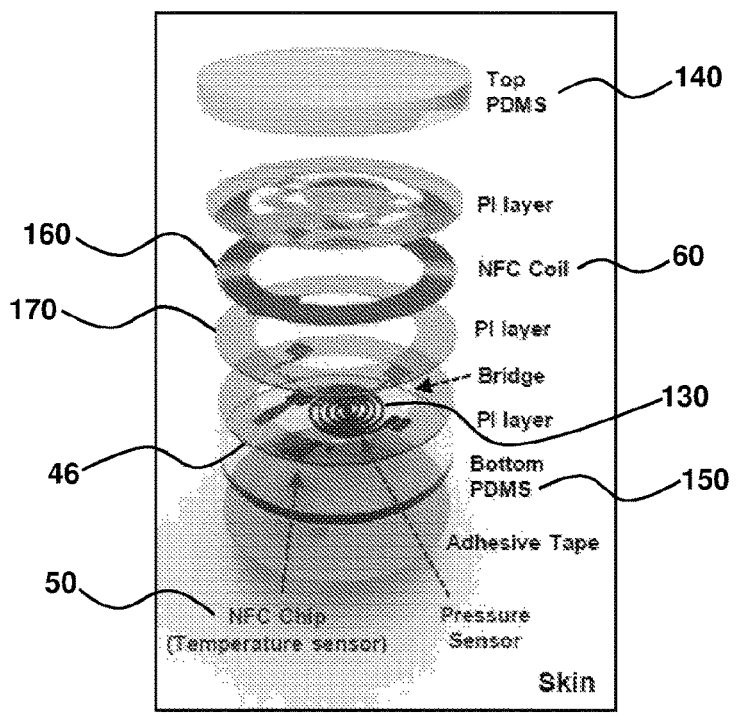
Figure 1D:
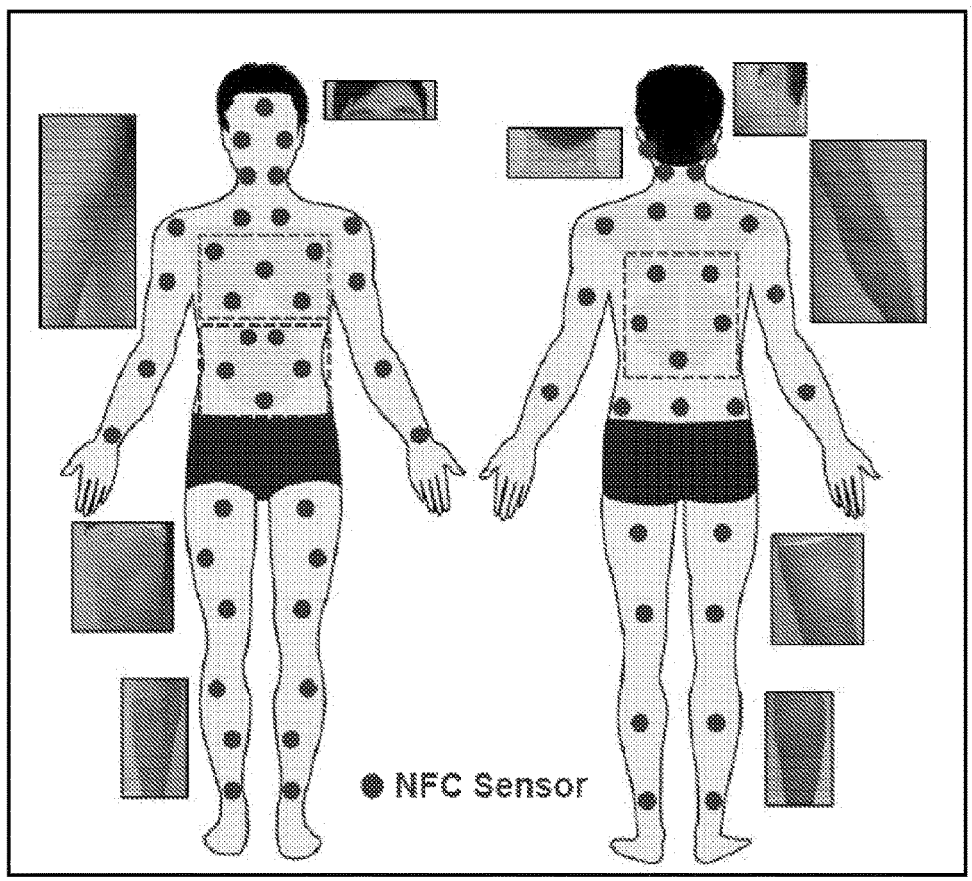
Figure 1E:
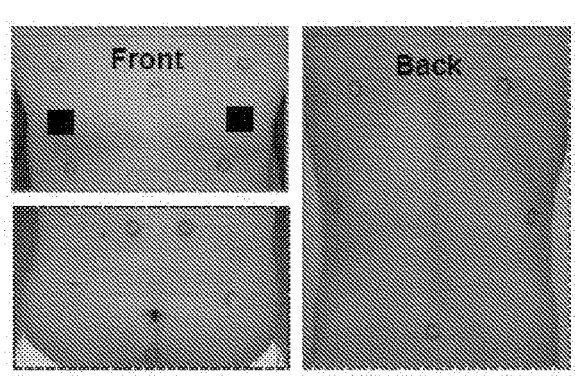
Figure 1F:
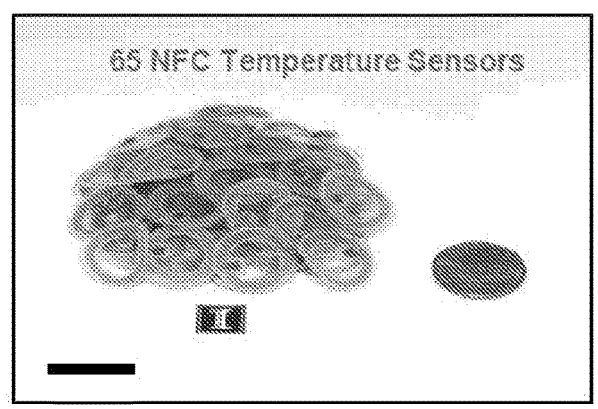

A detailed, exploded view schematic illustration in FIG. 1C presents the layout of these components, their interconnections with one another and their integration with a magnetic inductive loop antenna that serves as a wireless interface to an external reader antenna. The construction involves a multilayer stack of 1) an NFC chip, loop antenna (Cu, ~5 μm thick, diameter: 16 mm, width: 75 μm), and silicon pressure sensor, 2) thin films of polyimide (PI, e.g., Microsystem, USA, ~1.2 μm thick) as electrical insulators, 3) an overcoat and base of polydimethylsiloxane (PDMS, e.g., Sylgard® 184, Dow Corning; mixed at a 30:1 ratio of base to curing agent by weight, ~1 MPa) as encapsulating coatings, and 4) a biocompatible, skin-adhesive (Scapa, e.g., Scapa Health Care, thickness; ~50 μm thick, low modulus; ~17 kPa). The overall soft, deformable construction affords skin-compatible mechanics. The thin geometry of the PDMS base (~50 μm thick) minimizes the thermal equilibrium time of the temperature sensor with the skin. A hole in the tape that is aligned to the temperature sensor provides additional advantage in this sense. The PDMS overcoat is comparatively thick (50~300 μm) to provide robust, physical protection from the environment. Details of the designs and the assembly steps appear in supplementary note 1-2. The fabrication process is robust in that many devices can be created easily, at high yield (90%). FIGS. 1D-1F present schematic illustrations and photographs of a large collection of devices (blue dots) positioned for full-body coverage, on the front and back sides. FIG. 1F shows a stack of 65 devices with a penny to help illustrate size scale.

Fundamental characteristics of skin-like wireless temperature and pressure sensors: FIGS. 2A-2H summarizes results of experimental measurements and computational modeling of key device characteristics in an embodiment. The properties of the temperature sensor can be defined by 1) the accuracy and precision of the measurement, 2) the effective thermal mass of the overall device 3) the response time. Following a simple calibration procedure (supplementary note 3 and FIGS. 6A-6D), wireless recordings under controlled conditions (FIGS. 7A-7B) at a sampling rate of a few Hz match those obtained at the same location using an infrared (IR) camera (e.g., FLIR SC645, sensitivity: 0.05° C.) with differences of less than 0.04° C., thereby defining the precision of the measurement. Even during temperature transients (FIGS. 8A-8G) the data captured in these two ways are similar, to within an average of about ±0.1° C., likely limited in part by an inability to perfectly align the location and timing of the two sets of measurements.

The thermal mass is an important parameter that influences the time response and determines the magnitude of any perturbations to the natural skin temperature associated with the presence of the device. The overall area of a typical device is ~214 mm2. In a spatially averaged sense, the materials include 10 μg/mm2 of Cu (heat capacity, C=386 J·kg-1·K-1 and density, p=8920 kg·m-3), 340 μg/mm2 of PDMS (C=1380 J·kg-1·K-1, p=970 kg·m-3), 3 μg/mm2 of PI (C=1090 J·kg-1·K-1, ρ=1490 kg·m-3) and 6 μg/mm² of Si (heat capacity c=710 J·kg$^{-1}$·K$^{-1}$, ρ=2330 kg·m$^{-3}$). The calculated thermal mass per unit area of Cu, PDMS, PI, and Si are 0.4 μJ·mm$^{-2}$·K$^{-1}$, 46.9 μJ·mm$^{-2}$·K$^{-1}$, 0.4 ρJ·mm$^{-2}$·K$^{-1}$ and 0.4 ρJ·mm$^{-2}$·K$^{-1}$, respectively. The total thermal mass per unit area of the device is, therefore, 48.1 μJ·mm$^{-2}$·K$^{-1}$. Although this number is considerably higher than that associated with previously reported, wired epidermal temperature sensors, it is lower than that of the skin itself (heat capacity, C=3391 J·kg$^{-1}$·K$^{-1}$, density, ρ=1109 kg·m$^{-3}$ (see, e.g., www.itis.ethz.ch/virtual-population/tissue-properties/database/heat-capacity/), and thickness=1 mm yields a thermal mass of ~380 μJ·mm$^{-2}$·K$^{-1}$). As a result, the presence of the device does not change significantly the natural temperature of the skin in the mounting location or in nearby regions, as confirmed by the thermal images of FIG. 2A, under normal conditions of relevance to those of the human clinical trials described herein.

This relatively small thermal mass and the overall construction also yield a response time that is only limited by the dynamics of thermal diffusion from the skin, through the base PDMS and into the embedded temperature sensor in the NFC chip. As shown in FIG. 2A, a sensor cooled to 23° C. placed on the ventral side of the right forearm can be used to quantify the thermal equilibrium time as a function of a representative design characteristic, i.e. the thickness of the base PDMS. The results show that for thicknesses of 50, 100 and 200 μm, the equilibration times are 0.8, 1.5 and 2.5 s, as determined by wireless data acquisition at a sampling rate of 25 Hz. These results are consistent with those determined by finite element analysis (FEA, supplementary note 5) and theory (supplementary note 6), as shown in FIG. 2B and FIGS. 9A-9E, and they afford capabilities in capture of thermal transients relevant to most naturally occurring body processes, including respiration. A simple demonstration of this possibility involves mounting a device onto the skin of the upper lip, with the sensing region aligned to the base of the nostril. Results captured at a sampling rate of 6 Hz in an ambient laboratory environment show cyclical variations in temperature from 35.5° C. (during exhalation) to 35.1° C. (during inhalation), time synchronized with respiration at 4 breaths per 10 seconds.

Figure 10A:
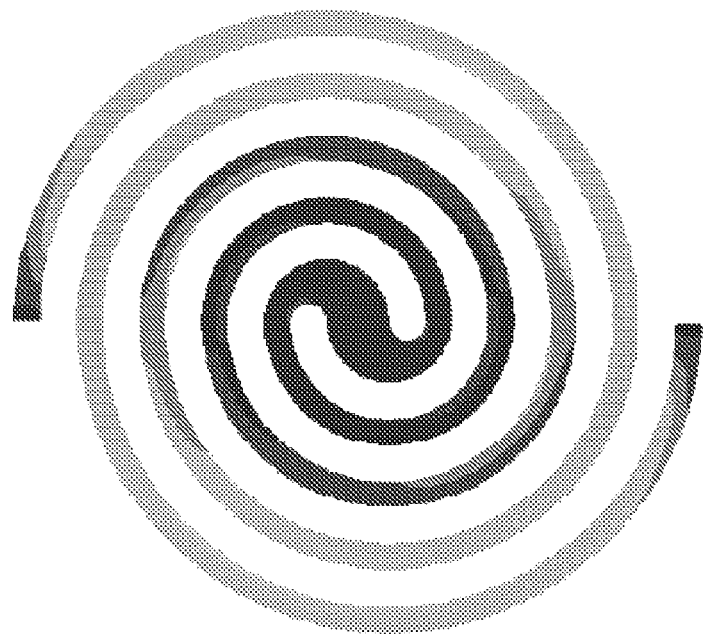
FIGS. 10A-10B schematic illustration of a pressure sensor having a circle design (FIG. 10A) and line design (FIG. 10B) with resultant maximum principle strains illustrating the benefits of the circle design.
Figure 10B:
Figure 11A:
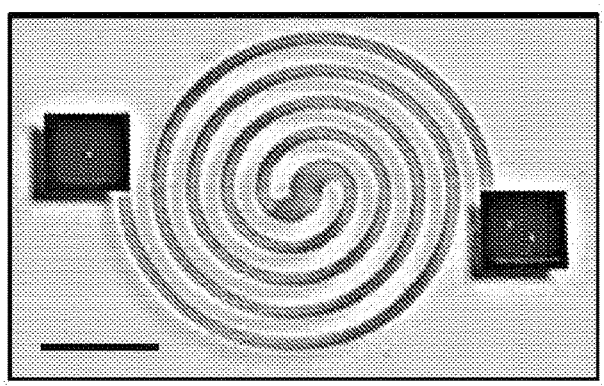
FIGS. 11A-11F. Characterization of circle or spiral pressure sensor.
Figure 11B:
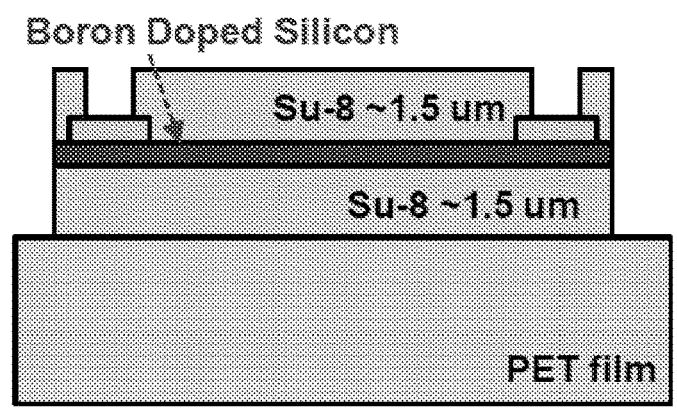

The pressure sensor provides additional, simultaneous measurement functionality in the same device platform. Here, a spiral structure constructed from a thin, monocrystalline membrane of silicon (details in FIGS. 11A-11B) serves as the pressure sensing element. The spiral shape facilitates stable operation on the surface of the skin, due to enhanced uniformity in pressure-induced distributions in strain compared to that associated with simple, linear designs (FIGS. 10A-10B). FIG. 2H shows results computed by FEA for the cases with and without a layer of PET (5 μm, modulus ~5 GPa) under an applied pressure of 10 kPa. The PET limits the stretching and thereby reduces the magnitude of the response and enhances the uniformity of the pressure distribution, thereby illustrating a simple means for adjusting the range of sensitivity through device design. The resistance of a spiral (R1) with an unperturbed resistance of R0 as a function of pressure can be approximated with an effective gauge factor (G), according to $$R_1 = R_0(1 + G\varepsilon)$$

Here, the average strain along the silicon, ε, corresponds to results of 3D-FEA for 10 kPa pressure shown in FIG. 2H. The computed value of G with R0=29.3 kΩ is in the range of ~50, comparable to values expected for boron doped silicon.

Figure 2E:
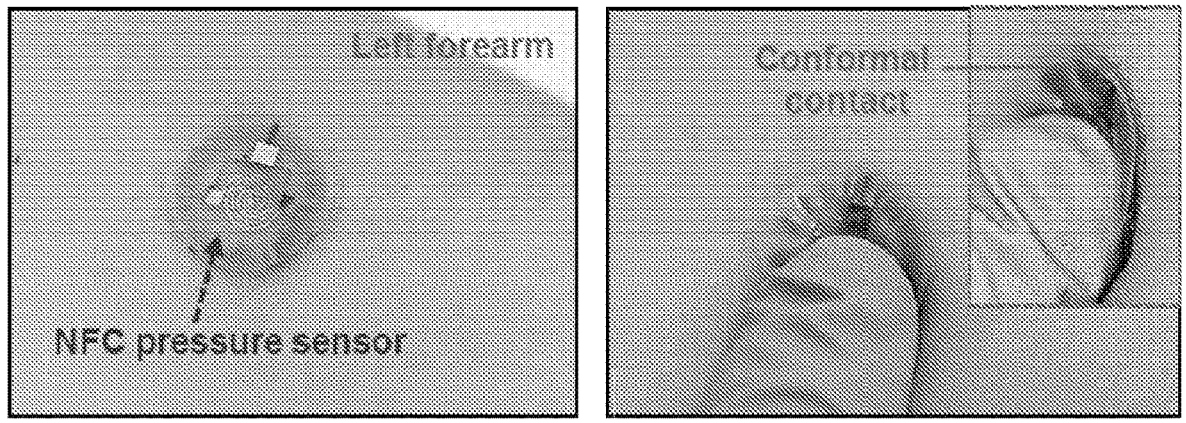
Figure 2F:
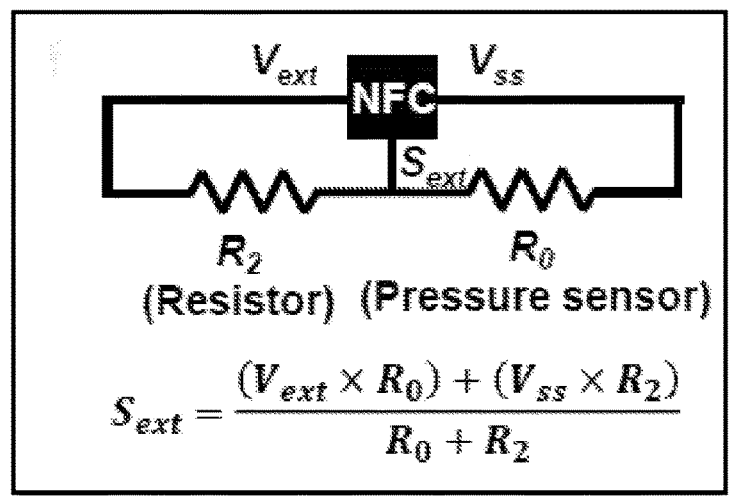

In a typical case, a simple empirical calibration procedure defines the connection between wireless measurements from a device and the actual pressure. Here, the PDMS layers protect the device, while allowing soft, conformal contact to the skin, as illustrated in FIG. 2E for the case of the left forearm. A voltage divider relationship, illustrated in FIG. 2F, converts the change in resistance associated with the response of the pressure sensor into a voltage output for analog input to the A/D converter, via the internally rectified output voltage of the NFC chip (Vext), a negative supply or ground of the chip (Vss), the analog input of the chip (Sext), an external tuning resistor (R2), and the pressure sensor (R0), according to:

$$S_{ext} = \frac{(V_{ext} \times R_0) + (V_{SS} \times R_2)}{R_0 + R_2}$$

Due to the design of the NFC chip used here, the analog input ($S_{ext}$) to the A/D converter must lie between 0.3V to 0.6V. Proper selection of the tuning resistor ($R_2$) ensures this condition for an operating range of interest. Applications that involve relatively small (FIG. 2G) and large (FIGS. 5A-5K) pressures may require devices with different resistors. For a given design, calibration procedures explained in the supplementary note 4 afford accurate measurement capabilities across a given range of pressures.

To illustrate operation, pressure applied to a medical device mounted on left forearm via finger poking, touching, and holding yield qualitatively expected results, with negligible hysteresis and fast response time. The enlarged box shows the response under continuous pressure (holding). The device in this case had $R_0$=29.3 kΩ and $R_2$=220 kΩ, as noted in FIG. 2F. The measured voltage range (0.4~0.6 V), and corresponding resistance change (FIG. 11C, ΔR/R: ~1.2%) corresponds to a pressure range of ~6 kPa. (poking: ~6 kPa, touching: ~3.2 kPa, and holding: ~4.1 kPa).

Figure 3A:
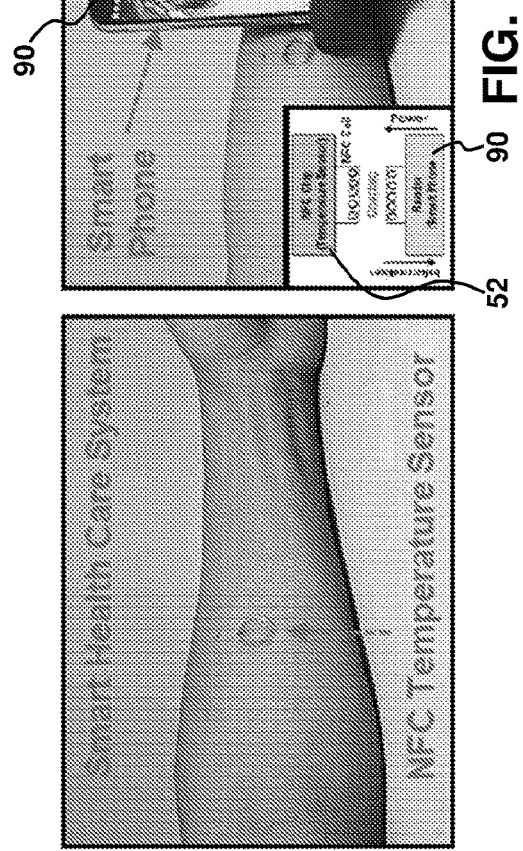
Figure 3C:
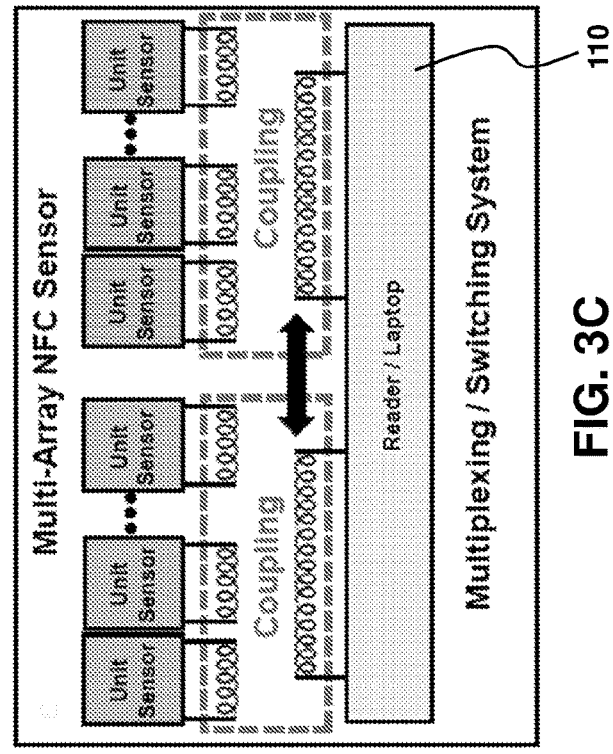
Figure 3B:
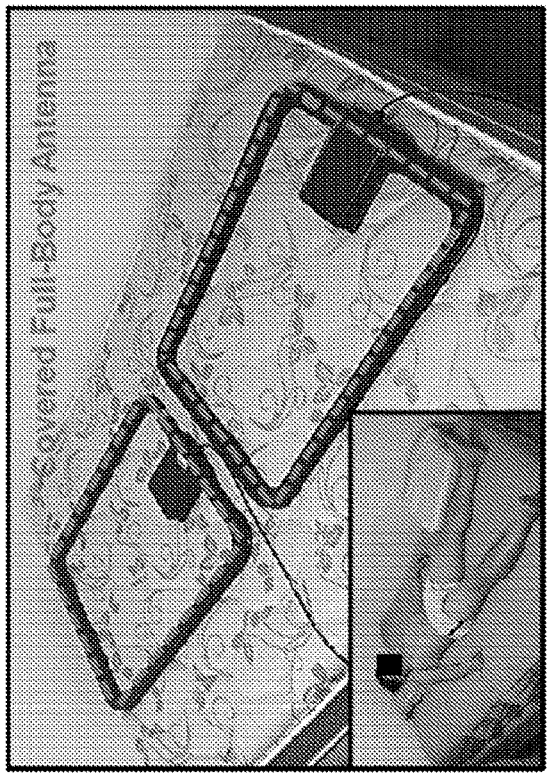
Figures 13, 14:
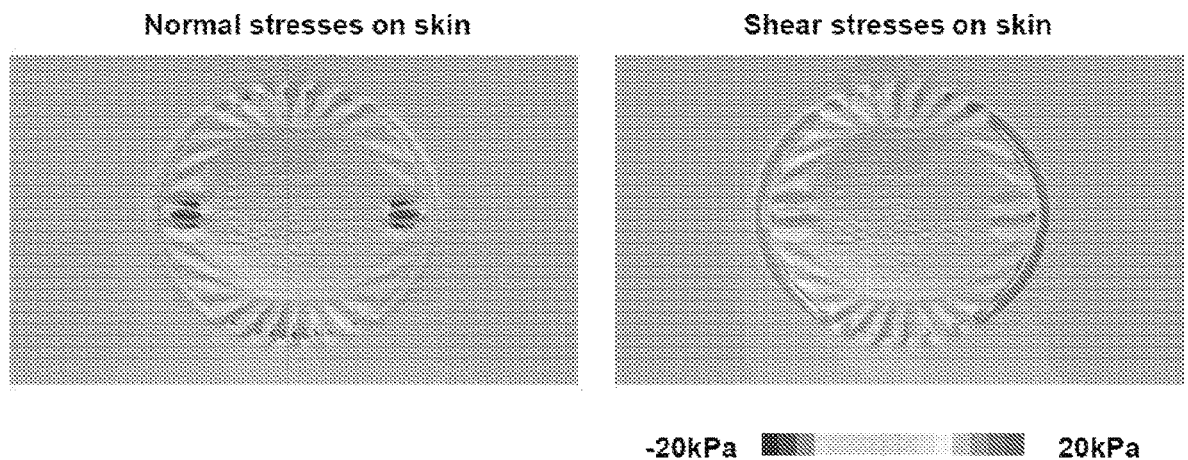
FIG. 13. Illustration indicating that for an applied strain on the device, the corresponding stress on the skin is within normal skin sensitivity so that the patient does not feel the device.
FIG. 14. Demonstration using a standard smartphone as a reader of the medical device operating over a distance from the device in the range of less than 10 cm.
Figure 15A:
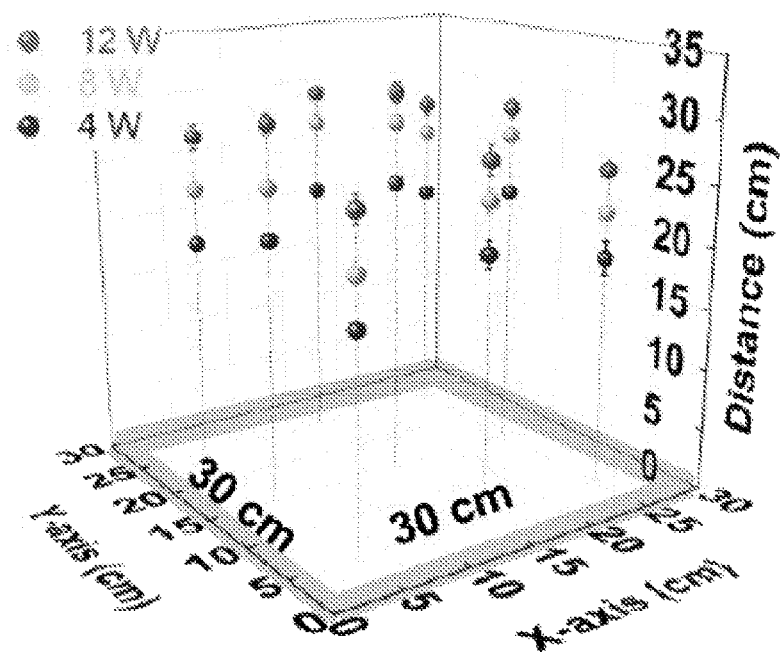
FIGS. 15A-15D. Impact of power level on communication distance.
Figure 15B:
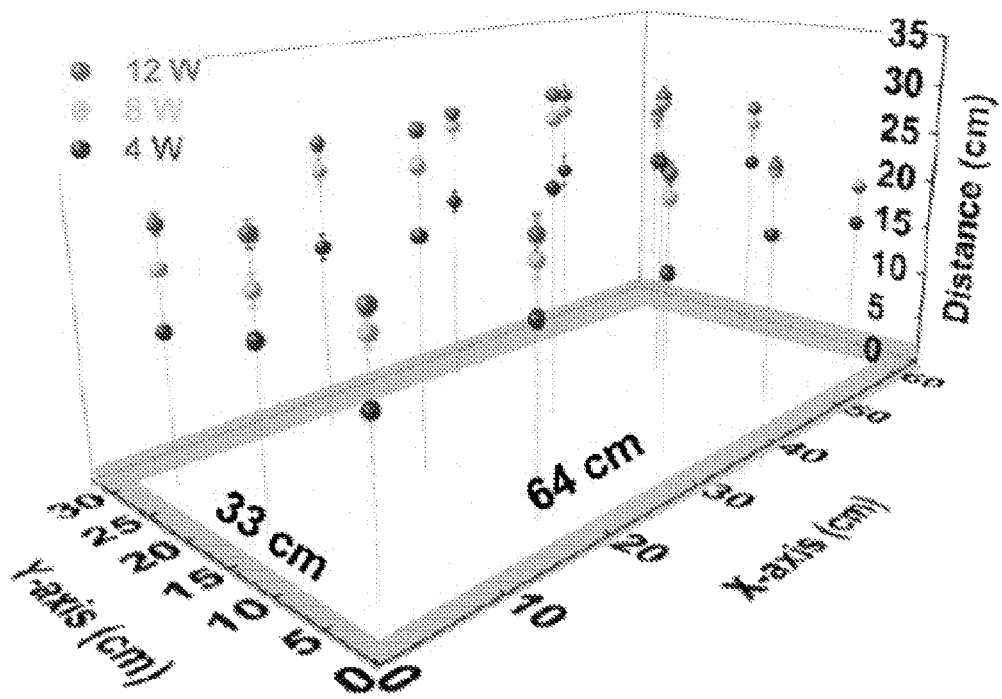
Figure 15C:
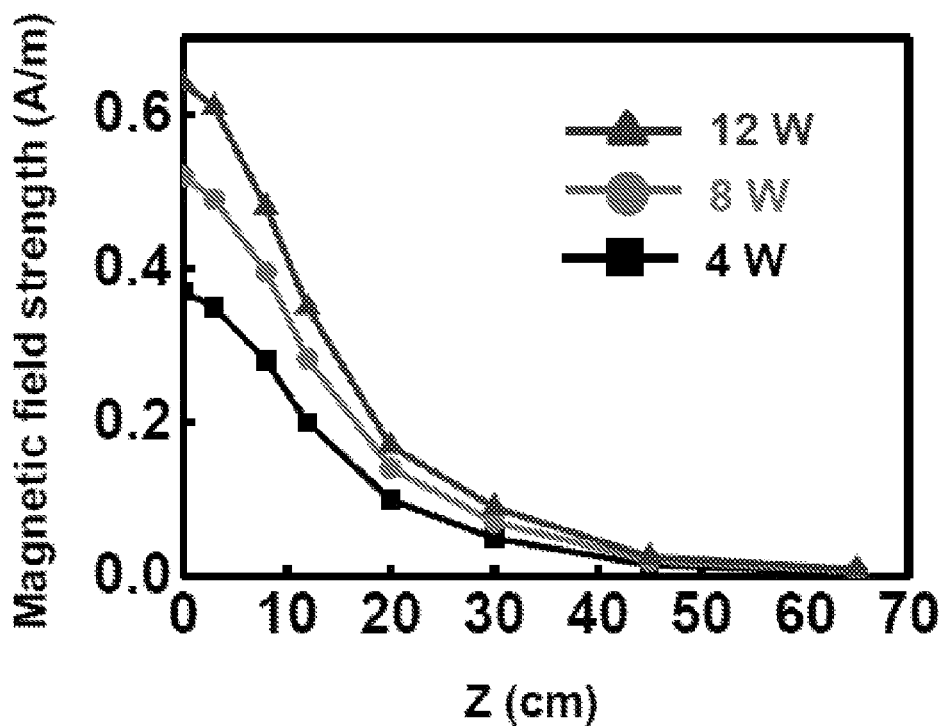
Figure 15D:
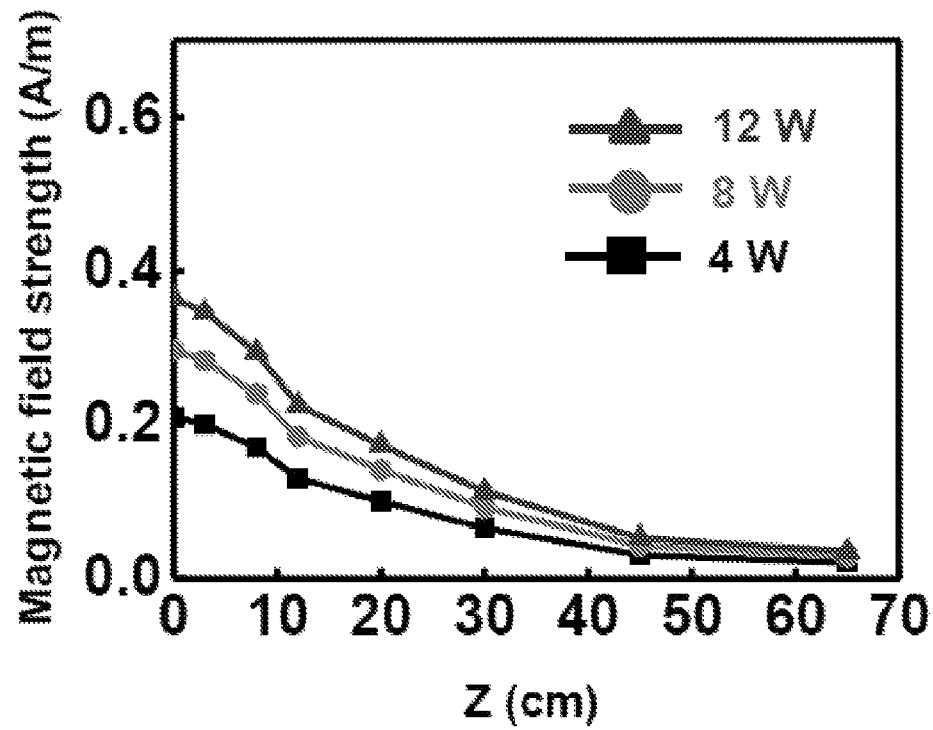
Figure 16A:
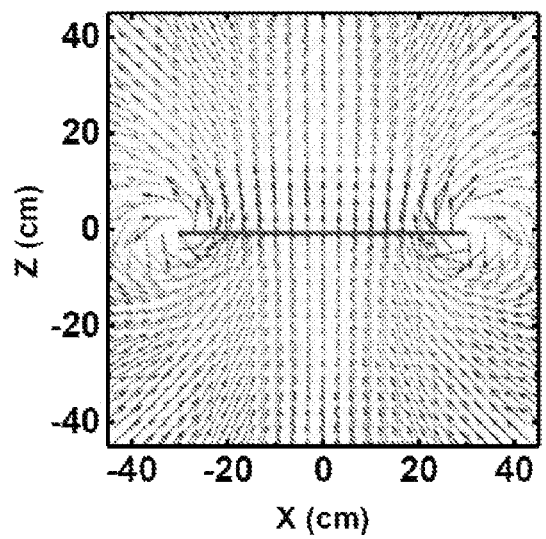
FIGS. 16A-16D. Magnetic field for P=12 W.
Figure 16B:
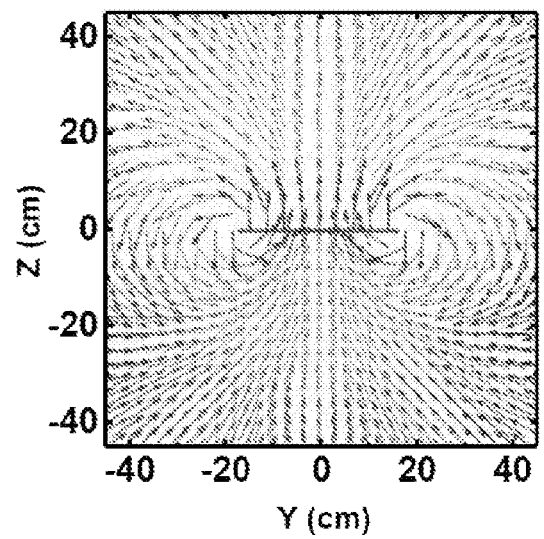
Figure 16C:
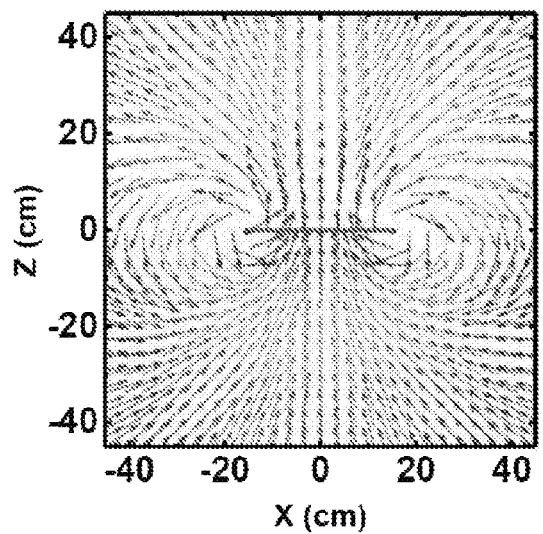
Figure 16D:
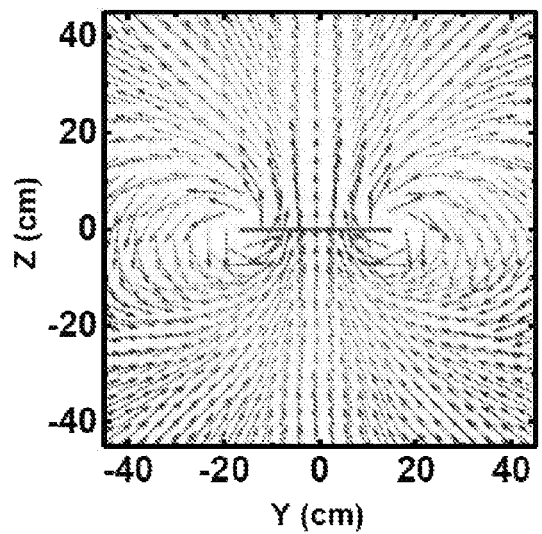

Long range wireless communication and power delivery, and multiplexed readout: Because a typical sensor in certain embodiments, such as shown in FIG. 3A, requires relatively small power for operation, (standby: 2 μA @ 1.5V (~3 μW); operating: 150 μA @ 1.5V (~225 μW) a standard smartphone can be used as a reader over distances of a few centimeters, as in FIG. 14. Full body coverage requires a large-scale loop antenna system and RF power supply (P, typically a few Watts). The operating range depends on the sizes and numbers of reader antennas, the RF power supplied to them, the size of the sensor antenna, and its orientation relative to the reader. FIGS. 3B-3C show images and diagrams of two reader antennas (Feig Electronics, ANT800/600-DA, 852 mm×620 mm×40 mm) next to each other, such that multiplexed operation allows full-body area coverage. For examples here, communication and power delivery occurs to 65 separate sensors in a time sequential manner, continuously, such that all 65 sensors can be read in a total of 3 seconds.

Figures 17A, 17B, 17C:
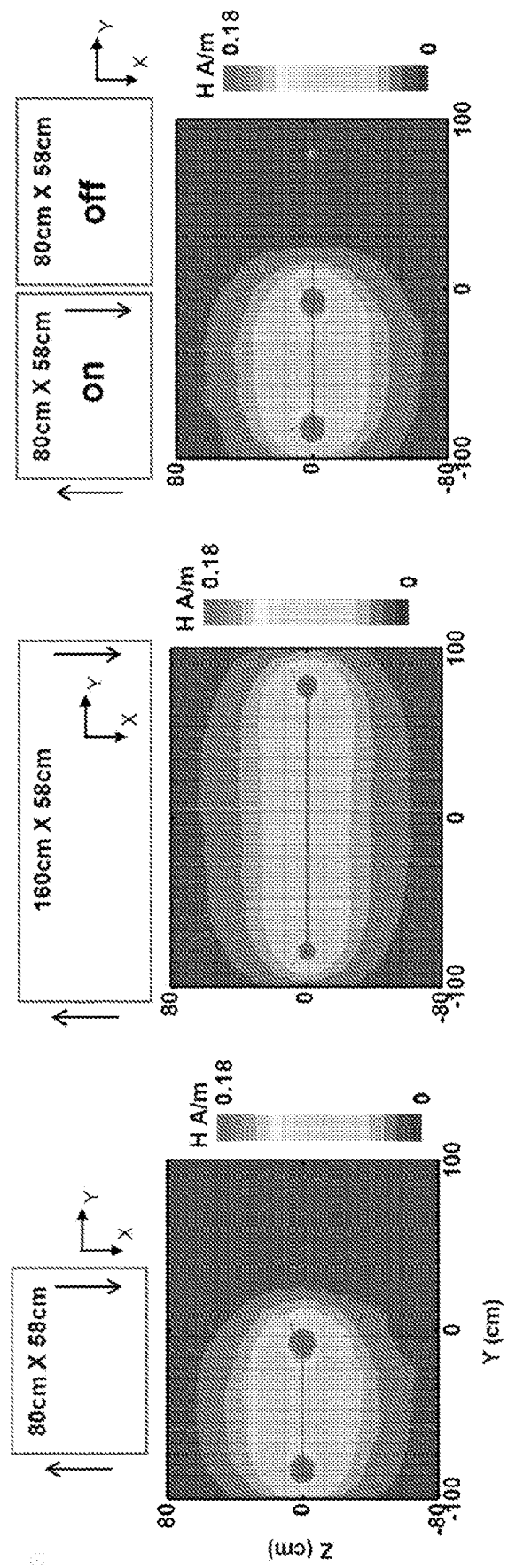
FIGS. 17A-17C. Effect of antenna size on magnetic field strength.
Figure 18A:
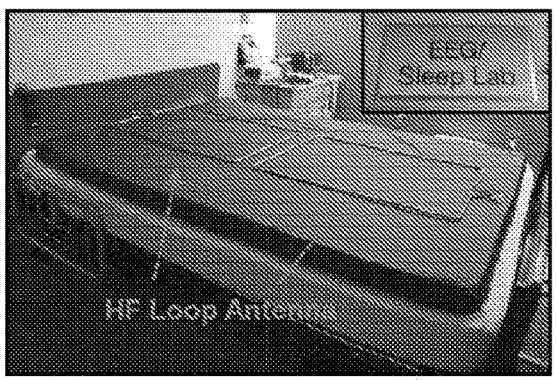
FIGS. 18A-18D. Photographs of sleep study application, illustrating size and geometry of HF loop antenna embedded in bed and sensors positioned on the body (see FIG. 20A for positions).
Figure 18B:
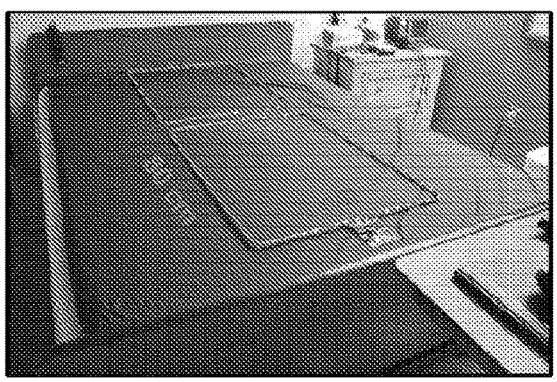
Figure 18C:
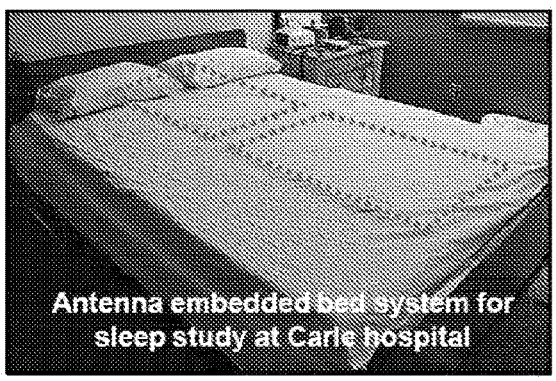
Figure 18D:
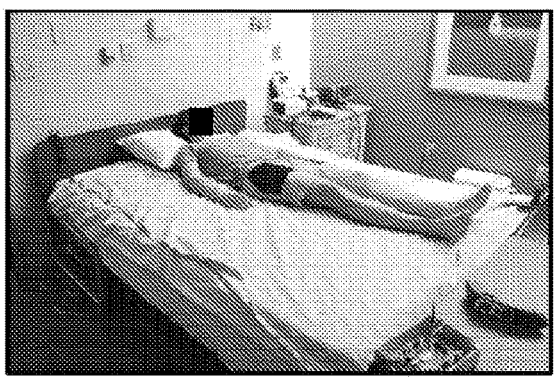

The range for a sensor oriented parallel to the reader antenna, as measured by the maximum distance from the sensor to the reader antenna at which operation is possible, is between 12 cm and 32 cm for RF power between 4 and 12 W, respectively. FIG. 3D and FIGS. 15A-15D show the communication distance of the device with the various location inside each antenna at different power levels. For all the cases, the middle part of the antenna provides the longest distance. For comparison, calculations of the corresponding magnetic field strengths are in FIG. 3E and FIGS. 15C-15D. The strength increases with the power and decreases with the distance along the z axis (according to $\sqrt{P}$), as expected. FIGS. 3F-3G and FIGS. 16A-16D show the magnetic field distributions for P=12 W. Although the magnetic field near the small reader antenna is larger than the medium and large antennas, its direction is non-uniform. The large reader antenna yields a more uniform magnetic field direction than the small and medium ones. For communication distance Z>~20 cm, the magnetic field strength of the large reader antenna is the highest and has the largest coverage. For all cases (P=4 W, 8 W and 12 W), the computed ranges for the large (800×580×10 mm), medium (649×165×10 mm) and small (300×300×10 mm) reader antennas, as in FIGS. 3D, 15A-15B, and 16A-16D respectively, are comparable to experimental observations. In addition to the cases above, a reader antenna with size 1600×580×10 mm can work, although with a magnetic field strength (FIG. 17B) that offers insufficient range. As a result, for full-body applications, a preferred approach is to use two separate, large reader antennas (800×58×10 mm) are placed in parallel in the X-Y plane and operated in a time multiplexed manner. Simulation and experimental results indicate that the magnetic field strength with one antenna on and the other off is almost the same as that for a single antenna as in FIG. 17C.

Example 2: Full-Body Thermography in a Clinical Sleep Laboratory to Assess Circadian Phase Temperature variations during sleep can be used to gauge the circadian phase, with important implications for the characterization and treatment of relatively common sleep disorders including delayed sleep-wake phase, advanced sleep-wake phase, and jet lag. Traditionally, measurements occur only in research laboratories with invasive (e.g. rectal probes) techniques, with a single or small number (2~8) point measurements on the skin, or with infrared imaging on bare regions of the skin. All such methods are disruptive to normal sleep and they cannot be readily applied in a home setting. Alternative approaches, such as analysis of salivary melatonin involve disruption of natural sleep, without capabilities in continuous monitoring. Wireless, epidermal sensor arrays like those introduced here have value in this context.

Figure 4B:
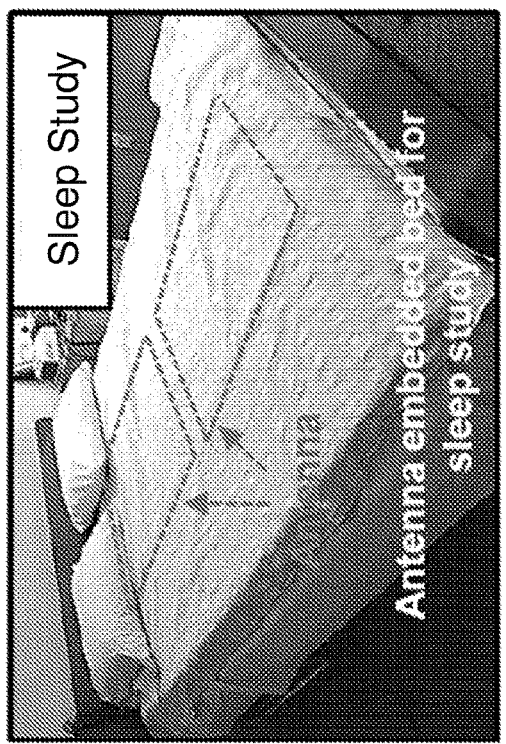
Figure 4C:
Figure 4A:
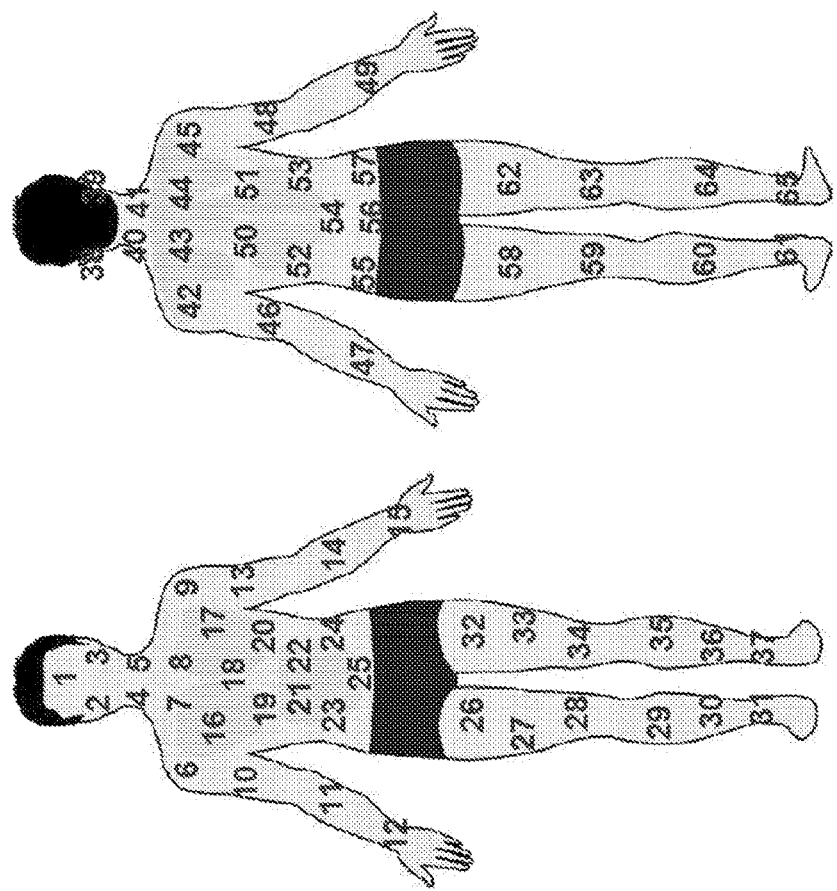
Figure 19A:
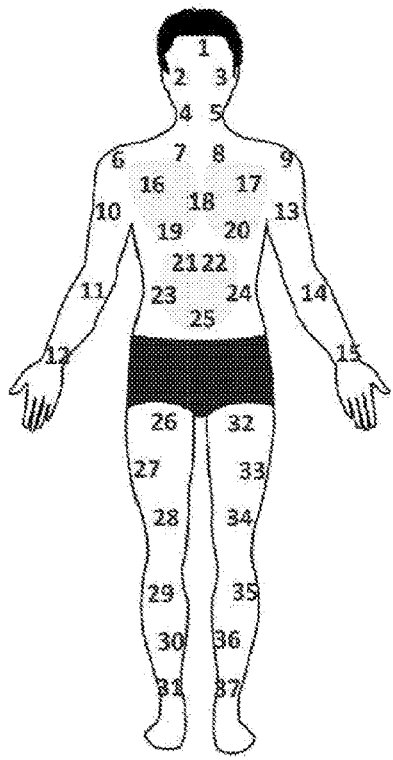
FIGS. 19A-19H. Data from temperature sensors positioned on the body front surface for each of 37 sensors.
Figure 19B:
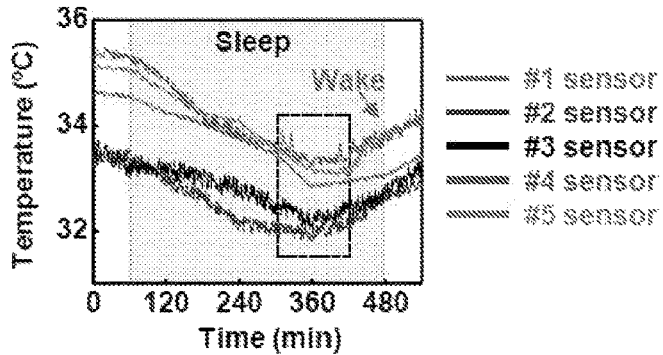
Figure 19C:
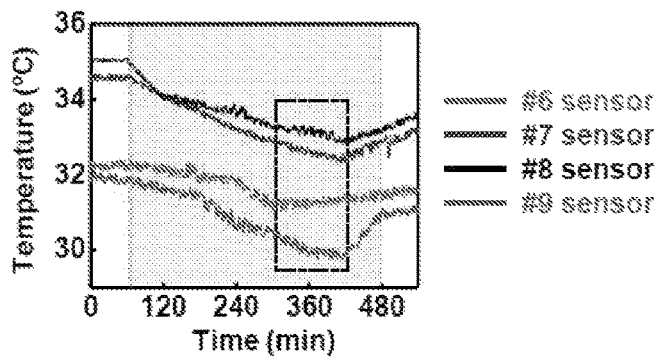
Figure 19D:
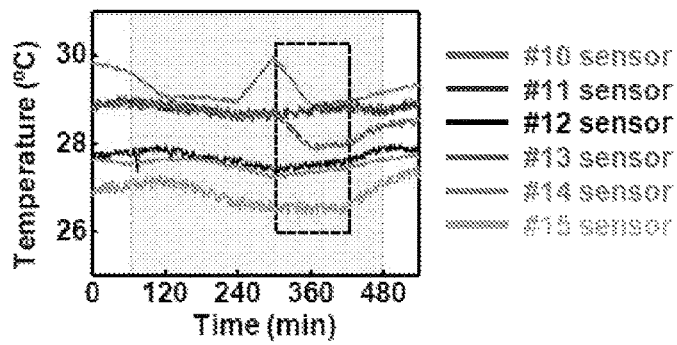
Figure 19E:
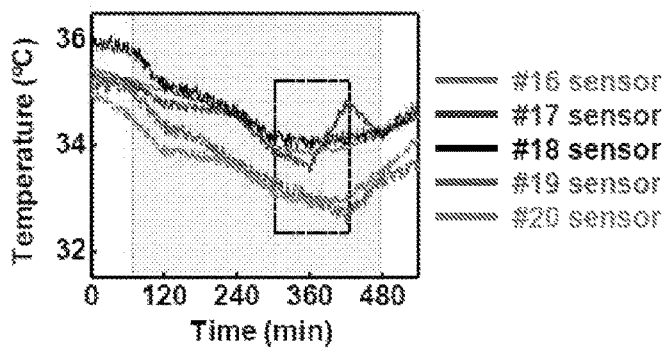
Figure 19F:
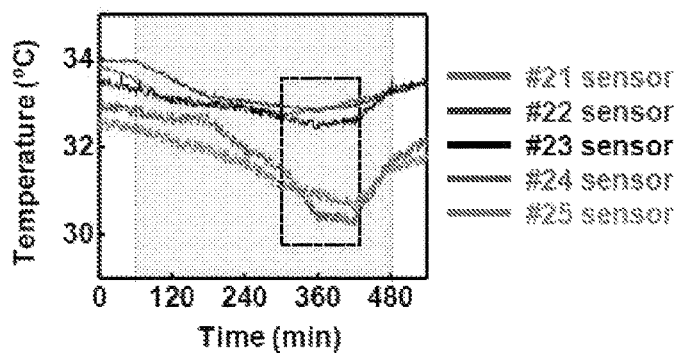
Figure 19G:
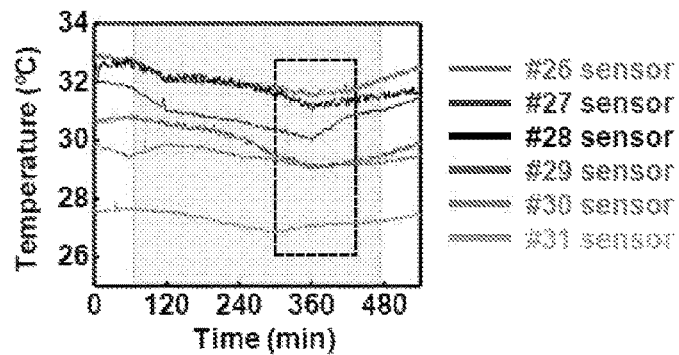
Figure 19H:
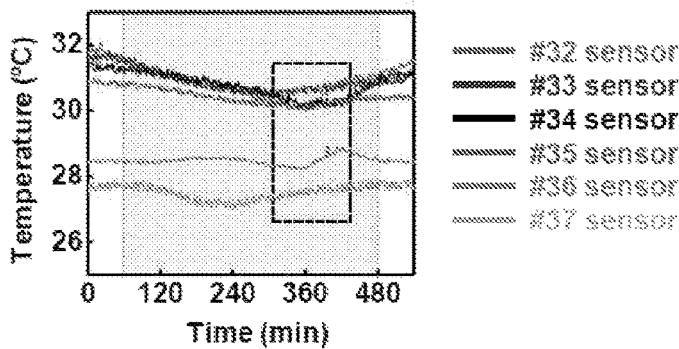
Figure 20A:
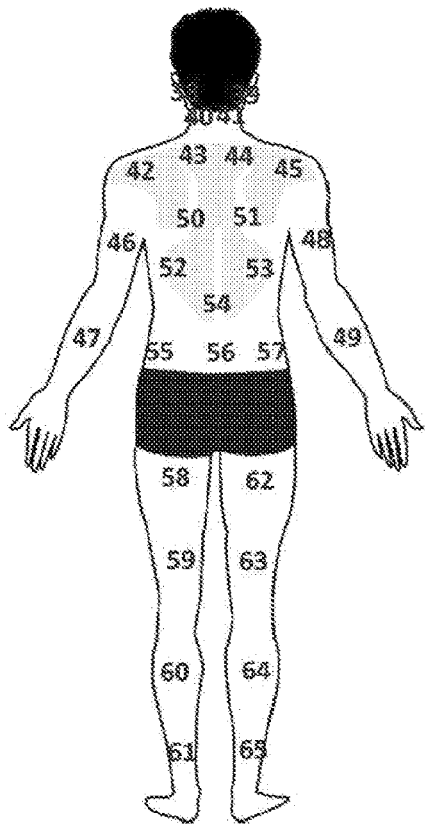
FIGS. 20A-20H. Data from temperature sensors positioned on the body back surface for each of 28 sensors.
Figure 20B:
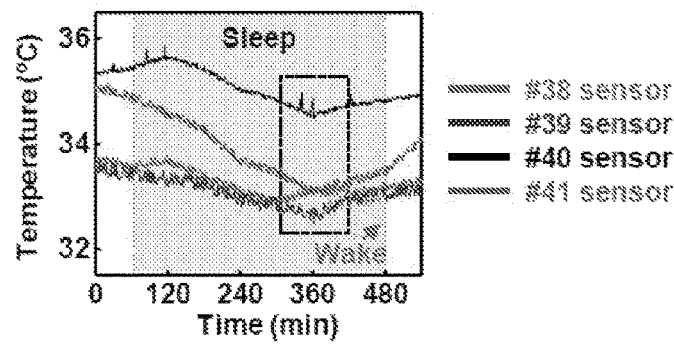
Figure 20C:
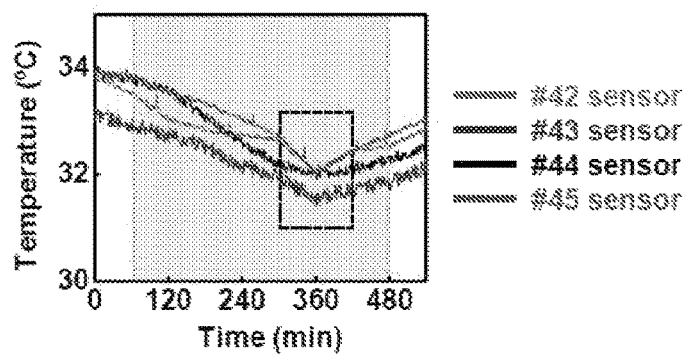
Figure 20D:
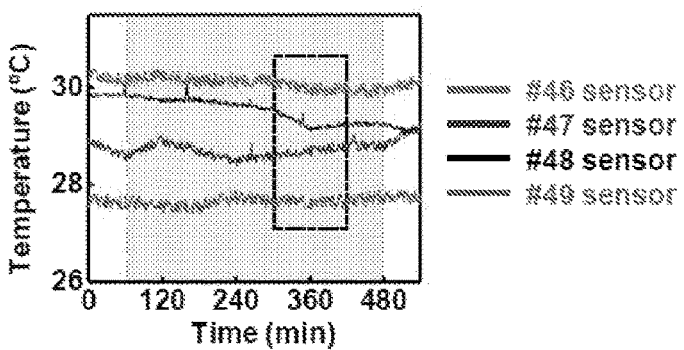
Figure 20E:
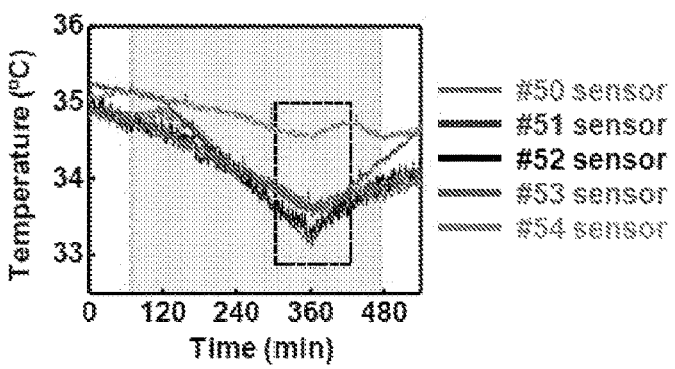
Figure 20F:
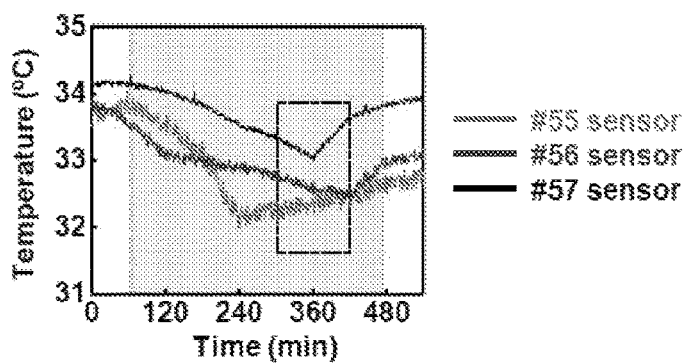
Figure 20G:
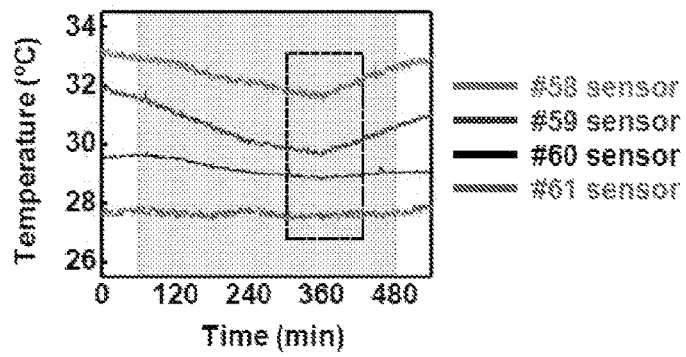
Figure 20H:
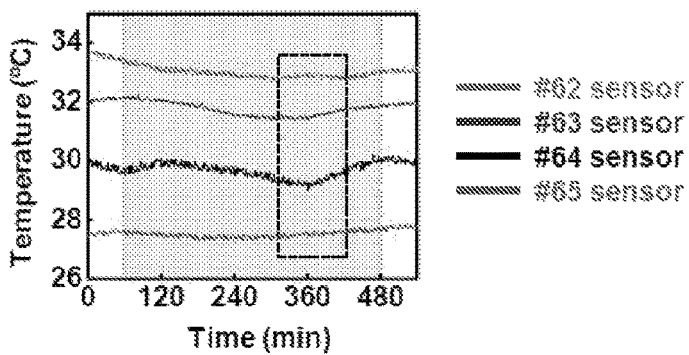
Figure 21A:
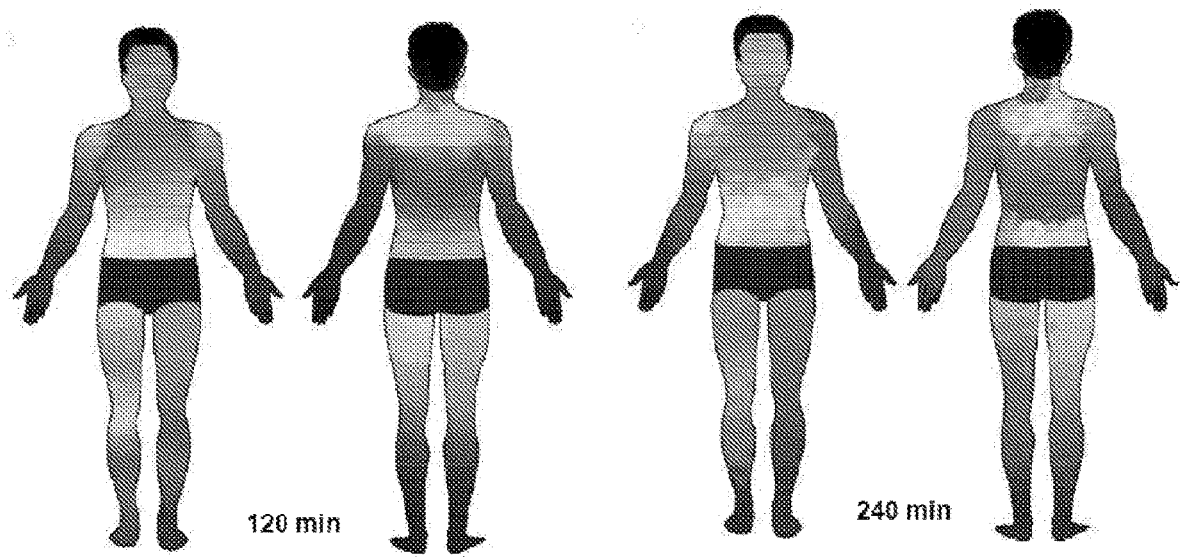
Figure 21B:
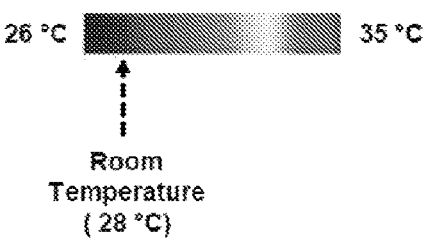
Figure 22A:
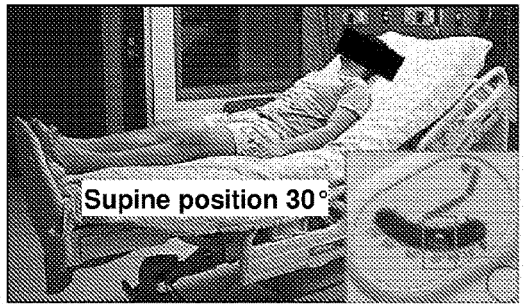
FIGS. 22A-22B. Wirelessly recorded data from pressure sensors for a patient in a supine position 30°, illustrating different pressures on different portions of the body surface.
Figure 22B:
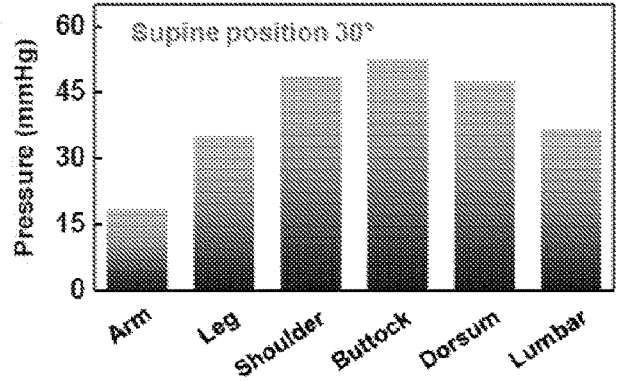
Figure 23A:
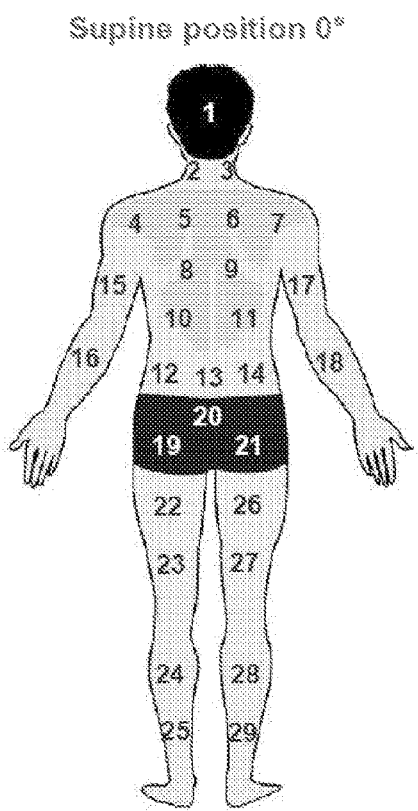
FIGS. 23A-23G. Wirelessly recorded data from pressure sensors for a patient in a supine position 0°
Figure 23B:
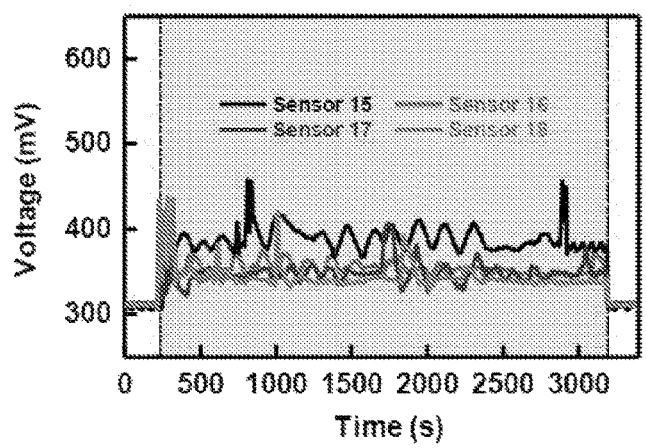
Figure 23C:
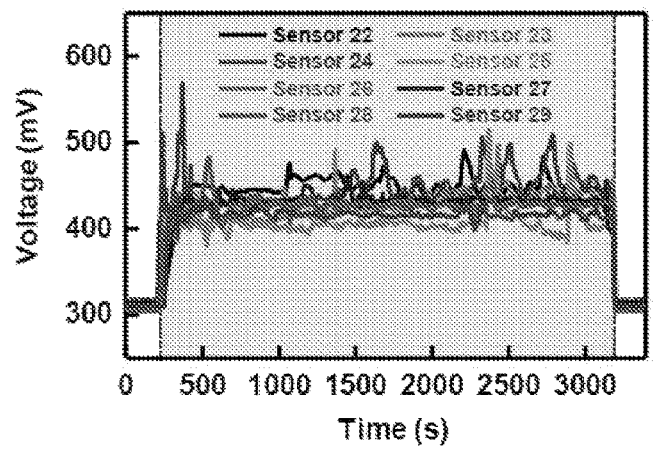
Figure 23D:
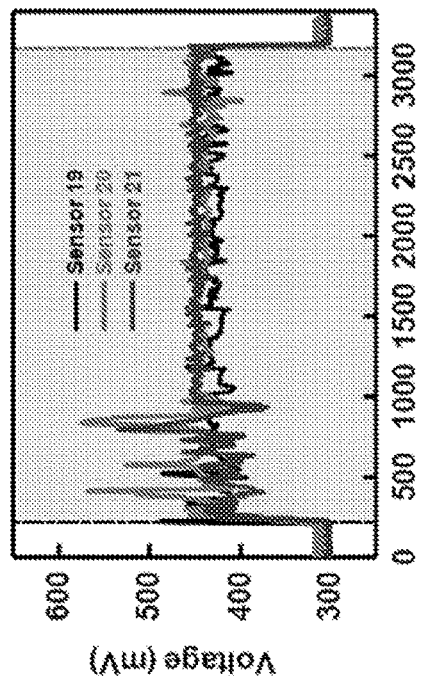
Figure 23F:
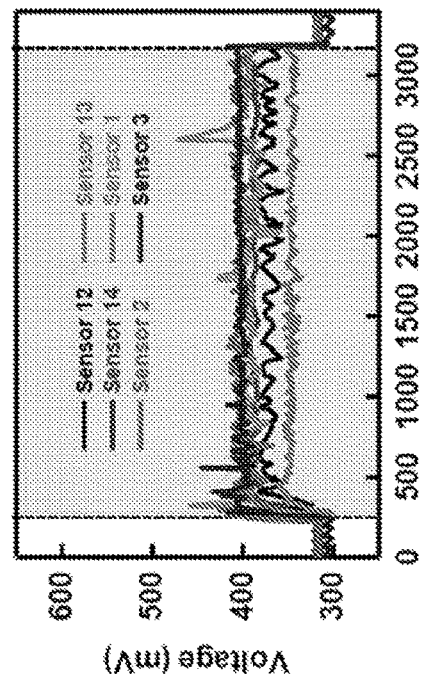
Figure 23E:
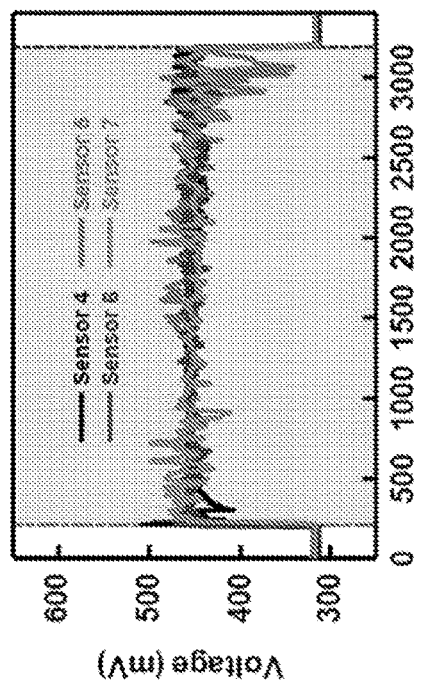
Figure 23G:
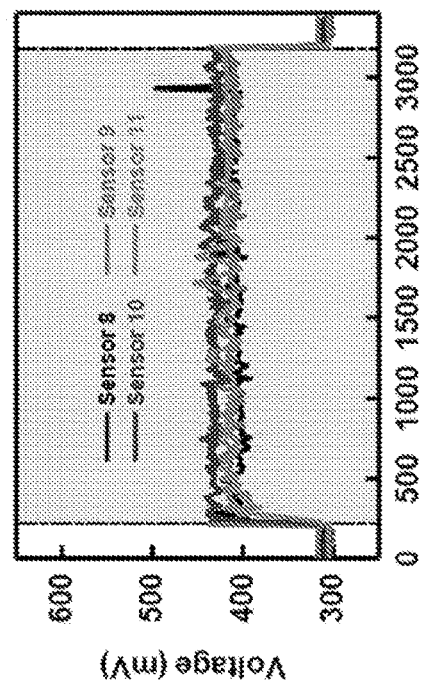
Figure 24A:
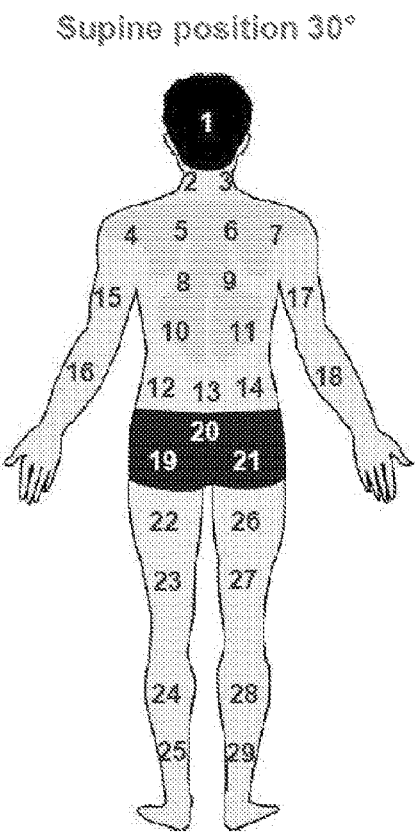
FIGS. 24A-24G. Wirelessly recorded data from pressure sensors for a patient in a supine position 30°
Figure 24B:
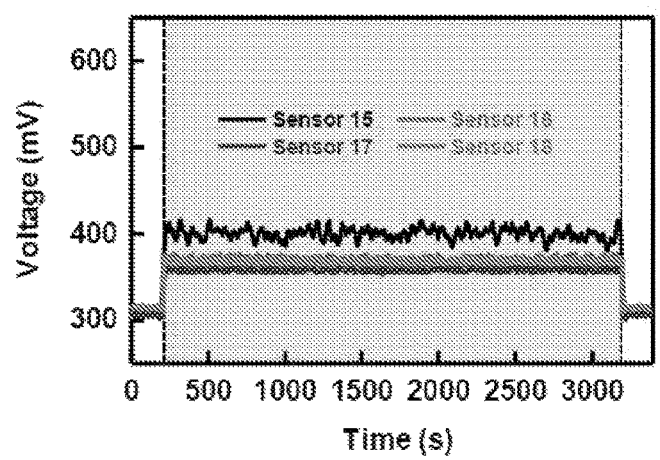
Figure 24C:
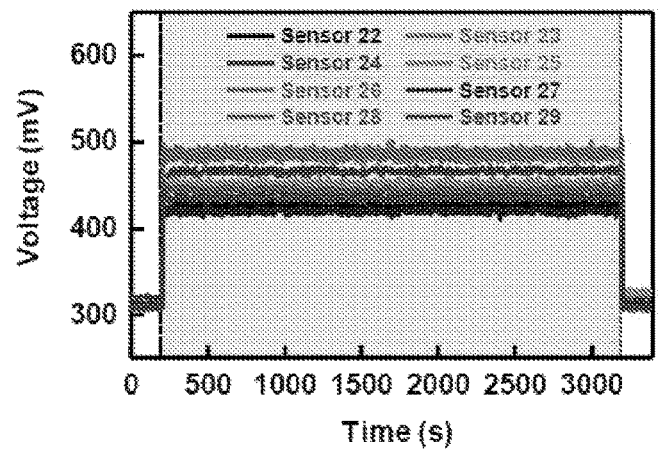
Figure 24D:
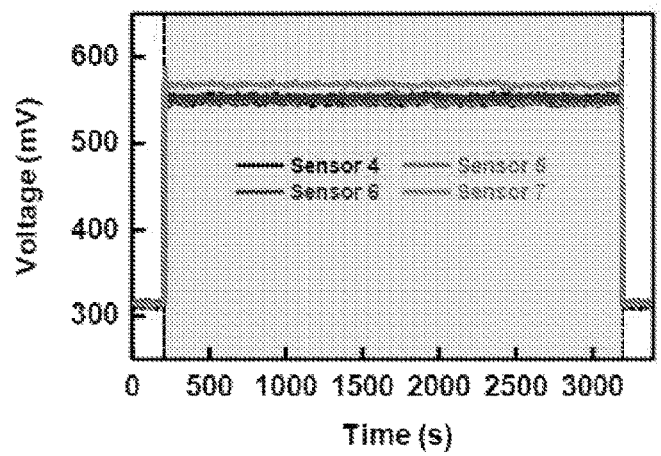
Figure 24E:
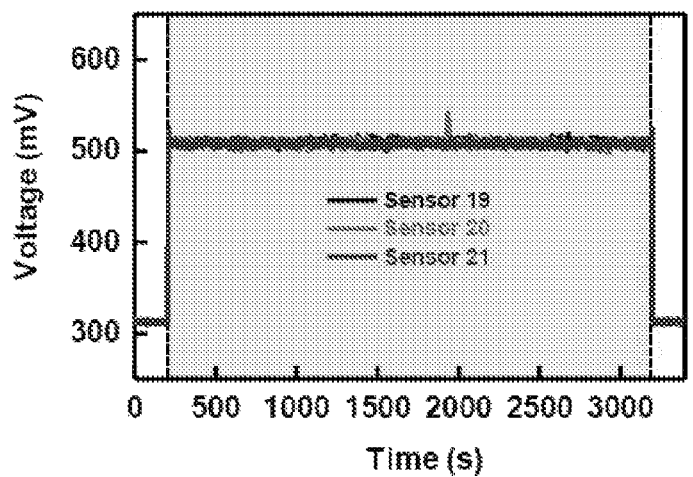
Figure 24F:
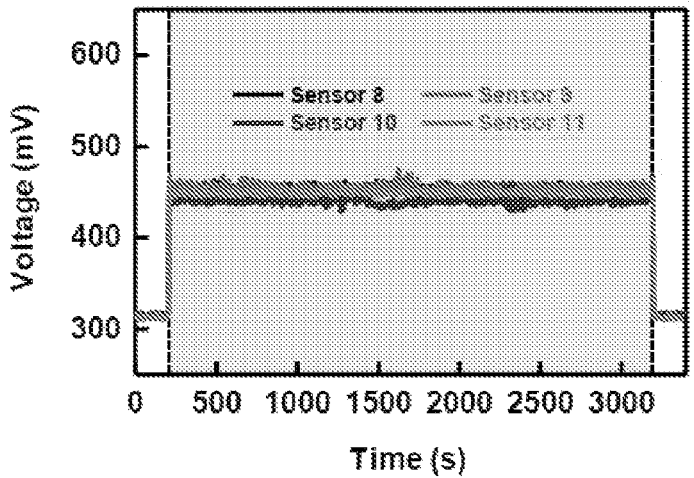
Figure 24G:
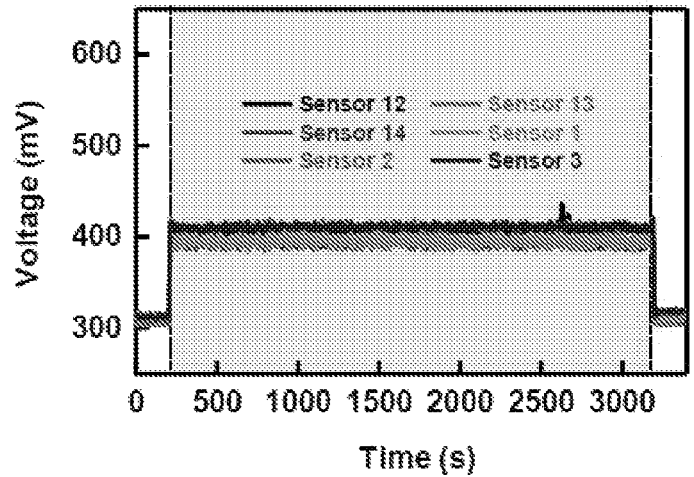
Figure 25A:
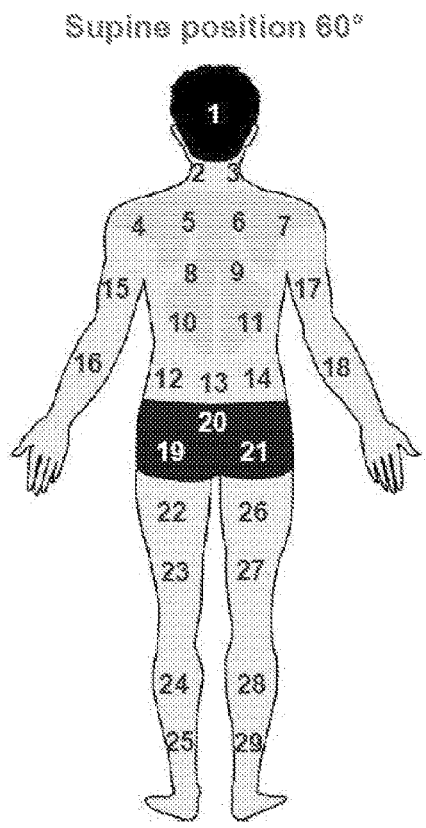
FIGS. 25A-25G. Wirelessly recorded data from pressure sensors for a patient in a supine position 60°.
Figure 25B:
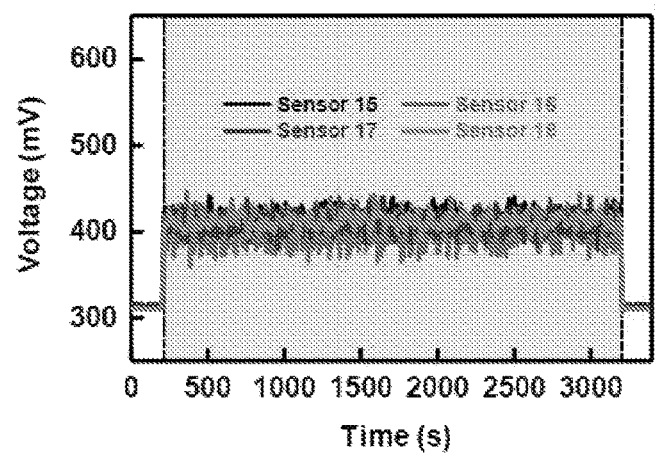
Figure 25C:
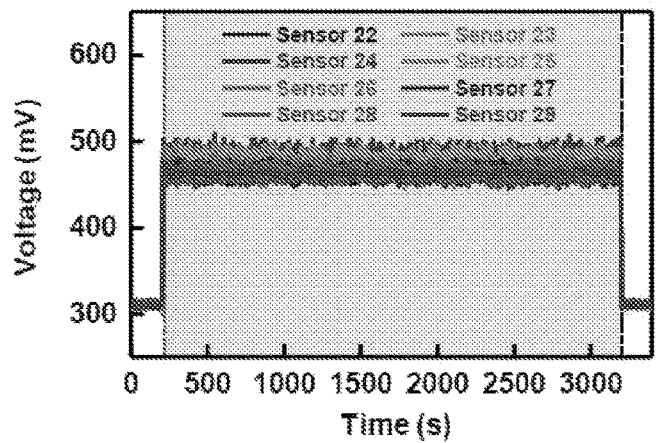
Figure 25D:
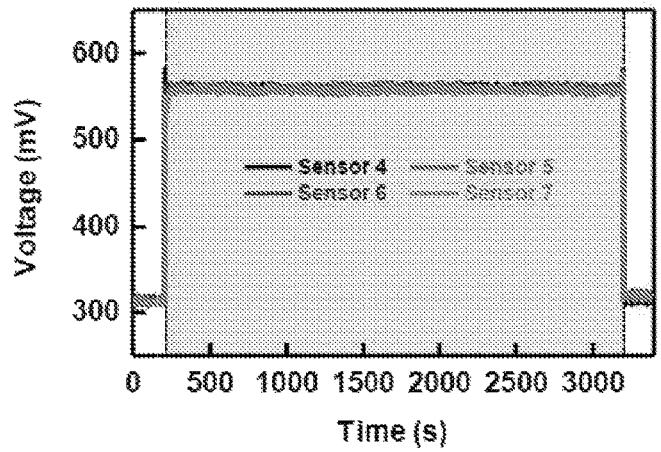
Figure 25E:
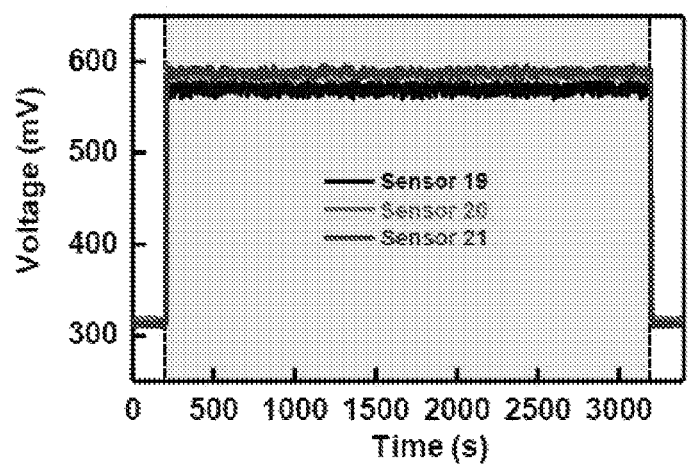
Figure 25F:
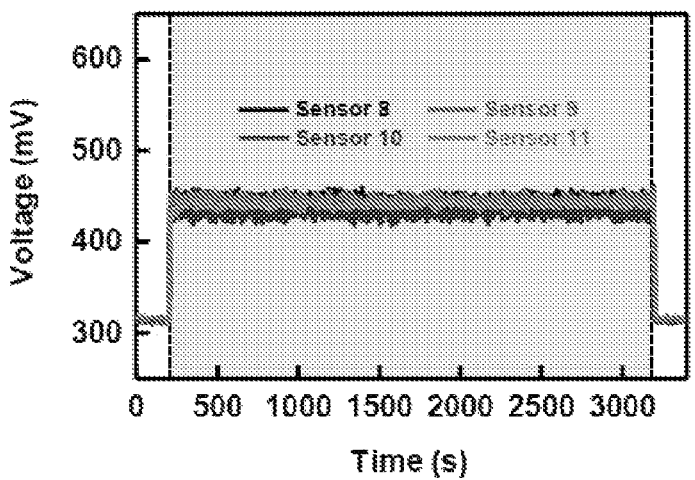
Figure 25G:
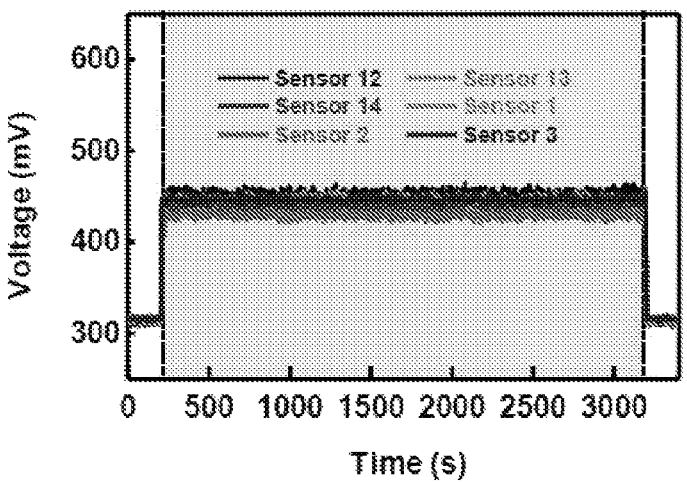

Sleep studies based on protocols that include human subjects in a clinical sleep laboratory demonstrate some capabilities in wireless sensing for full-body thermography to reveal characteristic patterns of sleep. As shown in the embodiment depicted in FIGS. 4B-4C, two custom large-scale reader antennas constructed using small diameter copper tubes (800×580×10 mm) reside under a pad (topper, ~5 cm thickness) placed on top of the mattress, as in FIGS. 18A-18D. In one embodiment, a total of 65 sensors placed as shown in FIG. 4A provide full-body coverage on a 27 year old male subject. Full body temperature mapping occurs at a rate of 20 times per minute, continuously during the course of the sleep study, i.e. 9 hours. Wirelessly recorded temperatures at several representative body locations over 7 hours of sleep appear in FIGS. 4D-4F, where the results correspond to local body averages. The FIGS. 19A-19H and FIGS. 20A-20H contain raw data from all 65 sensors, but in this main figure, it shows the average temperature results of each part of body. As expected, the core area of body has a temperature that is 2~3° C. higher than periphery (i.e. distant area from the heart). Additionally, FIG. 19D shows pronounced reductions in temperature at naked locations, thereby illustrating the value of simultaneous measurements at many body locations. The shaded portions of the graphs highlight the regions that correspond to sleeping. In most cases, the temperature begins to decrease at the onset of sleep (~60 min), with a minimum value at 2~3 hours (black box) before waking. FIGS. 4G-4I show color, full-body heat maps constructed based on the measured temperature data (60, 360, and 480 min. additional color heat maps are shown in FIGS. 21A-21D), with interpolation between sensor locations. The color heat maps, further demonstrate that the lowest body temperature occurs 2~3 hours waking.

Figure 5B:
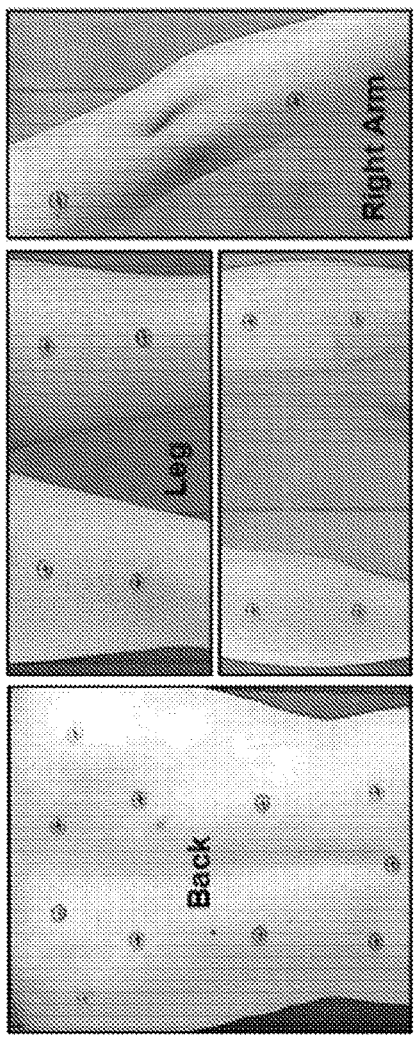
Figure 5D:
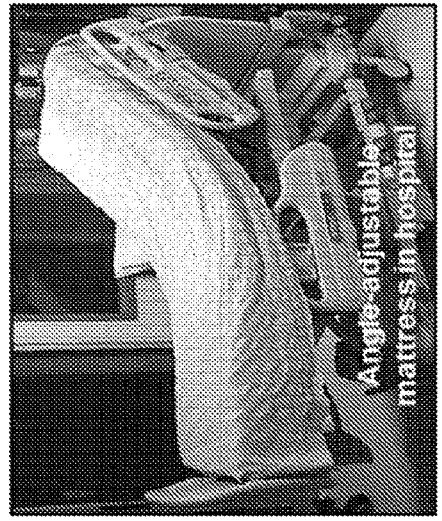
Figure 5C:
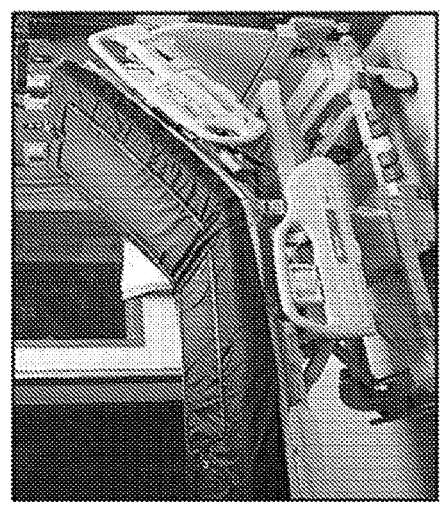
Figure 5A:
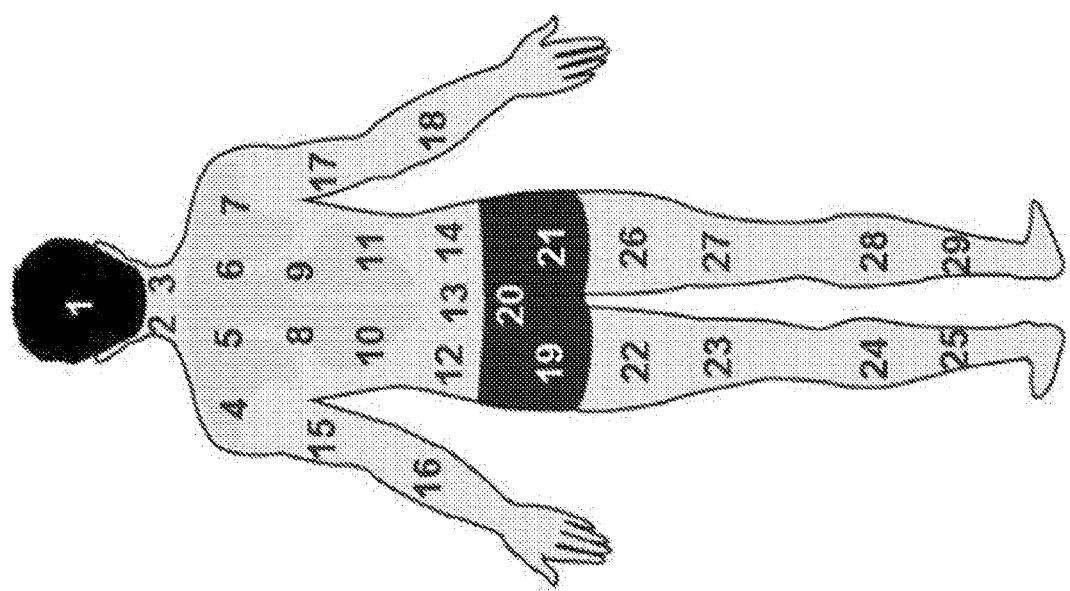
Figure 5F:
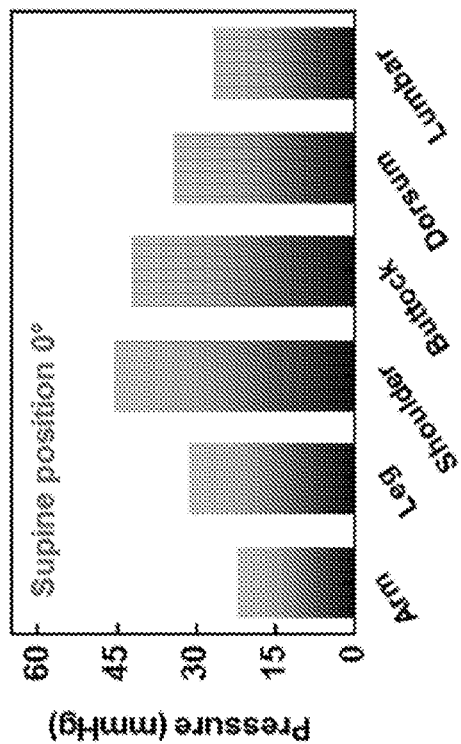
Figure 5H:
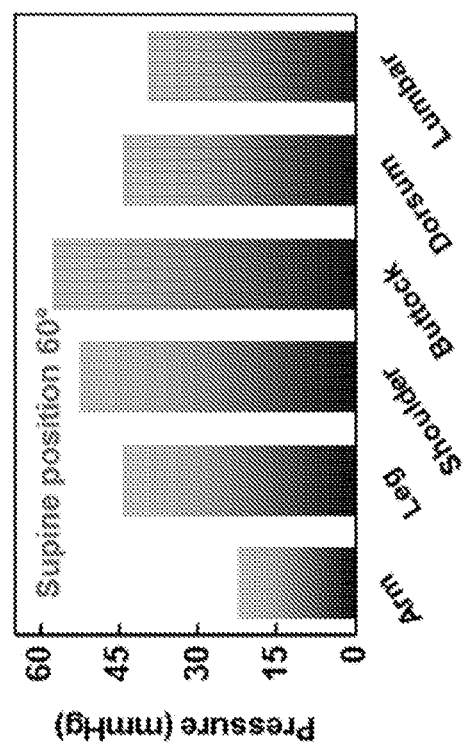
Figure 5E:
Figure 5G:
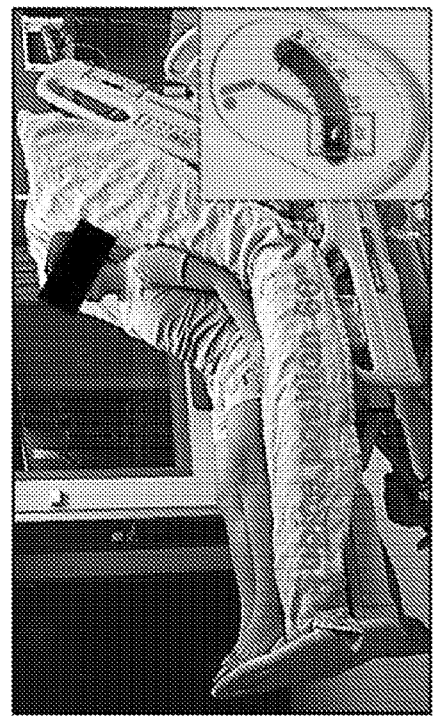

Example 3: Full-Body Pressure Measurement in a Hospital Bed to Assess Risk for Skin-Ulcers Another area of application relevant for the devices and methods described herein is pressure monitoring to track the risk for potential development of ulcers, which occur in 4.5-7% of hospitalized patients and involve substantially increased costs of care and lengths of stay at the hospital. Specifically, measurements of pressure on the skin while lying on a bed can provide critical information regarding the need to take preventive action to avoid skin-sores, irritation, and decubitus ulcers. The technology platform described herein has a particularly unique value in this context. FIGS. 5A-5B show 29 dorsal-mounted NFC pressure sensors on a human subject with specific positions as indicated, each with a design like that in FIG. 2F. FIGS. 5C-5D present a hospital environment that involves an angle-adjustable mattress, shown here with 27 years old male, (weight: 90 kg). FIGS. 5E, 5G and FIGS. 22A-22B summarize wirelessly recorded data (sampling rate 4 Hz, with sensors identified by number: arm, 15~18; leg, 22~29; shoulder, 4~7; buttock, 19~21; dorsum, 8~11; lumbar, 12~14; head, 1; neck, 2~3) while lying at supine angles of 0, 30, and 60°, as highlighted with red lines in each image. In FIGS. 5F-5H, the shoulder, buttocks, and dorsum experience increases in average pressure with increasing angle. The arm, legs, and lumbar part experienced show an opposite trend. These results appear as color maps for various body positions in FIGS. 5I-5K. As the angle of the mattress increases, the shoulder and buttock regions experience corresponding increases in pressure. These pressures align with expectation and they are consistent with literature data obtained using a measuring sheet (e.g., ABW, Hamburg, Germany) that embeds 684 conventional wired sensors and rests on the mattress. The raw data appear in FIGS. 23A-23G, 24A-24G and 25A-25G. In addition to average and time-integrated values, the sensors can capture changes in pressure, in real-time, associated with minor movements of the subject, thereby offering additional utility in sleep monitoring, per the previous section (fluctuation graph in FIGS. 24A-24G, 25A-25G and 26A-26G).

These examples demonstrate the ability to operate large-scale distributed collections of multimodal wireless sensors across the body, with important capabilities in the context of two clinically relevant applications. The thin, soft construction of the devices and the battery-free operation allow them to integrate with the skin in a comfortable, physically 'imperceptible' fashion that also avoids any irritation associated with pressure or thermal loads. The basic platforms are compatible with many other types of functionality, including but not limited to measurements of electrophysiology, blood oximetry, heart and respiration rate and photoplethysmograms. These opportunities, as well as future possibilities in physical, thermal or electrical stimulation, represent promising directions for additional research.

Methods

Fabrication of wireless NFC temperature and pressure sensor. The fabrication, with details in supplementary note 1, began with spin-coating of a layer of polyimide (PI; 1.2 μm) on a copper foil (Cu; 5 μm), as the first step in defining the loop antenna. Laminating the sheet, with PI side down, onto a glass slide coated with polydimethylsiloxane (PDMS) prepared the structure for photolithography and wet etching to create the loop (diameter; 16 mm, width; 75 μm). Another layer of PI (1.2 μm) uniformly spin-cast on top served as an encapsulation layer. Photolithography and dry etching (RIE; 20 sccm $O_2$, 200 mTorr, 150 W, 900 s) created small vias through the PI at each end of the loop, for electrical connection. Electron beam evaporation formed another layer of Cu (1 μm). Photolithography and wet etching defined traces and contacts through the vias. Spin-casting yielded an additional coating of PI (1.2 μm). Electron beam evaporation, photolithography and dry etching (RIE; 20 sccm $CF_4$, 50 mTorr, 100 W, 10 min) defined a hard mask of $SiO_2$ (50 nm). Further dry etching (20 sccm $O_2$, 300 mTorr, 200 W, 1800 s) removed the exposed regions of the PI to create openings for electrical connection to the NFC die. A cellulose-based, water soluble tape (e.g., Aquasol Corporation, ASWT-2) enabled retrieval of the resulting structure from the PDMS/glass substrate. Electron beam evaporation of a uniform layer of $Ti/SiO_2$ (5 nm/100 nm) onto the backside of this structure followed by exposure to UV-induced ozone allowed strong bonding to a base layer of PDMS. After removal of the water soluble tape, application of an In/Ag based solder (e.g., Indium Corporation, Ind. 290, 180° C.) established a mechanical and electrical interface between a thin (1~2 μm) NFC bare die, the loop antenna and traces that lead to the components for pressure sensing.

As separate set of fabrication steps outlined below formed a p-doped thin membrane of silicon in the shape of a spiral on a film of polyethylene terephthalate (PET, e.g., SKC, Inc) as a pressure sensor. Silver epoxy (e.g., Ted Pella, Inc) bonded this sensor and external resistor (0.6×0.3×0.3 mm) to corresponding electrode pads on the device. Bonding an additional layer of PDMS formed the top overlayer. Cutting through this layer and the base layer in a disc shape with a slightly larger radius than the loop antenna completed the fabrication.

Fabrication of p+ doping silicon based pressure module. The fabrication, with details in supplementary note 2, began with p-doping the top silicon layer of an SOI wafer. Undercut etching of the buried oxide layer followed by transfer printing integrated this layer of silicon onto a film of PET (thickness: 5 μm) coated with a layer (thickness: 1.5 μm) of epoxy (SU-8, e.g., Microchem Corp.). Photolithography followed by wet and dry etching formed a spiral shape from the silicon membrane. Electron beam evaporation, photolithography and wet etching defined patterns of metal (Cr/Au, thicknesses: 13, 150 nm) for contacts to the ends of the spiral shape. Spin-casting a layer of polyimide (thickness: 1.2 μm) and selective etching defined an electrically insulating encapsulation layer with openings aligned to the metal contacts.

Evaluations in temperature sensing. The studies involved a volunteer (male, 29 years old) reclined in a chair with his left forearm gently secured to the armrest. A wireless sensor placed on the ventral side of the left forearm provided continuous measurements of temperature. An infrared camera placed 41 cm from the forearm, focused on the sensor as shown in FIG. 2A, yielded data for comparison. Additional tests with similar set-ups used three separate sensors laminated on the back of the hand. Here, measurements occurred during exposure to a temperature controllable heat gun (e.g., Milwaukee, 8988-20), as shown in FIGS. 8A-8G. In all cases, results from the wireless sensors quantitatively match those with the IR camera, with differences typically less than 0.2° C.

Tests of temperature changes associated with respiration. The studies involved a volunteer (male, 29 years old) seated on a chair with a wireless sensor laminated on the skin of the upper lip, just below the nostril. In an ambient lab environment, the measurements showed smooth oscillations between 35.5° C. and 35.1° C., time coincident with cycles of respiration, at a rate of 4 breaths per 10 seconds.

Evaluations in pressure sensing. The studies involved a volunteer (male, 29 years old) reclined in a chair with his left forearm gently secured to the armrest. An encapsulated pressure sensor placed on the ventral side of the left forearm as shown FIG. 2E captured variations associated with force applied with a fingertip. Qualitatively, the response correlated to the magnitude of the force, with larger values for poking and smaller ones for gentle touch, and transients that correlated to the time duration of the applied force. Continuous pressure led to constant response. The resistances of silicon pressure module ($R_0$=29.3 kΩ) in this experiment and additional resistor ($R_2$=220 kΩ) and calibration result in FIG. 11C utilized to calculate forces of each pressing way.

Use in a clinical sleep laboratory. The studies involved a volunteer (male, 27 years old) with 65 wireless sensors mounted at locations across his entire body, with measurements performed while sleeping on a mattress with a pair of reader antennas underneath in a sleep study laboratory at Carle Hospital. Each sensor transmitted data for 0.045 seconds every 3 seconds, from 10 μm to 7 am.

Use in a hospital room. The studies involved a volunteer (male, 29 years old, 90 kg mass) with 29 wireless sensors mounted at locations across his back, and measurements performed while lying on a mattress to measure pressure between his body and mattress. Like sleep study set-up, two large size antennas embedded in mattress and measured pressures of each body part for 10 minutes. The resistances of silicon pressure module ($R_0$=29.3 kΩ) in this experiment and additional resistor ($R_2$=300 kΩ) and calibration result in FIG. 9C utilized to calculate pressures of each body part.

Electromagnetic simulations. The finite element method was adopted in the electromagnetic simulations to calculate the magnetic-field distribution around reader antennas with different sizes (300×300×10 mm, 649×165×10 mm and 800×580×10 mm). The simulations used the commercial software ANSYS HFSS, in which tetrahedron elements were used in the solution with adaptive meshing convergence. The default adaptive convergence condition, together with a spherical surface (1200 mm in radius) as the radiation boundary, ensured computational accuracy. The material parameters include the relative permittivity ($\varepsilon_r$), relative permeability ($\mu_r$) and conductivity ($\sigma$) of the Cu, i.e., $\varepsilon_{r\_Cu}$=1, $\mu_{r\_Cu}$=0.999991 and $\sigma_{Cu}$=5.8×10$^7$ S/m.

Supplementary Note 1: Procedures for Fabricating Temperature and Pressure Sensors.
1. Cut a commercial Cu film to the size of a glass slide.
2. Spin coat with polyimide (PI, poly (pyromellitic dianhydride-co-4,4'-oxydianiline), amic acid solution, Sigma-Aldrich) at 3,000 rpm for 30 s.
3. Bake at 110° C. for 30 s.
4. Bake at 150° C. for 5 min.
5. Bake at 250° C. under vacuum for 1 hr.
6. Spin coat a glass slide with PDMS (Sylgard 184, 10:1, 1000 rpm, 30 s), to a thickness of 25 μm
7. Bake at 110° C. for 10 min.
8. Affix the Cu/PI bilayer onto the PDMS-coated glass slide.
9. Photolithographically pattern (365 nm wavelength; iron oxide mask; Mark Suss MJB3) a layer of photoresist (PR; Clariant AZ4620, 3000 rpm, 30 s;) to define the geometry of the loop antenna. Develop in aqueous base developer (AZ 400K, diluted 2:1)
10. Etch Cu with Cu etchant.
11. Remove PR with acetone. Rinse with IPA.
12. Spin coat with PI at 3,000 rpm for 30 s.
13. Bake at 110° C. for 30 s.
14. Bake at 150° C. for 5 min.
15. Bake at 250° C. under vacuum for 1 hr.
16. Pattern PR (AZ4620) to define via holes.
17. Reactive ion etch (RIE; March CS-1701, 200 mTorr, 20 sccm 02, 150 W, 15 min) to open the vias.
18. Remove PR with acetone. Rinse with IPA.
19. Deposit 1 μm Cu by electron beam evaporation.
20. Pattern PR (AZ4620) to define the bridge interconnect and the electrodes.
21. Etch Cu with Cu etchant.
22. Remove PR with acetone. Rinse with IPA.
23. Spin coat with PI at 3,000 rpm for 30 s.
24. Bake at 110° C. for 30 s.
25. Bake at 150° C. for 5 min.
26. Anneal at 250° C. under vacuum for 1 hr.
27. Deposit 100 nm SiO$_2$ by electron beam evaporation.
28. Pattern PR (AZ4620) for perimeter of NFC coil structure.
29. Reactive ion etch (RIE; March CS-1701, 200 mTorr, 20 sccm 02, 180 W, 50 min) to remove the SiO$_2$
30. Prepare a glass slide with PMMA coating (3000 rpm, 30 s, thickness; 10 μm)
31. Bake at 180° C. for 3 min.
32. Spin coat the glass slide with PDMS (Sylgard 184, 30:1, 1000 rpm, 30 s, thickness; 50 μm)
33. Bake at 110° C. for 15 min.
34. Transfer device with water-soluble tape to a glass slide coated with PMMA and PDMS.
31. Apply FLUX (e.g., WORTHINGTON; 334436) on the electrodes.
32. Solder the NFC chip, resistor, and silicon membrane pressure sensor to appropriate locations.
33. Encapsulate by spin-coating with PDMS (Sylgard 184, 30:1, 300 rpm, 30 s).
34. Cut through the top and bottom layer of PDMS around the perimeter of the device.
35. Add adhesive tape on the bottom of the device by oxygen-plasma treatment.

Supplementary Note 2: Fabrication Procedure of p+ Doping Silicon Based Pressure Module.
1. Clean a SOI wafer by immersion in concentrated HF for 10 s, in piranha solution for 3 min, and then in concentrated HF for 10 s.
2. Perform solid state doping of the silicon by exposure to a boron source at 1000° C. for 25 min.
3. Clean the wafer again using the process of step 1.
4. Photolithographically pattern holes in a layer of photoresist (PR S1805, 3000 rpm, 30 s) and then develop in aqueous base developer (MIF 917).
5. Remove the exposed silicon by RIE (50 mTorr, 40 sccm SF$_6$, 100 W, 1 min).
6. Etch the SiO$_2$ layer by immersion in concentrated HF for 30 min.

Substrate Preparation
7. Spin coat a layer of PDMS (Sylgard 184, 10:1, 3000 rpm, 30 s) on a glass slide.
8. Attach a PET film (thickness; 25 μm) on PDMS
9. Spin coat a layer of photodefinable epoxy (SU-8 2007, Microchem Corp, 3000 rpm, 30 s, thickness; 1.5 μm).
10. Bake at 65° C. for 1 min.
11. Bake at 95° C. for 2 min.

Transfer Printing
12. Retrieve the top Si layer onto the surface of a PDMS stamp.
13. Transfer print the Si layer onto a prepared PET film.
14. Bake at 95° C. for 2 min.
15. Remove PR with acetone. Rinse with IPA.

Silicon Isolation
16. Photolithographically pattern a layer of PR (5214, 3000 rpm, 30 s) and develop in MIF 917. This pattern defines the spiral shape.
17. Remove the exposed silicon by RIE (50 mTorr, 40 sccm SF6, 100 W, 1 min).
18. Remove PR with acetone. Rinse with IPA.
19. Photolithographically pattern a layer of PR (nLOF 2070, 2500 rpm, 30 s) and develop in MIF 917. This pattern defines the contact electrodes.
20. Etch residual oxide by immersion in BOE (NH4F: HF=10:1) for 15 s.

21. Deposit 13/150 nm of Cr/Au by electron beam evaporation.
22. Perform lift-off by immersion in acetone.
23. Spin coat PI at 3000 rpm and 30 s.
24. Bak at 150° C. for 1 hr.
25. Photolithographically pattern a layer of PR. (electrodes) MORE DETAILS?
26. Etch PI with RIE (200 mTorr, 20 sccm $O_2$, 150 W, 15 min).
27. Remove PR with acetone. Rinse with IPA.

Supplementary Note 3: Temperature Measurement and Calibrations.

Figure 6A:
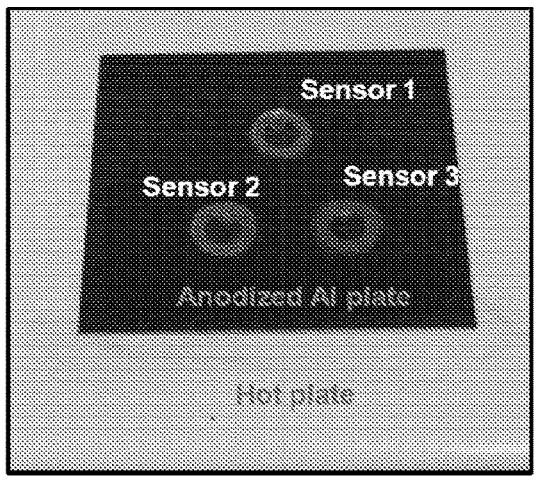
FIGS. 6A-6D illustrate the results of tests to define calibration factors for output of a wireless sensor.
Figure 6B:
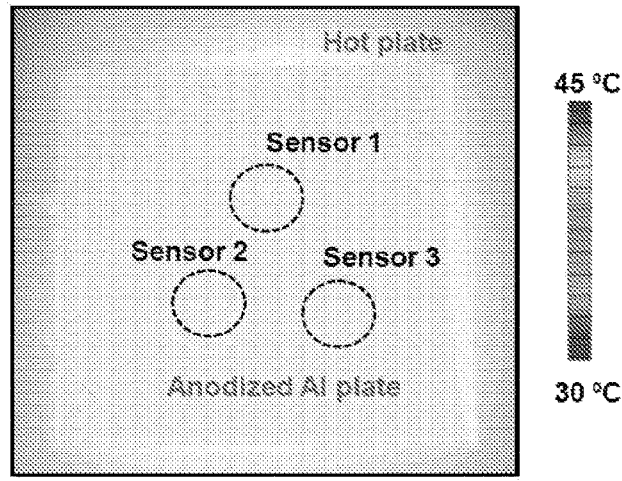
Figure 6C:
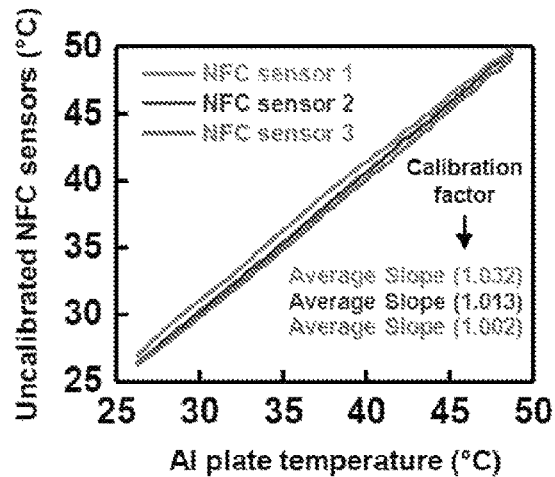
Figure 6D:
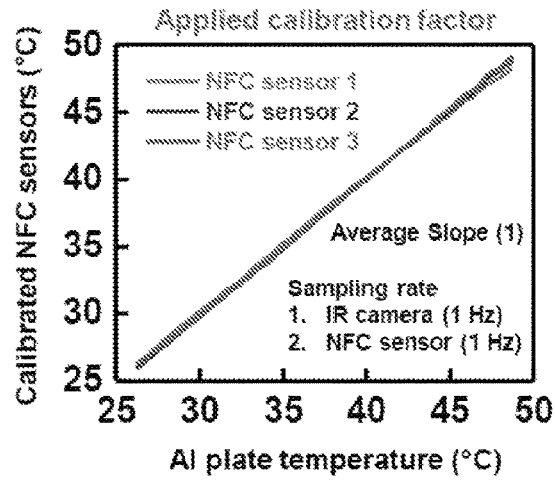
Figure 7A:
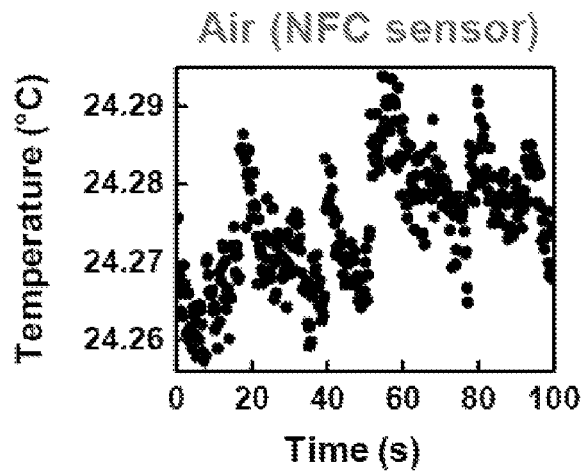
FIGS. 7A-7C are results of wireless recordings of temperature over time for temperature sensors in air (FIG. 7A), on skin (FIG. 7B) and with an IR camera (FIG. 7C).
Figure 7B:
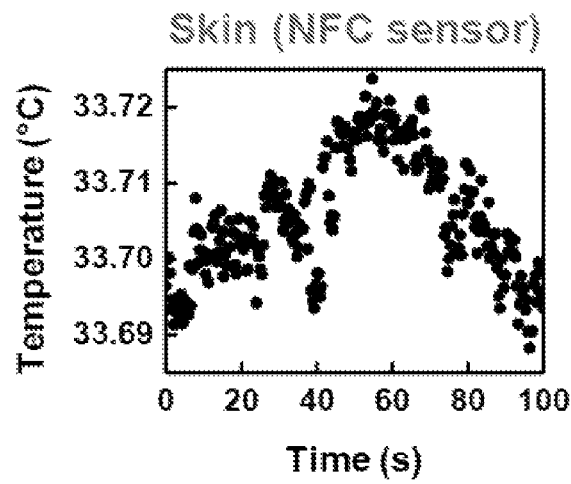
Figure 7C:
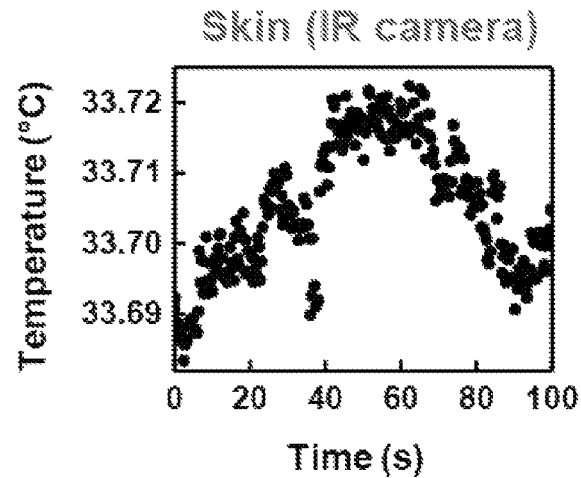
Figure 8A:
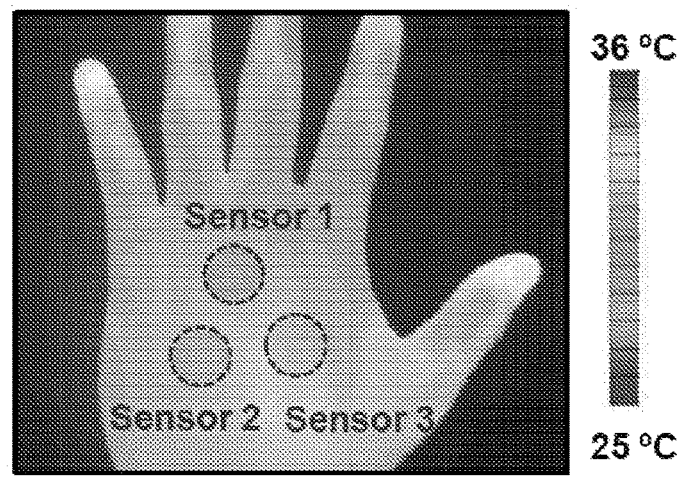
FIGS. 8A-8G illustrate the effects of a temporary thermal stimulus to the hand and resultant measurements using a NFC sensor and IR camera.
Figure 8B:
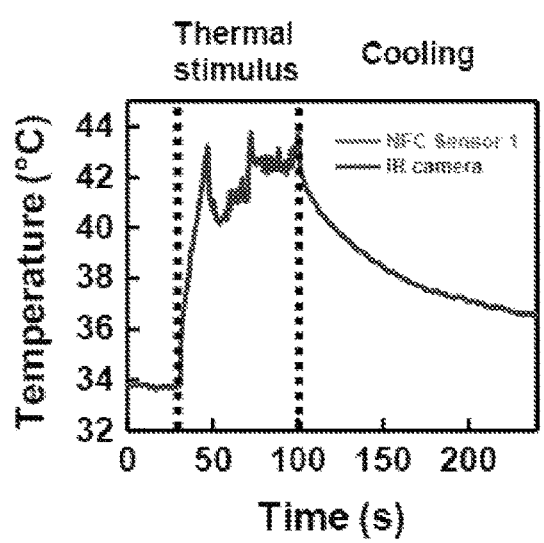
Figure 8C:
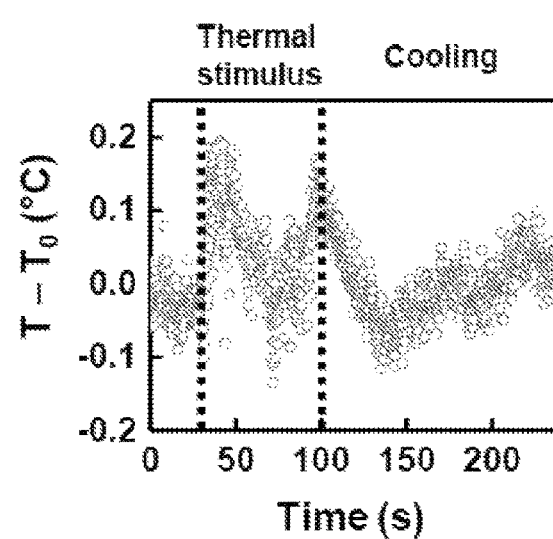
Figure 8D:
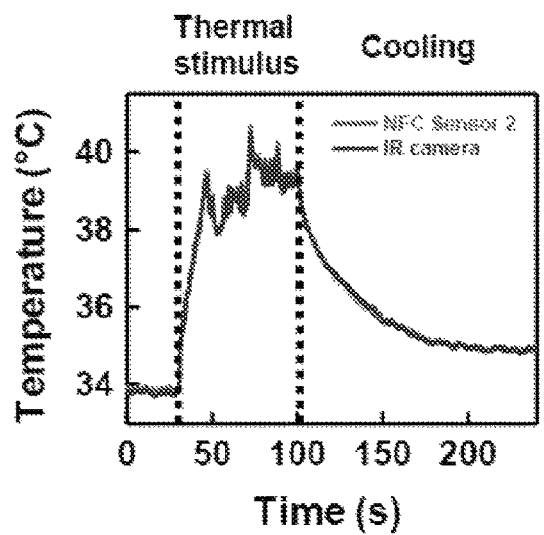
Figure 8E:
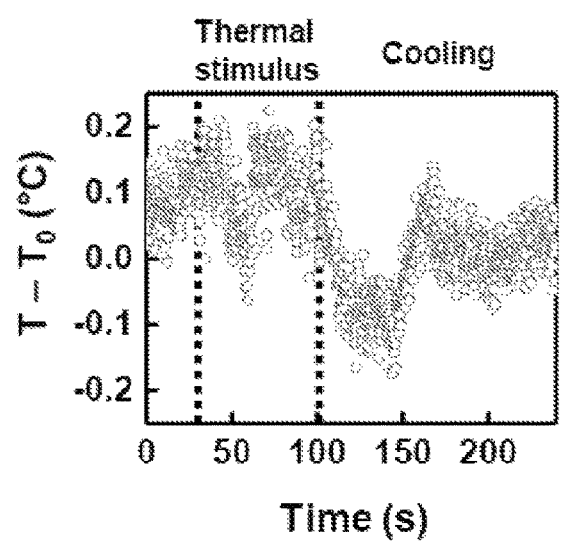
Figure 8F:
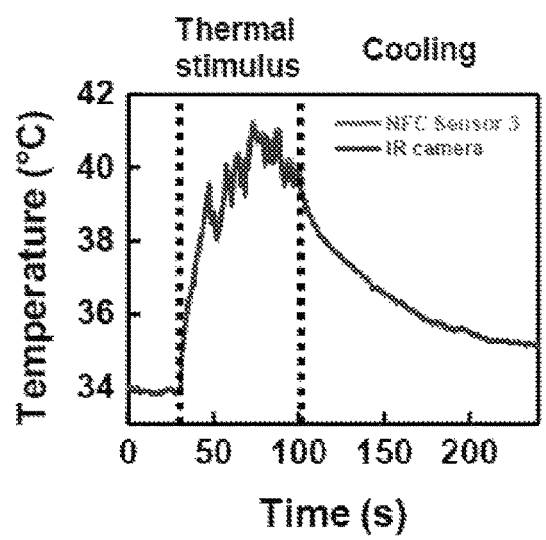
Figure 8G:
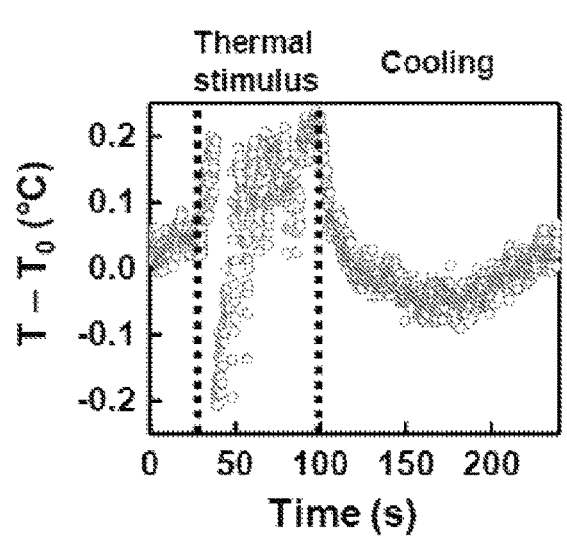

FIGS. 6A-6D show the results of tests to define calibration factors for the output of a wireless sensor in an embodiment. As in FIG. 6A, the tests involved placing a sensor on an anodized Al plate on a hotplate. Measurements from the sensor and readings from an IR camera were collected as the temperature changed from 25° C. to 50° C. Each sensor requires a slightly different calibration factor, defined by a single multiplier that converts the wireless reading to a value that matches that from the IR camera, as shown in FIG. 6D.

Supplementary Note 4: Pressure Measurement and Calibrations.

Figure 11C:
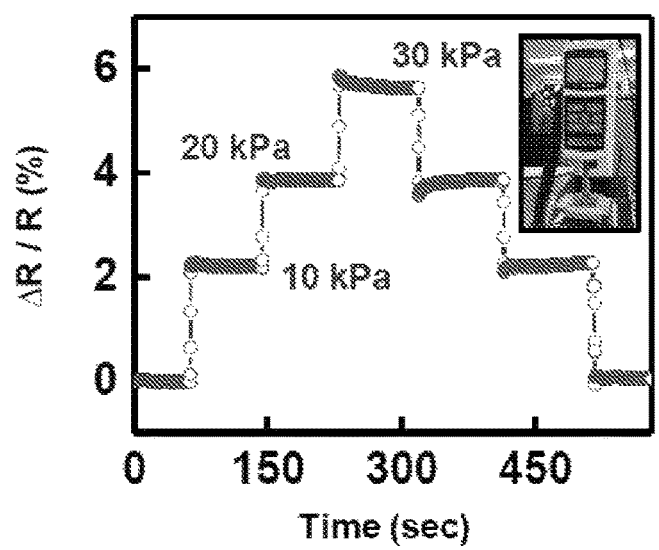
Figure 11D:
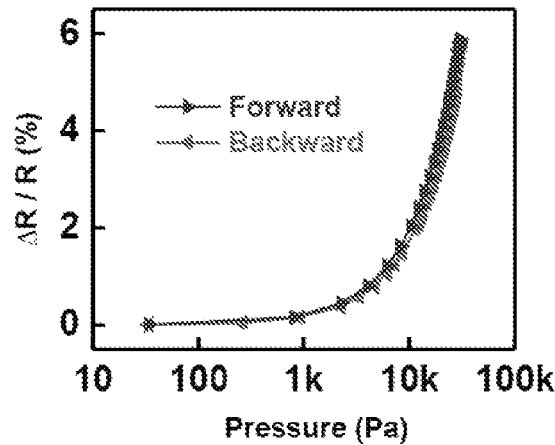

Detailed characterization of the pressure sensor in this embodiment appears in FIGS. 11A-11F. A commercial force gauge (e.g., Copiague, NY, Mark-10, Resolution: ±0.25%) fixed on a Z-stage controller with a 6.6 mm diameter of circle shape tip serves as a controlled source of pressure as shown in inset image of FIG. 11C. The tip contacted the entire region of the pressure sensor, the fractional change in resistance of the silicon spiral structure ($\Delta R/R$) occurs in a systematic manner, with no measurable hysteresis. FIG. 11C presents 1) changes in resistance for applied pressures of 10, 20, and 30 kPa 2) changes associated with constant pressure over a period of time and 3) obtaining similar value at certain pressure read even after releasing maximum pressure on sensor, keeping the same performance. FIG. 11D presents resistance changes under continuously increasing and then decreasing pressures between 0 and 30 kPa.

Figure 11E:
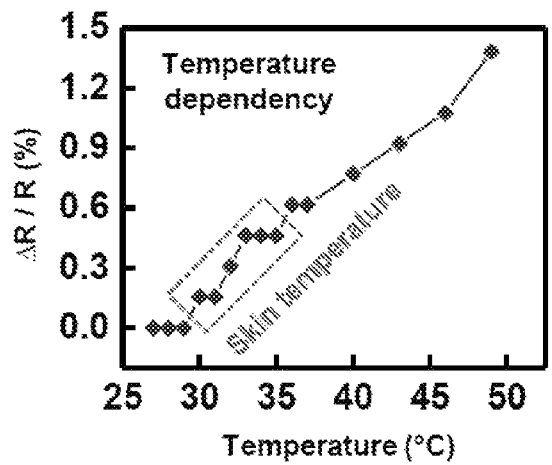
Figure 11F:
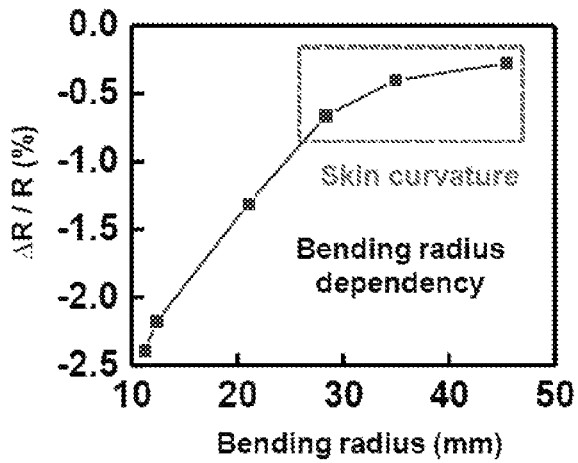

Changes in resistance associated with changes in temperature or bending radius are important to understand. FIG. 11E presents the changes in resistance associated with temperature changes between 25 and 50° C. For a range relevant to skin temperatures (red box), the resistance change is 0.5%, that is ~2 kPa pressure change range on the flat surface. FIG. 11F summarizes changes in resistance as a function of bending radius. For most cases of relevance to mounting on the body (red box), the bending induced change in resistance is 0.8%, that is ~3 kPa pressure change range on the flat surface. In practice, the temperature and degree of bending associated with mounting on the body set a baseline from which additional changes in resistance can be associated with pressure. Further, the temperature reading from the device can be used to extract from the pressure measurement any effect of changes in temperature.

Supplementary Note 5: FEA for the Thermal Simulation of an Encapsulated NFC Device.

ABAQUS commercial software was used to study the thermal response of the encapsulated NFC sensor on a forearm. The thickness of the encapsulated NFC device is much smaller than the encapsulation layer (PDMS) such that thermal properties of the encapsulated NFC device can be neglected. A transient FEA model of encapsulation layer as FIG. 9A, with the initial temperature of 23° C. (the same as the ambient temperature), constant temperature boundary (the same as the forearm temperature, 34° C.) at bottom surface, and material properties of PDMS (thermal conductivity k=0.15 W·m⁻¹K⁻¹, heat capacity c=1380 J·kg⁻¹K⁻¹, and density ρ=970 kg·m⁻³), is established. FIG. 2B gives the chip layer temperature versus time with the fixed 300 μm-thick top encapsulation layer and several bottom encapsulation layer thicknesses (50 μm, 100 μm and 200 μm). FIGS. 9B-9E show the temperature distribution at the cross-section, chip layer and top surface with several time (0 s, 0.1 s, 0.2 s, 0.5 s, 1 s and 5 s) and bottom encapsulation layer thicknesses (50 μm, 100 μm and 200 μm). The thinner the bottom encapsulation layer, the closer the steady-state temperature of the chip layer is to the prosthetic temperature (33.89° C., 33.81° C. and 33.66° C. for 50 μm-, 100 μm- and 200 μm-thick bottom encapsulation layers, respectively). In addition, 50 μm-thick bottom encapsulation layer reaches the steady-state temperature faster than 100 μm- and 200 μm-thick bottom encapsulation layers.

Supplementary Note 6: Theory for the Thermal Response Time of an Encapsulated Device.

Figure 9A:
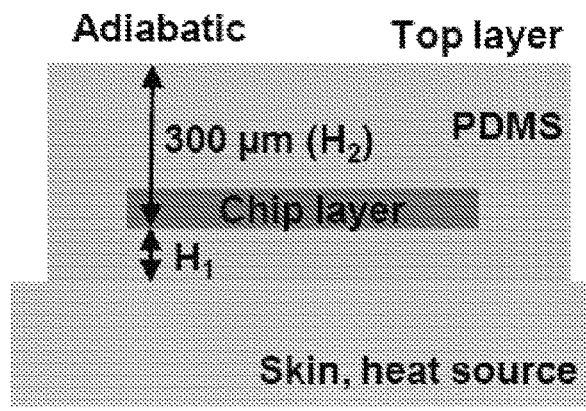
FIGS. 9A-9E illustrate the geometry used to model temperature calculations and resultant temperature distribution at the cross section, chip layer and top surface over time for different encapsulation thicknesses (50 μm, 100 μm and 200 μm).
Figure 9B:
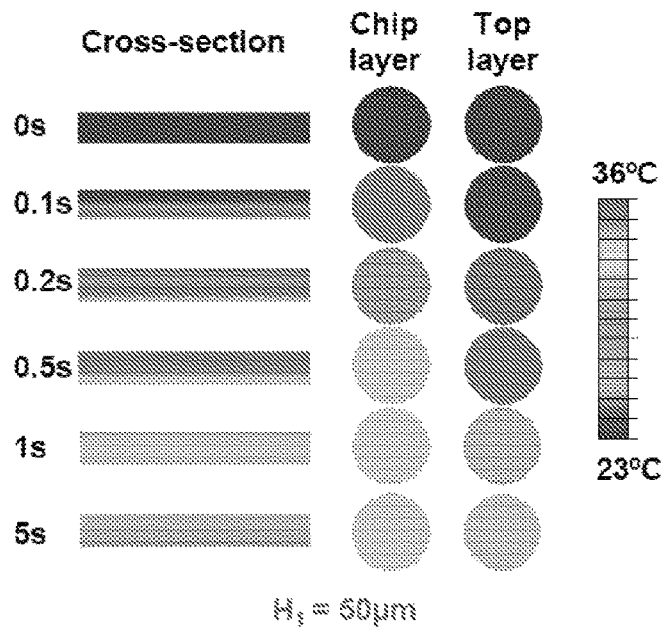
Figure 9C:
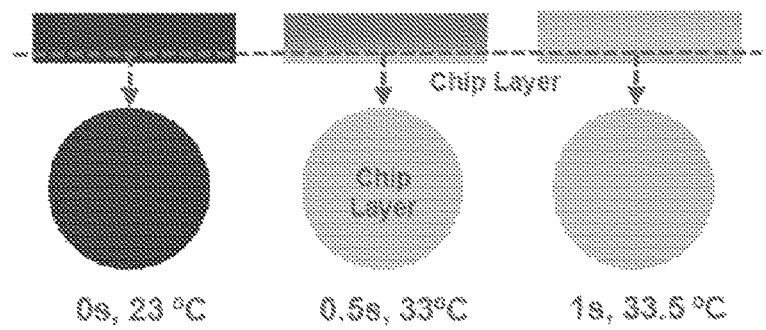
Figure 9E:
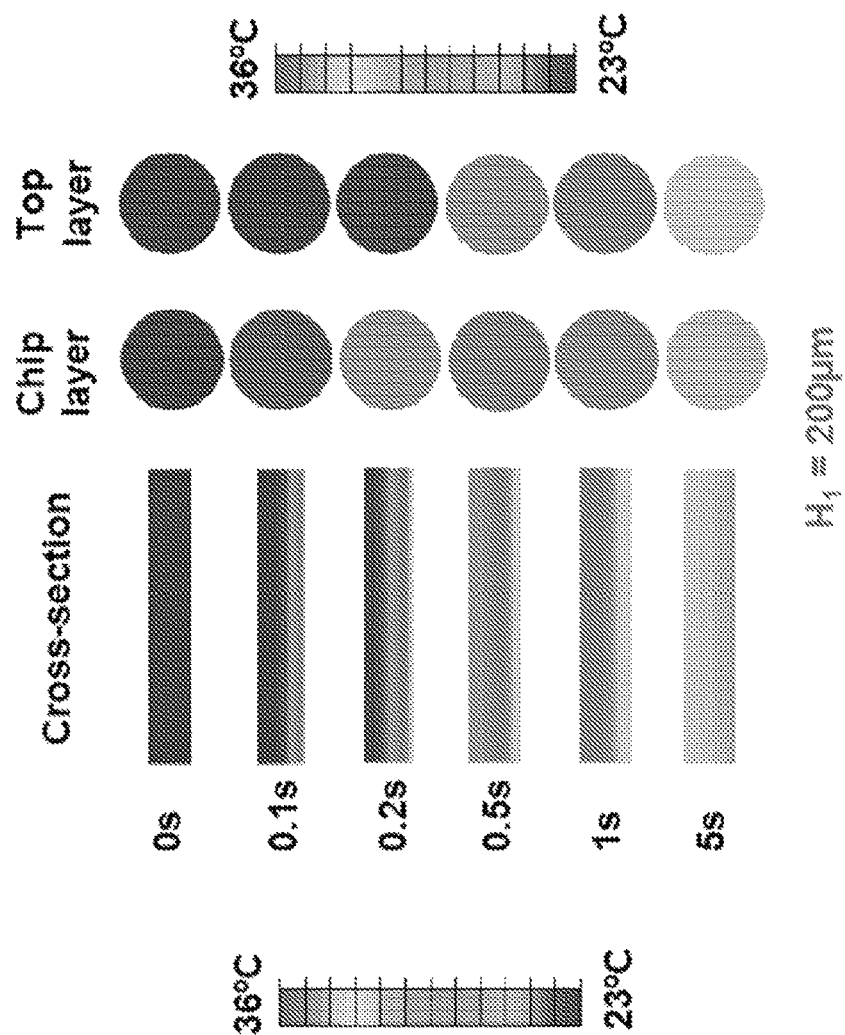
Figure 9D:
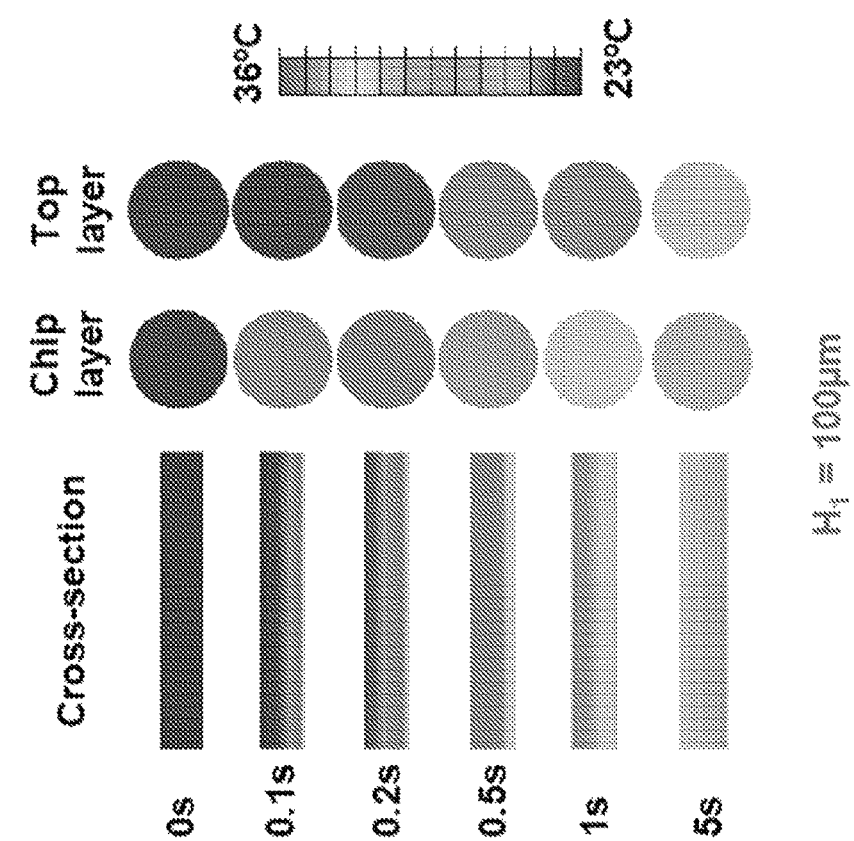

FIG. 9A depicts an embodiment where an encapsulated device involves layers of PDMS on the top and bottom surfaces. The in-plane dimensions of these layers are much larger than its thickness, such that the heat flux is mainly along the thickness direction, which can be represented by a one-dimensional heat transfer model $$\frac{\partial T}{\partial t} - \alpha \frac{\partial^2 T}{\partial x^2} = 0 \tag{S1}$$

where T is the temperature, $\alpha = k/\rho c$ is the thermal diffusivity of PDMS, and the coordinate x is along the thickness direction. The initial temperature of the PDMS is assumed the same as the ambient temperature $$T|_{t=0} = T_{initial} \tag{S2}$$

The skin provides a constant temperature $T_{skin}$ at the bottom of the PDMS $$T|_{x=0} = T_{skin} \tag{S3}$$

The numerical analysis suggests that the natural convection at the top surface of the PDMS has a negligible effect and can be approximated by a thermal isolation condition $$\frac{\partial T}{\partial x}\bigg|_{x=H_1+H_2} = 0 \tag{S4}$$

Eqs. (1-4) give temperature at encapsulated NFC device ($x=H_1$) versus time as $$T_{sensor} = \tag{S5}$$

$$T_{skin} - (T_{skin} - T_{initial}) \sum_{n=1}^{\infty} \frac{4}{\pi(2n-1)} e^{-\frac{\pi^2(2n-1)^2 kt}{4\rho c(H_1+H_2)^2}} \sin\left[\frac{\pi(2n-1)H_1}{2(H_1+H_2)}\right]$$

With $T_{initial}$=23° C., $T_{skin}$=34° C., $H_2$=300 μm, material properties of PDMS as k=0.15 W·m⁻¹K⁻¹, c=1380 J·kg⁻¹K⁻¹, and ρ=970 kg·m⁻³, FIG. 2B shows the temperature at encapsulated NFC device ($H_1$=300 μm) versus time with different $H_1$ (50 μm, 100 μm and 200 μm).

The sensor response time is defined by the time at which the sensor temperature change ($T_{sensor}-T_{initial}$) reaches 99% of the temperature difference between the skin and ambient temperature ($T_{skin}-T_{initial}$) The sensor response time is 1.6 s, 2.4 s and 4.0 s for $H_1$=50 μm, 100 μm and 200 μm, respectively.

Supplementary Note 7: FEA for Mechanics Simulation of a Pressure Sensor with or without the PET Layer.

ABAQUS commercial software was used to study the mechanics response of a pressure sensor with or without the PET layer on a skin. Pressure sensors [200 nm-thick Si (elastic modulus 130 GPa and Poisson's ratio 0.27) with or without a 5 μm-thick PET layer (elastic modulus 4.5 GPa and Poisson's ratio 0.35)] are encapsulated by two PDMS layers (300 μm at top and 50 μm at bottom, elastic modulus 145 kPa and Poisson's ratio 0.5), which are then mounted on a skin (elastic modulus 130 kPa and Poisson's ratio 0.5), and subjected to 10 kPa pressure on the top surface. FIG. 2H shows the maximum principal strain distribution at the top surface of Si membrane with or without the PET layer. The distribution of strain with the PET layer is more uniform than that without the PET layer.

Supplementary Note 8: FEA for the Mechanics Simulation of an Encapsulated Device.

Figure 12A:
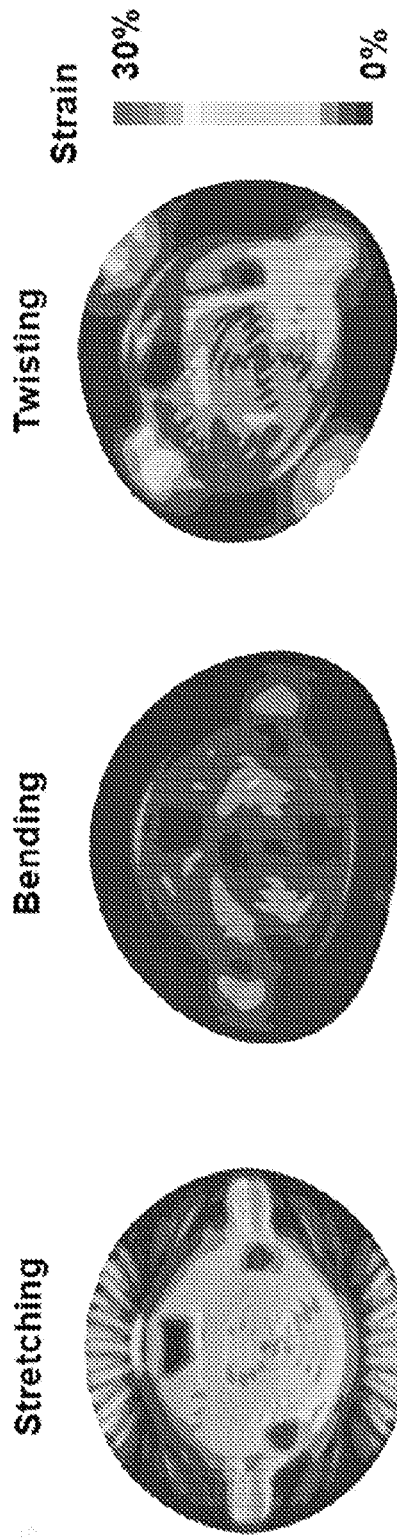
FIGS. 12A-12B. FEA results of strain of deformed encapsulated NFC devices.
Figure 12B:
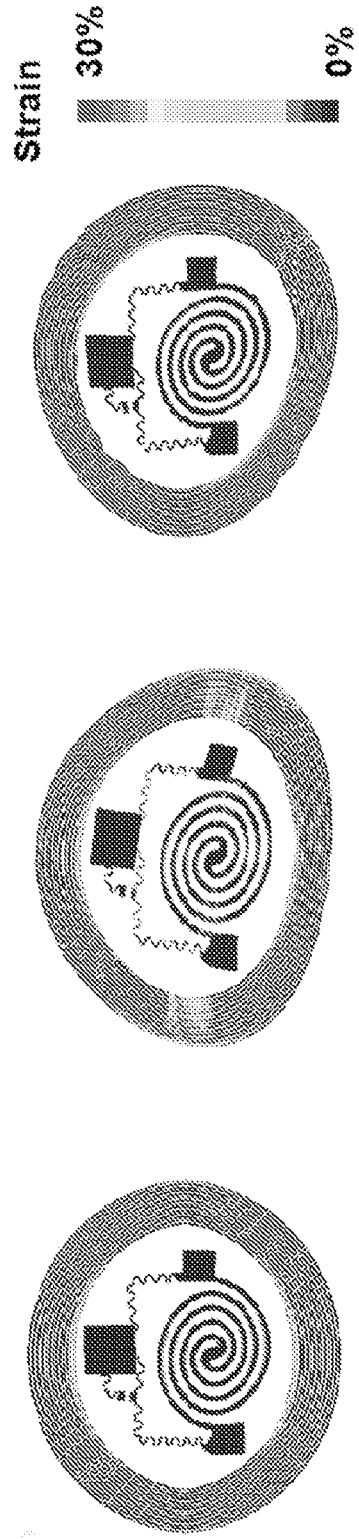

ABAQUS commercial software was used to study the mechanics response of an encapsulated NFC sensor on a phantom skin. The encapsulated NFC device {coil [1.2 μm-thick PI (elastic modulus 2.5 GPa and Poisson's ratio 0.34)/5 μm-thick Cu (elastic modulus 119 GPa and Poisson's ratio 0.34)/1.2 μm-thick PI], chip (100 μm-thick Si), serpentines (1.2 μm-thick PI/2 μm-thick Cu/1.2 μm-thick PI) and pressure sensor (5 μm-thick PET/200 nm-thick Si)} is encapsulated by two PDMS layers (300 μm at top and 50 μm at bottom), which are then mounted on a phantom skin (70×50×5 mm, PDMS with elastic modulus 145 kPa and Poisson's ratio 0.5) through a 50 μm-thick Scapa tape layer (elastic modulus 17 kPa and Poisson's ratio 0.5). FIGS. 12A-12B show the FEA results of the deformed shape of the encapsulated NFC device on a deformed phantom skin under different types of external loads (stretching, bending and twisting). The stretching strain is defined as the percentage elongation of the phantom skin. The bending and twisting angles are defined as the relative in-plane and out-of-plane angle of rotation between two ends of the phantom skin. The stretching strain, bending and twisting angles are 30%, 180° and 90°, respectively, for the three types of external loads. The corresponding maximum strain in copper layer as shown in FIG. 12B is below the fracture limit (5%) under all the three loading conditions, i.e., there is no fracture. For 30% stretching strain, the interfacial stresses between the encapsulated NFC device and phantom skin (FIG. 13) are within 20 kPa (normal skin sensitivity), i.e., the skin will not feel the device.

The systems may have an onboard power supply, such as a battery, supercapacitor, or the like, or may be without such an onboard power supply, such as device control by inductive coupling, inductive coils, or the like. The systems may correspond to a single mode stimulation or multiple mode stimulation, with or without integrated sensor feedback. There may be similar or identical devices positioned across the body, or the devices may be different, with different devices tailored to specific underlying or adjacent body surface and/or the application of interest. Similarly, depending on the application of interest, the number of individual devices (e.g., sensors/actuators) may be in one package at one location, or be configured as a plurality of devices that provide comprehensive body coverage, such as ranging up to 100,000 or even more, depending on the body surface area.

The systems are compatible with any of a wide range of configurations and form factors. They may be, for example, in a button-type rigid configuration, all the way to relatively thin and conformable configurations, for intimate skin surface contact, including via decal-type systems. The systems may be mounted to directly touch the skin. Alternatively, the systems may be mounted on or in a material, such as clothing-type fabric or mesh, that then is put on, covers, or wraps the body or desired portion of the body. The fabric itself may be conformal to the body, such as spandex, elastane or any other synthetic or natural material or fiber. In this manner, relatively thick and or non-conformal devices may be reliably positioned in intimate contact with a body surface, including a surface of a living body. The devices themselves may be interconnected with wires embedded in the fabric, or may be wirelessly interconnected for desired spatio-temporal sensing and/or actuation. Applications may range from virtual-reality type actuation, where a user is immersed in the virtual environment, including in a gaming or interactive scenario, to safety monitoring, where changes in pressure over a certain area or region, such as the chest region, may be used to reflect a safely breathing individual compared to a lack of change that may reflect an individual has stopped breathing. Similarly, temperature distribution and electrical activity may provide similar information and indications, including overheating or an adverse medical event, such as a heart attack or infarct.

Aspects of the systems that provide access to relevant applications include, but are not limited to, distribution of large collections of the devices. As described herein the technology allows for distribution of large or miniaturized skin-mounted devices across the entire body, with full wireless power delivery, control and data transmission. For example, collections of 64 to 128, or more, individual devices (sensors and/or actuators) in the systems are provided herein, readily scalable to many more, as desired. In addition to capabilities in sensing (and other modes of sensing), actuators can be integrated with the sensors in a single device platform or in platform formed of a collection of separate devices. In this manner, feedback may be provided to an individual, including to patients who are at risk for pressure-induced ulcers, bed sores, etc. Of course, the systems described herein have a wide range of applications. Any power requirements of the actuators may be addressed through local storage capabilities, including supercapacitors or batteries, that can be charged continuously via wireless power delivery.

Relevant aspects of the system include physical components, such as devices having sensors and/or actuators positioned over a body surface, a wireless interface for receiving and communicating data, signals, inputs, etc. and relevant software-based controllers that easily and reliably control the sensors/actuators, including at a distance such as over the internet, the cellular network, satellite network, or any other platform where data transmission is reliable.

Referring to the figures, a medical device 10 may have a plurality of biologically interactive devices 20 configured for interacting with a biological surface. For example, FIG. 1A illustrates the biologically interactive devices 20 distributed over a a biological surface 30 that is skin. FIG. 1B illustrates sensors 40, specifically a temperature sensor 42 and a pressure sensor 44. FIG. 1C illustrates other components, including a wireless controller 50, including a NFC chip that may also provide temperature sensing capability. Wireless transmitter 60 may correspond to a NFC coil, such as for communicating an output 70 form the biologically interactive devices to a remote receiver 80, such as mobile device, smartphone or computer. The remote received may be long-range reader 90, illustrated as a smart phone in FIG. 3A. The inset in the middle panel illustrates the wireless communication between communication chip 52 (such as NFC chip) and the reader 90. A processor 110 in the reader may be used to calculate a relevant physiological parameter. The resultant transmitted data may be displayed as a map 100, including a spatio-temporal map 100 101 where the physiological parameter is displayed over a digital rendering of the biological surface (FIG. 1A). For any of the devices and methods, physiological parameter may be mathematically interpolated between adjacent sensors, thereby providing a spatially continuous map although there are distinctly positioned sensors, with adjacent sensors spatially separated from each other.

As desired, the medical device may be incorporated into a garment 120, or may be positioned between a skin surface and an overlying garment, such as a spandex-type material that will hold the biologically interactive devices in place.

Other components of the device may include wireless energy harvester 160, analog to digital converter 46 (incorporated as part of chip 50). The pressure sensor 44 may be formed of an ultrathin spiral shape layer of monocrystalline silicon 130, including between top polymer layer 140 and bottom polymer layer 150. Magnetic inductive loop antenna 160 (corresponding to energy harvester) may wirelessly interface with the reader, and may be embedded in a substrate 170. As desired, an alarm or alert 180 may display on the reader 80 to indicate status, including an out of safe range reading, or where action is required, such as due to extreme temperature, prolonged pressure, hydration loss, abnormal galvanic skin response.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The following publications are specifically incorporated by reference for various methods of making, sensors, actuators, wireless power and control, and related components, configurations and mechanical characteristics associated with skin-mountable systems: Pub No. 2013/0041235A1, published Feb. 14, 2013, application Ser. No. 13/492,636, filed Jun. 8, 2012; Pub No. WO 2017/004576, published Jan. 5, 2017; Appl No. PCT/US16/40814, filed Jul. 1, 2016; Pub No. WO 2016/025438, published Feb. 18, 2016, Appl No. PCT/US15/44588, filed Aug. 11, 2015; Pub No. WO 2016/025468, published Feb. 18, 2016; Appl No. PCT/US15/44638, filed Aug. 11, 2015; Pub No. WO 2016/196673, published Dec. 8, 2016; Appl No. PCT/US16/35331, filed Jun. 1, 2016; and Pub No. WO 2016/196675, published Dec. 8, 2016; Appl No. PCT/US16/35336, filed Jun. 1, 2016.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

When a Markush group or other grouping is used herein, all individual members of the group and all combinations and subcombinations possible of the group are intended to be individually included in the disclosure.

Every formulation or combination of components described or exemplified herein can be used to practice the invention, unless otherwise stated.

Whenever a range is given in the specification, for example, a density range, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A medical device, comprising:
a plurality of biologically interactive devices configured for interacting with a large area biological surface, the biologically interactive devices each comprising a sensor for measuring a physiological parameter of the biological surface;
a wireless controller configured to wirelessly operate the plurality of biologically interactive devices; and
a wireless transmitter for wirelessly communicating an output from said plurality of biologically interactive devices to a remote receiver,
wherein the wireless controller provides two-way communication with the plurality of biologically interactive devices to acquire physiological parameter data from the plurality of sensors and to operate the plurality of biologically interactive devices;
wherein the wireless controller is configured to acquire a continuous data stream from said medical device and generate a spatio-temporal map of one or more physiological parameters detected by the sensors; and
wherein the spatio-temporal map has a map area that corresponds to a full-body surface.

2. The medical device of claim 1, wherein the full-body surface corresponds to at least 80% of a living animal skin surface.

3. The medical device of claim 1, further comprising a processor to provide an average physiological parameter over the full-body surface, a time-integrated physiological parameter, a rate of change of the physiological parameter, or any combination thereof.

4. A medical device, comprising:
a plurality of biologically interactive devices configured for interacting with a large area biological surface, the biologically interactive devices each comprising a sensor for measuring a physiological parameter of the biological surface, wherein each biologically interactive device comprises:
an integrated circuit chip for NFC communication;
a wireless energy harvester;
a temperature sensor;
an analog to digital converter; and
a pressure sensor;
a wireless controller configured to wirelessly operate the plurality of biologically interactive devices;
a wireless transmitter for wirelessly communicating an output from said plurality of biologically interactive devices to a remote receiver; and
a magnetic inductive loop antenna configured to wirelessly interface with an external reader antenna,
wherein the external reader antenna is embedded in an external reader antenna substrate.

5. The medical device of claim 4, wherein the external reader substrate is a sheet, a mattress cover, or a mattress surface.

6. A medical device, comprising:
a plurality of biologically interactive devices configured for interacting with a large area biological surface, the biologically interactive devices each comprising a sensor for measuring a physiological parameter of the biological surface;
a wireless controller configured to wirelessly operate the plurality of biologically interactive devices; and
a wireless transmitter for wirelessly communicating an output from said plurality of biologically interactive devices to a remote receiver;
wherein the medical device is adapted for full-body spatio-temporal mapping of the physiological parameter over a skin surface area; and
wherein a number of individual biologically interactive devices are selected and spatially positioned so as to achieve an average physiological parameter spatial resolution at least as good as 5 cm over a monitored surface area.

7. The medical device of claim 6, having a device footprint that is greater than or equal to 10 $cm^2$ and less than or equal to 20 $m^2$.

8. A method of monitoring a physiological parameter, the method comprising the steps of:
interfacing a plurality of spatially distributed biologically interactive devices with a body surface;
detecting a physiological parameter with a sensor in each of the plurality of spatially distributed biologically interactive devices;
wirelessly transmitting the detected physiological parameter to a receiver;
generating a spatial distribution map of the detected physiological parameter across the interfaced body surface;
thereby monitoring the physiological parameter; and
periodically repeating the interfacing step to generate a spatio-temporal distribution map of the detected physiological parameter.

9. The method of claim 8, wherein the sensor is a pressure sensor for evaluating risk of a skin-ulcer in a patient positioned on a bed.

10. The method of claim 8, wherein the sensor is a temperature sensor for a sleep study.

11. The method of claim 8, wherein the body surface corresponds to at least 80% of a whole-animal body surface area.

* * * * *